(12) United States Patent
Au et al.

(10) Patent No.: US 12,123,866 B2
(45) Date of Patent: Oct. 22, 2024

(54) NANOPORE SEQUENCING DEVICE COMPRISING RUTHENIUM-CONTAINING ELECTRODES

(71) Applicant: Roche Sequencing Solutions, Inc., Pleasanton, CA (US)

(72) Inventors: Wing Kei Au, San Jose, CA (US); Jason Komadina, Fremont, CA (US); Marowen Ng, San Jose, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 711 days.

(21) Appl. No.: 17/249,275

(22) Filed: Feb. 25, 2021

(65) Prior Publication Data
US 2021/0311017 A1    Oct. 7, 2021

Related U.S. Application Data

(63) Continuation of application No. PCT/EP2019/072684, filed on Aug. 26, 2019.

(60) Provisional application No. 62/723,871, filed on Aug. 28, 2018.

(51) Int. Cl.
G01N 33/487  (2006.01)
C12Q 1/6869  (2018.01)

(52) U.S. Cl.
CPC ..... *G01N 33/48721* (2013.01); *C12Q 1/6869* (2013.01)

(58) Field of Classification Search
CPC ............ G01N 33/48721; C12Q 1/6869; C12Q 2565/631; B01L 2300/0645; B01L 2300/0896
See application file for complete search history.

(56) References Cited

U.S. PATENT DOCUMENTS

| | | |
|---|---|---|
| 5,963,417 A | 10/1999 | Anderson |
| 8,324,914 B2 | 12/2012 | Chen et al. |
| 9,377,437 B2 | 6/2016 | Chen et al. |
| 9,557,294 B2 | 1/2017 | Chen et al. |
| 9,605,309 B2 | 3/2017 | Davis et al. |
| 2007/0095664 A1 * | 5/2007 | Chou ............... C23C 14/08 204/192.1 |

(Continued)

FOREIGN PATENT DOCUMENTS

| | | | |
|---|---|---|---|
| JP | 2018072353 A | 5/2018 | |
| WO | 2013109970 A1 | 7/2013 | |
| WO | WO-2017059094 A2 * | 4/2017 | ........... C12Q 1/6886 |

OTHER PUBLICATIONS

Derrington, et al. Nanopore DNA sequencing with MspA. Proc Natl Acad Sci US A. Sep. 14, 2010;107 (37):16060-5. Epub Aug. 26, 2010.

(Continued)

*Primary Examiner* — C. Sun

(74) *Attorney, Agent, or Firm* — Roche Sequencing Solutions, Inc.

(57) ABSTRACT

Disclosed herein are ruthenium-containing materials, such as ruthenium containing materials having a double layer capacitance ranging from between about 180 pF/um$^2$ to about 320 pF/um$^2$. In some embodiments, the ruthenium-containing materials are suitable for use in electrodes. In some embodiments, the ruthenium-containing materials are suitable for use in nanopore sequencing devices.

18 Claims, 50 Drawing Sheets

(56) References Cited

U.S. PATENT DOCUMENTS

| | | |
|---|---|---|
| 2007/0271751 A1 | 11/2007 | Weidman |
| 2011/0193570 A1 | 8/2011 | Genia |
| 2013/0244340 A1* | 9/2013 | Davis .............. G01N 33/48721 436/501 |
| 2014/0312002 A1 | 10/2014 | Peng et al. |
| 2015/0107996 A1 | 4/2015 | Chen |
| 2015/0344945 A1 | 12/2015 | Mandell et al. |
| 2016/0216233 A1* | 7/2016 | Hovis .............. G01N 33/48721 |
| 2017/0268052 A1 | 9/2017 | Genia |
| 2018/0016629 A1 | 1/2018 | Bi et al. |
| 2018/0073071 A1 | 3/2018 | Ju et al. |

OTHER PUBLICATIONS

International Search Report and Written Opinion mailed Mar. 10, 2020 in connection with PCT/EP2019/072684 filed Aug. 26, 2019, 18 pages.

Kasianowicz et al, Characterization of individual polynucleotide molecules using a membrane channel, Proceedings of the National Academy of Sciences USA, Nov. 1996, p. 13770-13773, vol. 93.

* cited by examiner

NANOPORE SEQUENCING DEVICE COMPRISING RUTHENIUM-CONTAINING ELECTRODES

CROSS REFERENCE TO RELATED APPLICATIONS

This application is a continuation of International Patent Application No. PCT/EP2019/072684, filed Aug. 26, 2019, which claims priority to U.S. Provisional Patent Application No. 62/723,871, filed Aug. 28, 2018, entitled RUTHENIUM-CONTAINING ELECTRODES, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to electrodes, and more particularly to electrodes for use in nucleic acid sequencing.

BACKGROUND OF THE DISCLOSURE

The importance of DNA sequencing has increased dramatically from its inception four decades ago. It is recognized as a crucial technology for most areas of biology and medicine and as the underpinning for the new paradigm of personalized and precision medicine. Information on individuals' genomes and epigenomes can help reveal their propensity for disease, clinical prognosis, and response to therapeutics, but routine application of genome sequencing in medicine will require comprehensive data delivered in a timely and cost-effective manner.

Nanopore-based nucleic acid sequencing is an approach that has been widely studied. In the last two decades, there has been great interest in taking advantage of nanopores for polymer characterization and for distinguishing nucleotides in a low-cost, rapid, single-molecule manner. For example, Kasianowicz et. al. characterized single-stranded polynucleotides as they were electrically translocated through an alpha hemolysin nanopore embedded in a lipid bilayer (see, e.g., Kasianowicz, J. (1996), Characterization of Individual Polynucleotide Molecules using a Membrane Channel. Proc. Natl. Acad. Sci., 93, 13770-3). It was demonstrated that during polynucleotide translocation partial blockage of the nanopore aperture could be measured as a decrease in ionic current. Similarly, Gundlach et. al. demonstrated a method of sequencing DNA that used a low noise nanopore derived from *Mycobacterium smegmatis* ("MspA") in conjunction with a process called duplex interrupted sequencing (see, e.g., Derrington, I. et al. (2010), Nanopore DNA Sequencing with MspA. Proc. Natl. Acad. Sci., 107(37), 16060-16065). Here, a double strand duplex was used to temporarily hold the single-stranded portion of the nucleic acid in the MspA constriction. Akeson et. al. (see, e.g., PCT Publication No. US20150344945A1) disclose methods for characterizing polynucleotides in a nanopore that utilize an adjacently positioned molecular motor to control the translocation rate of the polynucleotide through or adjacent to the nanopore aperture.

In general, three nanopore sequencing approaches have been pursued: strand sequencing in which the bases of DNA are identified as they pass sequentially through a nanopore, exonuclease-based nanopore sequencing in which nucleotides are enzymatically cleaved one-by-one from a DNA molecule and monitored as they are captured by and pass through the nanopore, and a nanopore sequencing by synthesis (SBS) approach in which identifiable polymer tags are attached to nucleotides and registered in nanopores during enzyme-catalyzed DNA synthesis. Common to all these methods is the need for precise control of the reaction rates so that each base is determined in order. Strand sequencing requires a method for slowing down the passage of the DNA through the nanopore and decoding a plurality of bases within the channel; ratcheting approaches, taking advantage of molecular motors, have been developed for this purpose. Exonuclease-based sequencing requires the release of each nucleotide close enough to the pore to guarantee its capture and its transit through the pore at a rate slow enough to obtain a valid ionic current signal. In addition, both of these methods rely on distinctions among the four natural bases, two relatively similar purines and two similar pyrimidines. The nanopore SBS approach utilizes synthetic polymer tags attached to the nucleotides that are designed specifically to produce unique and readily distinguishable ionic current blockade signatures for sequence determination.

SUMMARY OF THE DISCLOSURE

In one aspect of the present disclosure is a nanopore sequencing device comprising: (i) an electrode comprised of a ruthenium-containing material; and (ii) and at least one of a reference electrode or counter electrode. In some embodiments, the ruthenium-containing material comprises at least two of ruthenium, oxygen, and nitrogen. In some embodiments, the ruthenium containing materials comprises at least one of ruthenium-nitride and ruthenium-oxynitride. In some embodiments, the ruthenium-containing material is characterized as having a double-layer capacitance ranging from between about 180 pF/um$^2$ to about 320 pF/um$^2$. In some embodiments, the ruthenium-containing material is characterized as having a surface composition ratio of (N+O)/Ru as measured by X-ray photoelectron spectroscopy ranging from between about 1.5 and about 3.5. In some embodiments, the surface composition ratio ranges from about 1.8 to about 3.0. In some embodiments, the surface composition ratio ranges from about 2 to about 2.5. In some embodiments, the surface composition ratio ranges from about 2 to about 2.2. In some embodiments, the surface composition ratio ranges from about 2.1 to about 2.4. In some embodiments, the ruthenium-containing material is characterized as having a nitrogen content of at least about 5% nitrogen but not more than about 15%. In some embodiments, the electrode comprises a dendritic structure as determined by cross-sectional scanning electron microscopy. In some embodiments, the nanopore sequencing device further comprises a dielectric material disposed on a surface of the electrode. In some embodiments, the electrode is disposed on a metal layer. In some embodiments, the nanopore sequencing device comprises a plurality of electrodes arranged on a chip.

In another aspect of the present disclosure is a chip comprising a plurality of individually addressable nanopores, wherein each individually addressable nanopore is in fluidic communication with a working electrode comprised of a ruthenium-containing material. In some embodiments, the ruthenium-containing material comprises ruthenium, oxygen, and nitrogen. In some embodiments, the ruthenium-containing material is characterized as having a double-layer capacitance ranging from between about 180 pF/um$^2$ to about 320 pF/um$^2$. In some embodiments, the ruthenium-containing material is characterized as having a surface composition ratio of (N+O)/Ru as measured by X-ray photoelectron spectroscopy ranging from between about 1.5 and about 3.5. In some embodiments, the surface composition ratio ranges from about 1.8 to about 3.0. In some embodiments, the surface composition ratio ranges from about 2 to about 2.5. In some embodiments, the surface composition ratio ranges from about 2 to about 2.2. In some embodiments, the surface composition ratio ranges from about 2.1 to about 2.4. In some embodiments, the ruthenium-containing material is characterized as having a nitrogen content of at least about 5% nitrogen but not more than about 15%. In some embodiments, the working electrode comprises a columnar structure as determined by cross-sectional scanning electron microscopy. In some embodiments, the working electrode comprises a dendritic structure as determined by cross-sectional scanning electron microscopy.

In another aspect of the present disclosure is a nanopore sequencing device comprising a chip or a biochip comprising a plurality of individually addressable nanopores, wherein each individually addressable nanopore is in fluidic communication with a working electrode comprised of a ruthenium-containing material. In some embodiments, the ruthenium-containing material is characterized as having a double-layer capacitance ranging from between about 180 pF/um$^2$ to about 320 pF/um$^2$.

In another aspect of the present disclosure is a nanopore sequencing device comprising: a working electrode comprised of a ruthenium-containing material; and a dielectric layer, wherein a portion of the dielectric layer is disposed horizontally adjacent to the working electrode and a portion of the dielectric layer is disposed above and covering a portion of the working electrode, and wherein the dielectric layer forms a well having an opening above an uncovered portion of the working electrode (see, e.g., U.S. Pat. No. 10,036,739, the disclosure of which is hereby incorporated by reference herein in its entirety). In some embodiments, the ruthenium-containing material is characterized as having a double-layer capacitance ranging from between about 180 pF/um$^2$ to about 320 pF/um$^2$. In some embodiments, ruthenium-containing material is characterized as having a surface composition ratio of (N+O)/Ru as measured by X-ray photoelectron spectroscopy ranging from between about 1.5 and about 3.5. In some embodiments, the surface composition ratio ranges from about 1.8 to about 3.0. In some embodiments, the surface composition ratio ranges from about 2 to about 2.5. In some embodiments, the surface composition ratio ranges from about 2 to about 2.2. In some embodiments, the surface composition ratio ranges from about 2.1 to about 2.4. In some embodiments, the ruthenium-containing material is characterized as having a nitrogen content of at least about 5% nitrogen but not more than about 15%. In some embodiments, the electrode comprises a dendritic structure as determined by cross-sectional scanning electron microscopy. In some embodiments, the nanopore sequencing device further comprises a surface above the dielectric layer, and wherein a membrane may form on top of the surface and span across the opening of the well above the uncovered portion of the working electrode. In some embodiments, a base surface area of the working electrode is greater than a base surface area of the opening above the uncovered portion of the working electrode.

In another aspect of the present disclosure is a ruthenium-containing film prepared according to the process: performing one of a sputter deposition or a plasma vapor deposition using a ruthenium target (e.g. a 95% pure, a 97% pure, or a 99% pure ruthenium metal target), wherein the sputter deposition or the plasma vapor deposition process comprises (i) introducing nitrogen into the deposition chamber at a flow rate of between about 10 sccm and 100 sccm, and (ii) introducing argon into the deposition chamber at a flow rate of about 10 sccm, and wherein a deposition pressure within the deposition chamber is maintained at between about 5 mTorr to about 25 mTorr during the deposition, and wherein the deposition is performed using a power ranging from about 50 watts to about 250 watts. In some embodiments, the deposition pressure is about 20 mTorr, the flow rate of nitrogen is about 90 sccm, and the power is about 200 watts. In some embodiments, the deposition process is conducted at room temperature. In some embodiments, ruthenium-containing film comprises a double layer capacitance ranging from between about 180 pF/um$^2$ to about 220 pF/um$^2$.

In some embodiments, the process further comprises heating the deposited ruthenium-containing film at a temperature greater than 120° C. In some embodiments, the heating is conducted at a temperature ranging from between 140° ° C. to about 340° ° C. In some embodiments, a surface composition ratio of (N+O)/Ru of the ruthenium-containing film, as measured by X-ray photoelectron spectroscopy, ranges from between about 1.5 and about 3.5. In some embodiments, the surface composition ratio ranges from between about 1.8 to about 3.2. In some embodiments, the ruthenium-containing film comprises at most 15% nitrogen by total weight of the film. In some embodiments, the ruthenium-containing film comprises at most 10% nitrogen by total weight of the film, but not less than 5% nitrogen by total weight of the film. In some embodiments, the ruthenium-containing film comprises a double layer capacitance ranging from between about 260 pF/um$^2$ to about 320 pF/um$^2$. In some embodiments, the ruthenium-containing film comprises a dendritic structure as determined by cross-sectional scanning electron microscopy. In some embodiments, the ruthenium-containing film comprises a face centered cubic structure.

In another aspect of the present disclosure is a stack deposited onto a substrate, a metal layer at least partially disposed on the surface of the substrate, an active layer disposed on the surface of the metal layer, and a cap layer at least partially disposed on the surface of the active layer, wherein the active layer comprises a ruthenium-containing film prepared by performing one of a sputter deposition or a plasma vapor deposition using a ruthenium target, wherein the sputter deposition or the plasma vapor deposition process comprises (i) introducing nitrogen into the deposition chamber at a flow rate of between about 10 sccm and 100 sccm, and (ii) introducing argon into the deposition chamber at a flow rate of about 10 sccm, and wherein a deposition pressure within the deposition chamber is maintained at between about 5 mTorr to about 25 mTorr during the deposition, and wherein the deposition is performed using a power ranging from about 50 watts to about 250 watts. In some embodiments, the active layer is at least partially surrounded by a dielectric material. In some embodiments, the cap layer is comprised of a dielectric material. In some embodiments, the stack may be thermally treated. In some embodiments, the ruthenium-containing material has a double-layer capacitance ranging from between about 180 pF/um$^2$ to about 320 pF/um$^2$. In some embodiments, the substrate is a semiconductor. In some embodiments, the substrate comprises a plurality of wells at a density of at least 200 wells/mm$^2$, and each well comprises the stack. In some embodiments, the density is at least 300 wells/mm$^2$. In some embodiments, the density is at least 400 wells/mm$^2$. In some embodiments, the density is at least 500 wells/mm$^2$. In some embodiments, the stack may be housed in a contained, e.g. a reservoir.

In another aspect of the present disclosure is a nanopore sequencing device comprising the stack identified above. In some embodiments, the stack may be placed in proximity to a counter electrode. In some embodiments, the stack may be positioned within a reservoir.

In another aspect of the present disclosure is a biochip comprising a plurality of individually addressable nanopores, wherein each individually addressable nanopore is in fluidic communication with a working electrode comprised of a ruthenium-containing material, wherein the ruthenium-containing material is prepared by performing one of a sputter deposition or a plasma vapor deposition using a ruthenium target, wherein the sputter deposition or the plasma vapor deposition process comprises (i) introducing nitrogen into the deposition chamber at a flow rate of between about 10 sccm and 100 sccm, and (ii) introducing argon into the deposition chamber at a flow rate of about 10 sccm, and wherein a deposition pressure within the deposition chamber is maintained at between about 5 mTorr to about 25 mTorr during the deposition, and wherein the deposition is performed using a power ranging from about 50 watts to about 250 watts. In some embodiments, the ruthenium-containing material has a double-layer capacitance ranging from between about 180 pF/um$^2$ to about 320 pF/um$^2$.

In another aspect of the present disclosure is a thin film deposited on a substrate, the thin film comprising ruthenium nitride, ruthenium oxide, ruthenium oxynitride, or a mixture thereof, and wherein the thin film has a double-layer capacitance ranging from between about 180 pF/um$^2$ to about 320 pF/um$^2$, and wherein the thin film has a nitrogen content of at least about 5% nitrogen but not more than about 15%. In some embodiments, the double layer capacitance ranges from between about 260 pF/um$^2$ to about 320 pF/um$^2$. In some embodiments, the double layer capacitance ranges from between about 280 pF/um$^2$ to about 300 pF/um$^2$. In some embodiments, surface composition ratio (N+O)/Ru of the thin film, as measured by X-ray photoelectron spectroscopy, ranges from between about 1.5 and about 3.5. In some embodiments, the surface composition ratio ranges from between about 1.8 to about 3.2 In some embodiments, the thin film comprises a dendritic structure as determined by cross-sectional scanning electron microscopy.

In another aspect of the present disclosure is an electrode comprising the ruthenium-containing thin film described above.

In another aspect of the present disclosure is a method of preparing an electrode comprising: etching a hole within a first dielectric layer disposed onto a conductive layer, wherein the hole comprises an exposed surface of a conductive layer; depositing a working electrode comprising a ruthenium-containing film at least onto the exposed surface of the conductive layer within the hole; and depositing a cap layer onto the surface of the working electrode. In some embodiments, the depositing of the working electrode comprises (i) performing one of a sputter deposition or a plasma vapor deposition using a ruthenium target to provide the ruthenium-containing film; and (ii) heating the provided ruthenium-containing film at a temperature of at least about 150° ° C.

In some embodiments, the working electrode is characterized as having a surface composition ratio (N+O)/Ru of the thin film, as measured by X-ray photoelectron spectroscopy, ranges from between about 1.5 and about 3.5. In some embodiments, the ratio ranges from about 2 to about 2.5. In some embodiments, the working electrode is characterized as having a double-layer capacitance ranging from between about 180 pF/um$^2$ to about 320 pF/um$^2$. In some embodiments, the working electrode is characterized as having a nitrogen content of at least about 5% nitrogen but not more than about 15%, and further characterized as having one of a columnar or dendritic structure as observed by cross-sectional scanning electron microscopy.

In some embodiments, the depositing of the working electrode comprises (i) performing one of a sputter deposition or a plasma vapor deposition using a ruthenium target, wherein the sputter deposition or the plasma vapor deposition process comprises (i) introducing nitrogen into the deposition chamber at a flow rate of between about 10 sccm and 100 sccm, and (ii) introducing argon into the deposition chamber at a flow rate of about 10 sccm, and wherein a deposition pressure within the deposition chamber is maintained at between about 5 mTorr to about 25 mTorr during the deposition, and wherein the deposition is performed using a power ranging from about 50 watts to about 250 watts; and (ii) heating the provided ruthenium-containing film at a temperature of at least about 150° ° C. In some embodiments, the heating is performed at least about 200° ° C.

In another aspect of the present disclosure is a nanopore sequencing device comprising: (i) an electrode having a double-layer capacitance ranging from between about 180 pF/um$^2$ to about 320 pF/um$^2$; and (ii) and at least one of a reference electrode or counter electrode. In some embodiments, the electrode is comprised of ruthenium, oxygen, and nitrogen, and wherein the electrode comprises at least about 5% nitrogen but not more than about 15%. In some embodiments, the electrode is comprised of a metal nitride. In some embodiments, the metal nitride is ruthenium nitride. In some embodiments, the electrode comprises ruthenium-nitride and ruthenium oxynitride.

In another aspect of the present disclosure is a nanopore sequencing device comprising a nanopore and an electrode in proximity to the nanopore, the electrode comprising a ruthenium-containing material having a double-layer capacitance ranging from between about 180 pF/um$^2$ to about 320 pF/um$^2$. In some embodiments, the ruthenium-containing material comprises at least two of ruthenium, oxygen, and nitrogen. In some embodiments, the ruthenium containing materials comprises at least one of ruthenium-nitride and ruthenium-oxynitride. In some embodiments, the nanopore is part of a nanopore sequencing complex.

In another aspect of the present disclosure is a biochip comprising: (a) a semiconductor substrate having a plurality of wells at a density of at least 250 wells/mm$^2$; and (b) an electrode disposed in each of the plurality of wells, wherein the electrode is comprised of a ruthenium-containing material. In some embodiments, the ruthenium-containing material is characterized as having a double-layer capacitance ranging from between about 180 pF/um$^2$ to about 320 pF/um$^2$. In some embodiments, the ruthenium-containing material is characterized as having a surface composition ratio of (N+O)/Ru as measured by X-ray photoelectron spectroscopy ranging from between about 1.5 and about 3.5. In some embodiments, the surface composition ratio ranges from about 1.8 to about 3.0. In some embodiments, the surface composition ratio ranges from about 2 to about 2.5.

In some embodiments, wherein the ruthenium-containing material is characterized as having a nitrogen content of at least about 5% nitrogen but not more than about 15%. In some embodiments, the biochip further comprises a hydrophobic coating disposed on a surface of each individual the electrode. In some embodiments, the biochip further comprises a cover disposed over the biochip. In some embodiments, the cover comprises at least one fluid inlet to facilitate delivery of one or more fluids to the lipid coating.

In another aspect of the present disclosure is a kit comprising a biochip (e.g. a biochip comprised of (a) a semiconductor substrate having a plurality of wells at a density of at least 250 wells/mm2; and (b) an electrode disposed in each of the plurality of wells, wherein the electrode is comprised of a ruthenium-containing material) and a second component. In some embodiments, the second component is a lipid solution. In other embodiments, the second component is a buffer. In some embodiments, the second component includes components used to form nanopore sequencing complexes (e.g. pores, enzymes, templates, etc.).

In another aspect of the present disclosure is a method of preparing a biochip comprising: (a) obtaining a semiconductor substrate; (b) forming a plurality of wells in the semiconductor substrate at a density of at least 250 wells/mm$^2$; and (c) forming an electrode in each individual well of the plurality of wells, wherein the electrode is comprised of a ruthenium-containing material. In some embodiments, the ruthenium-containing material is characterized as having a double-layer capacitance ranging from between about 180 pF/um$^2$ to about 320 pF/um$^2$. In some embodiments, the ruthenium-containing material is characterized as having a surface composition ratio of (N+O)/Ru as measured by X-ray photoelectron spectroscopy ranging from between about 1.5 and about 3.5. In some embodiments, the surface composition ratio ranges from about 1.8 to about 3.0. In some embodiments, the surface composition ratio ranges from about 2 to about 2.5. In some embodiments, the ruthenium-containing material is characterized as having a nitrogen content of at least about 5% nitrogen but not more than about 15%. In some embodiments, the method further comprises coating a surface of the electrode with a hydrophobic material.

In another aspect of the present disclosure is an assembly comprising: (i) a reservoir, (ii) a biochip (e.g. a biochip comprised of (a) a semiconductor substrate having a plurality of wells at a density of at least 250 wells/mm2; and (b) an electrode disposed in each of the plurality of wells, wherein the electrode is comprised of a ruthenium-containing material), and (iii) a counter electrode disposed on a biochip facing surface of the reservoir. In some embodiments, the counter electrode is printed on the biochip facing surface. Reservoirs, counter electrodes, and other assembly components are described in U.S. Pat. No. 9,658,190, the disclosure of which is hereby incorporated by reference herein in its entirety. Yet additional components for inclusion with an assembly are disclosed in United States Patent Application Publication Nos. 2017/0350859 and 2017/0326550, the disclosures of which are hereby incorporated by reference herein in their entireties.

Applicants have surprising discovered that ruthenium-containing materials having improved double layer capacitance enable a reduction in signal decay rates, ultimately allowing for improved resolution of signals when different types of tags are held inside the barrel of a nanopore.

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1A:
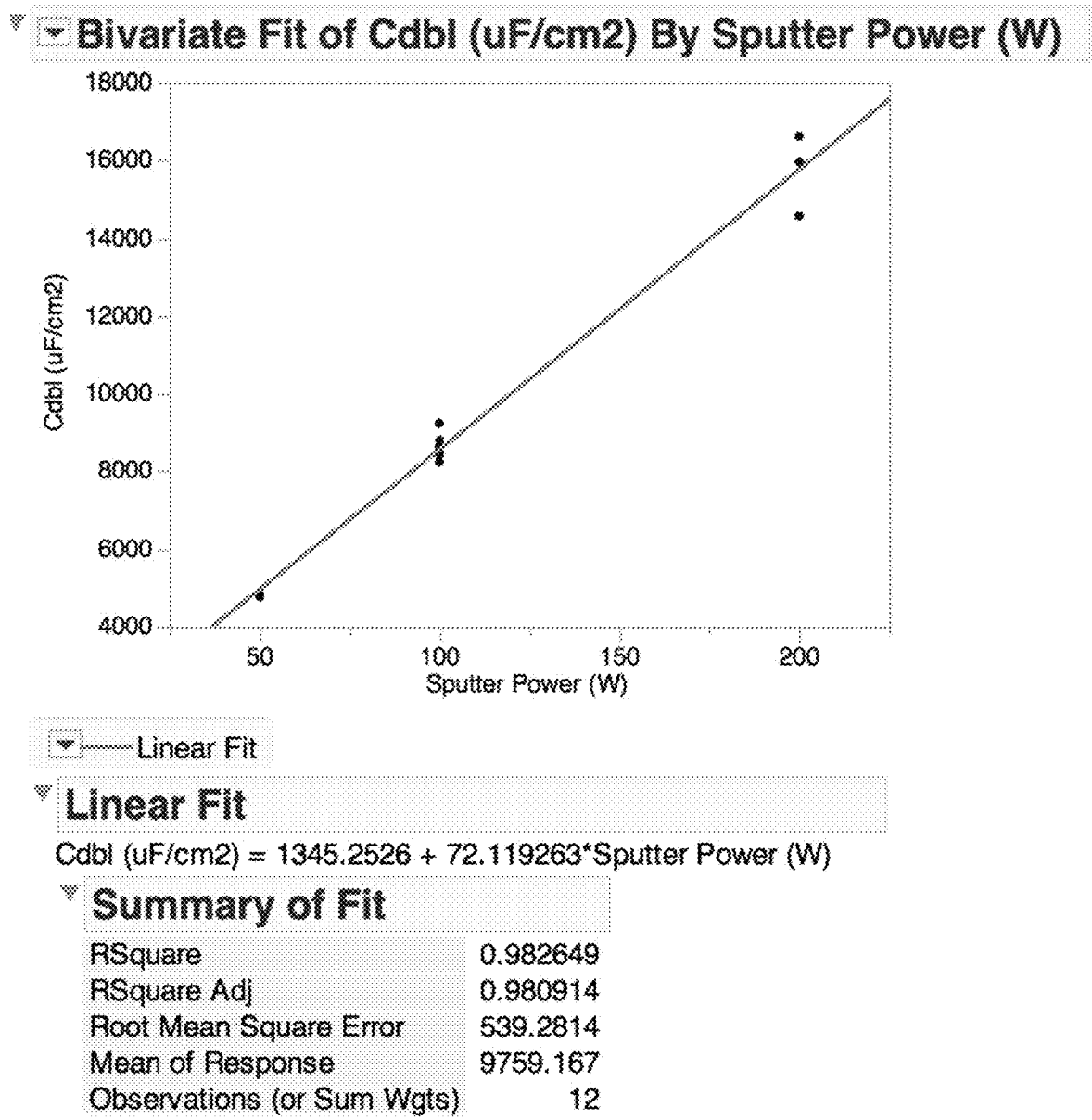
FIG. 1A illustrates the effect of sputter power on double layer capacitance.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of." "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "double layer capacitance" refers to the storage of electrical energy by means of the electrical double layer effect. This electrical phenomenon appears at the interface between a conductive electrode and an adjacent liquid electrolyte. At this boundary, two layers of ions with opposing polarity form if a voltage is applied. The two layers of ions are separated by a single layer of solvent molecules that adheres to the surface of the electrode and acts like a dielectric in a conventional capacitor.

As used herein, the term "introduction" means an addition or change in the concentration of a gas (or mixture of gases). A gas may be introduced by any means known in the art. For example, an additional quantity of a reactive gas could be added to the sputter chamber or to an inert gas stream by increasing the flow of that specific reactive gas (or mixture of gases) into the sputter chamber or gas stream (where, for example, the quantity of gas added can be determined by monitoring an attached flow meter or other mass flow controller).

As used herein, the term "sputtering chamber" may refer to the entire sputter chamber, a portion thereof, or an area surrounding a particular area of the sputter target.

As used herein, the term "nanopore" as refers to a pore, channel or passage formed or otherwise provided in a membrane. A nanopore can be defined by a molecule (e.g., protein) in a membrane. A membrane can be an organic membrane, such as a lipid bilayer, or a synthetic membrane, such as a membrane formed of a polymeric material. The nanopore may be disposed adjacent or in proximity to a sensing circuit, such as, for example, a complementary metal-oxide semiconductor (CMOS) or field effect transistor (FET) circuit. A nanopore may have a characteristic width or diameter on the order of 0.1 nanometers (nm) to about 1000 nm. Some nanopores are proteins. Alpha hemolysin is an example of a protein nanopore.

As used herein, the term "nanopore sequencing complex" refers to a nanopore linked or coupled to an enzyme, e.g., a polymerase, which in turn is associated with a polymer, e.g., a polynucleotide template. The nanopore sequencing complex is positioned in a membrane, e.g., a lipid bilayer, where it functions to identify polymer components, e.g., nucleotides or amino acids.

As used herein, the term "nanopore sequencing" or "nanopore-based sequencing" refers to a method that determines the sequence of a polynucleotide with the aid of a nanopore. In some embodiments, the sequence of the polynucleotide is determined in a template-dependent manner. The methods disclosed herein are not limited to any nanopore sequencing method, system, or device.

As used herein, the term "nucleic acid" refers to a molecule comprising one or more nucleic acid subunits. A nucleic acid can include one or more subunits (bases) selected from adenosine (A), cytosine (C), guanine (G), thymine (T) and uracil (U). Derivatives of these bases are exemplified in PCR Systems, Reagents and Consumables (Perkin Elmer Catalogue 1996-1997, Roche Molecular Systems, Inc., Branchburg, N.J., USA), which is entirely incorporated herein by reference. In some examples, a nucleic acid is deoxyribonucleic acid (DNA) or ribonucleic acid (RNA), or derivatives thereof. A nucleic acid may be single-stranded or double stranded. A nucleic acid can include any nucleic acid molecule, including, without limitation, DNA, RNA and hybrids or variants thereof.

As used herein, the term "sequencing" refers to the determination of the order and position of bases in a nucleic acid.

As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

As used herein, the term "tagged nucleotide" refers to a nucleotide having a tag attached at its terminal phosphate.

Applicants have developed an improved nanosequencing device including an electrode having unexpectedly superior double layer capacitance as compared with prior art electrodes, allowing for comparatively faster signal decay. These and other embodiments are disclosed herein.

Ruthenium-Containing Materials

In one aspect of the present disclosure are ruthenium-containing materials. In some embodiments, the ruthenium-containing materials comprise at least two of ruthenium, nitrogen, and oxygen. In some embodiments, the ruthenium-containing materials include ruthenium oxides, ruthenium nitrides, ruthenium oxynitrides, etc. and any complex or mixture thereof (e.g. a complex comprising ruthenium nitride and ruthenium oxynitride; or a mixture comprising ruthenium nitride and ruthenium oxynitride). In some embodiments, the ruthenium-containing materials may be used in electrodes. In some embodiments, the ruthenium-containing materials may be used as electrodes in chips or biochips comprising a plurality of wells, such as a plurality of individually addressable wells. In some embodiments, the ruthenium-containing materials may be incorporated into an electrode for use in a sequencing device, such as a nanopore sequencing device. As will be described in further detail herein, the presently disclosed ruthenium-containing materials have improved physical and/or chemical properties in comparison to other metal nitrides, such as titanium nitride, e.g. the ruthenium-containing materials provide increased double layer capacitance as compared with titanium nitride materials and also allow for comparatively enhanced signal decay rates.

In some embodiments, the ruthenium-containing materials are prepared by depositing the ruthenium-containing materials onto a substrate. As suitable deposition system may be utilized including, but not limited to, sputter deposition, plasma vapor deposition, chemical vapor deposition, intermediate frequency reactive sputtering, DC sputtering, and magnetic sputtering. Sputtering is widely used for depositing thin films of material onto substrates. Generally, such a process involves ion bombarding a planar or rotatable plate of the material to be sputtered ("the target") in an ionized gas atmosphere. Gas ions out of a plasma are accelerated towards the target consisting of the material to be deposited. Material is detached ("sputtered") from the target and afterwards deposited on a substrate in the vicinity. The process is realized in a closed chamber, which is pumped down to a vacuum base pressure before deposition starts. The vacuum is maintained during the process to cause particles of the target material to be dislodged and deposited as a thin film on the substrate being coated.

In some embodiments, the material to be sputtered onto the substrate is present as a coating on a target plate (the plate itself can be a rotating target plate or a planar target plate). In other embodiments, the entire target may be comprised of the material to be sputtered onto the substrate. Any material may be used for this purpose, including pure and mixed metals.

A suitable sputter system includes (i) a chamber configured for sputtering a planar or rotating target (e.g. a ruthenium target); (ii) one or more gas manifolds (or mixed gas manifolds) in fluidic communication with the chamber (e.g. a first gas manifold for the introduction of nitrogen, and a second gas manifold for the introduction of an inert gas, such as argon); and (iii) reactive gas and inert gas sources in fluidic communication with the mixed gas manifolds. In some embodiments, the reactive gas is introduced into a portion of the chamber by the first gas manifold. In some embodiments the reactive gas is nitrogen. In some embodiments, the inert gas is argon. In some embodiments, a ratio of introduced reactive gas to introduced inert gas ranges from about 9:1 to about 1:1. In some embodiments, the reactive gas is added to the entire atmosphere within the sputter chamber. In other embodiments, the reactive gas is introduced over a specified area of the sputter chamber or to an area surrounding a particular portion of the target.

In some embodiments, a process of depositing the ruthenium-containing material onto a substrate comprises, as a first step, introducing the substrate and target (e.g. a ruthenium target) into the sputter chamber. In some embodiments, the substrate is a metal, e.g. aluminum. In other embodiments, the substrate is a pre-existing thin film, such as thin film that was deposited onto a metal substrate (e.g. a titanium film). In some embodiments, the pre-existing thin film serves as a seed layer for the growth of the ruthenium-containing material. In some embodiments, a pre-existing thin film may include lithium or a lithium-containing material.

Figure 1B:
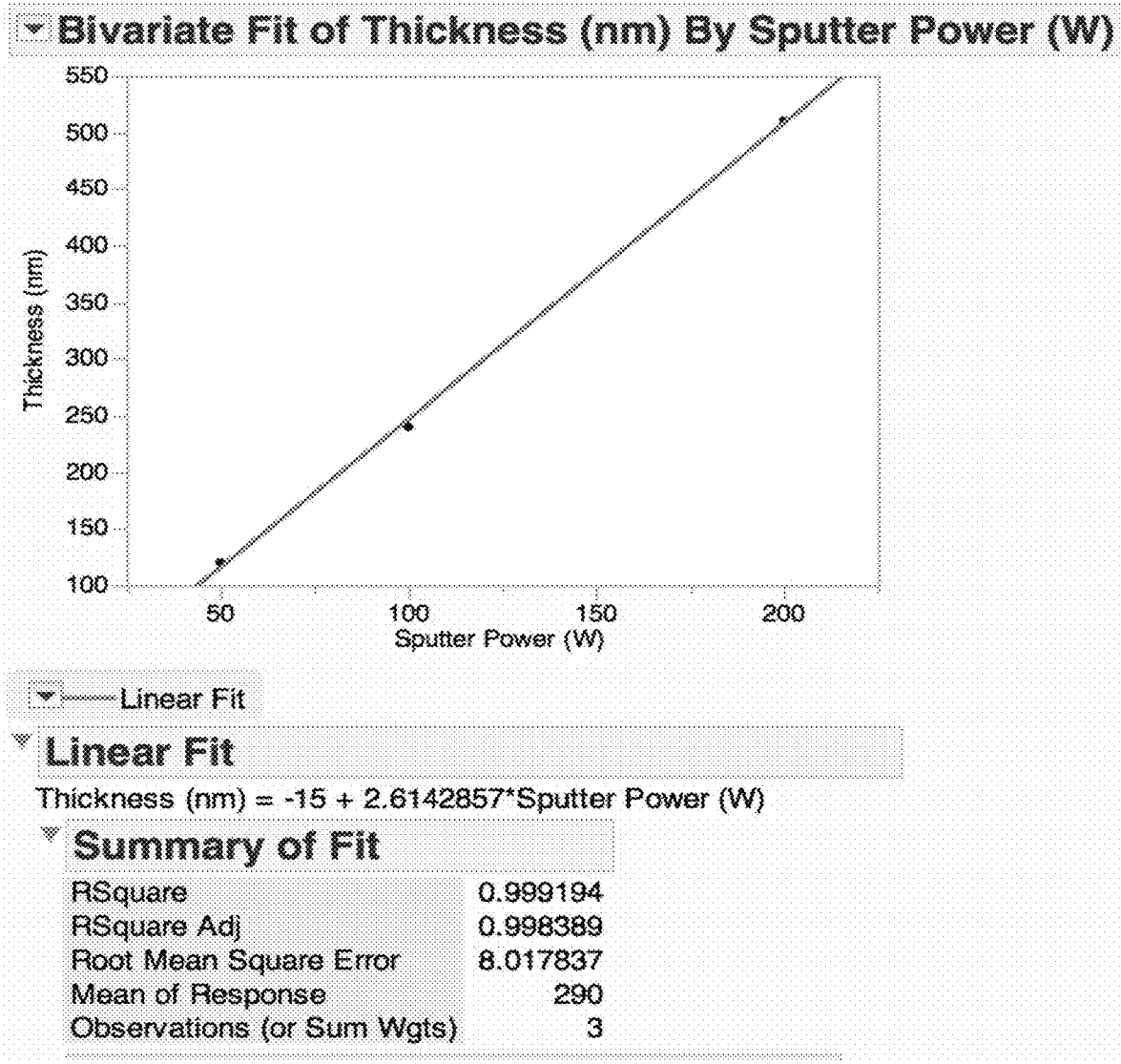
FIG. 1B illustrates the effect of sputter power on deposited film thickness.
Figure 1C:
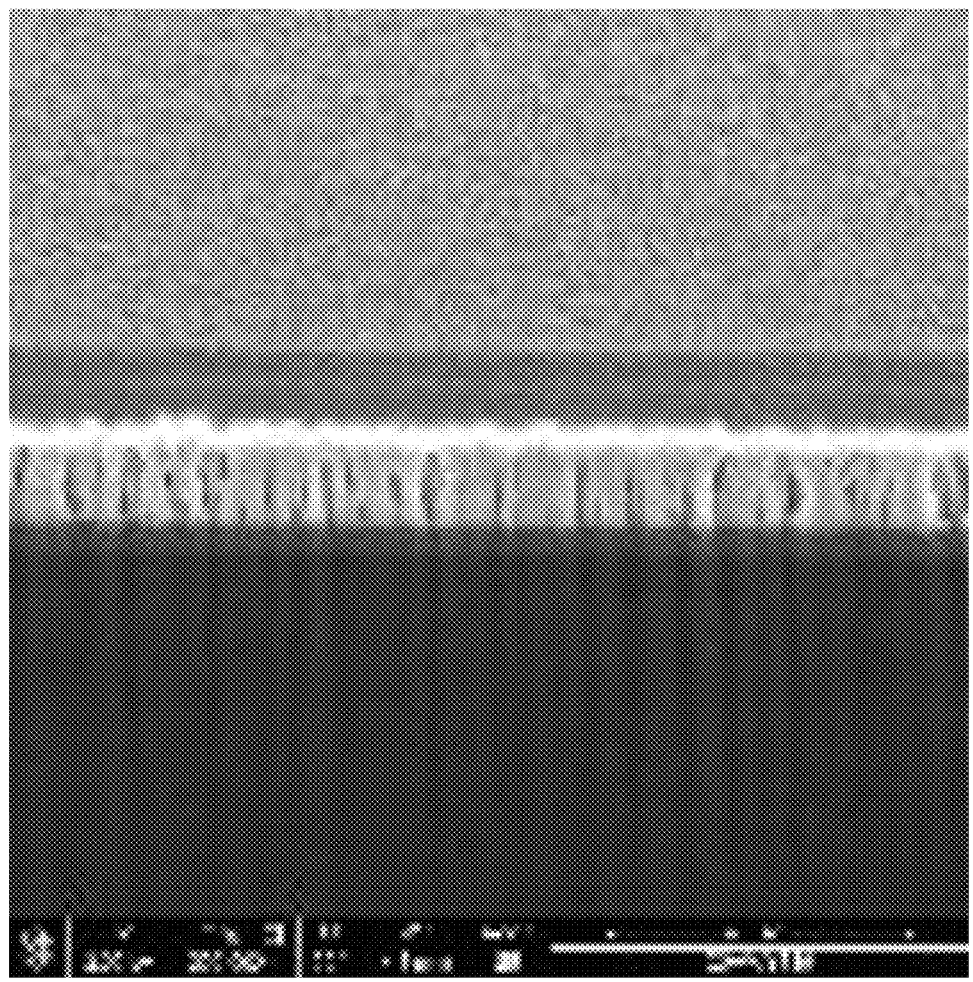
FIG. 1C provides a cross sectional scanning electron microscopy image of a ruthenium-containing film sputtered at 50 W.
Figure 1D:
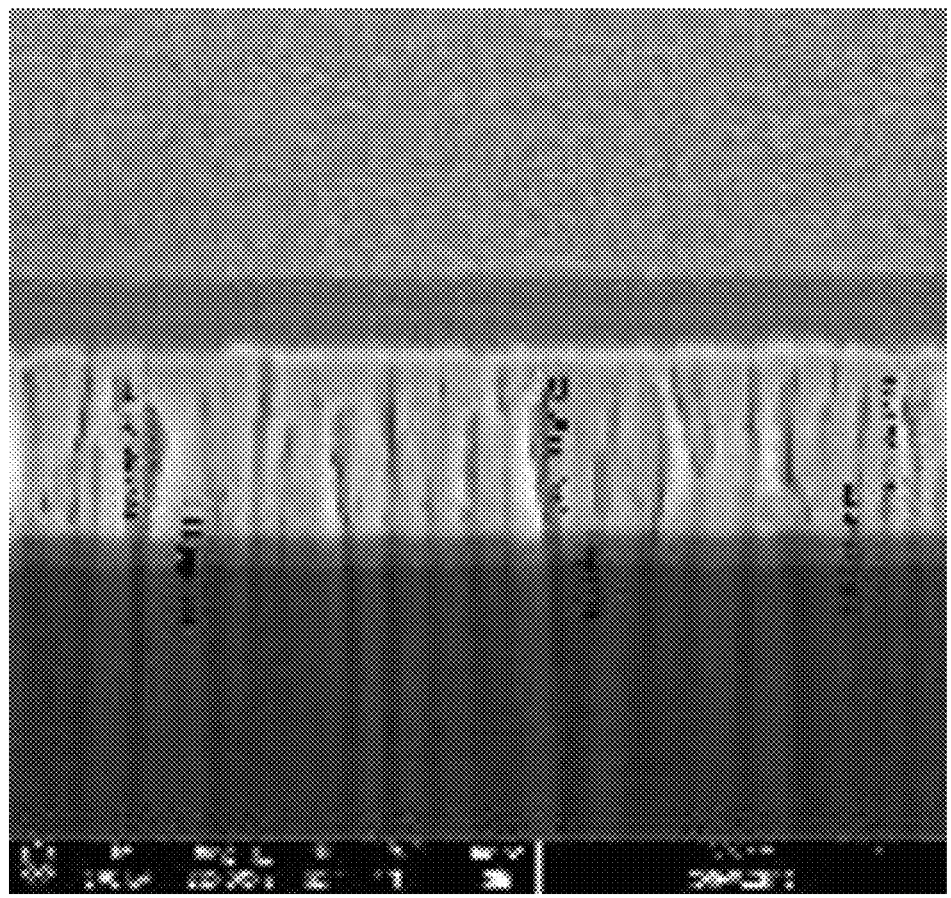
FIG. 1D provides a cross sectional scanning electron microscopy image of a ruthenium-containing film sputtered at 100 W.
Figure 1E:
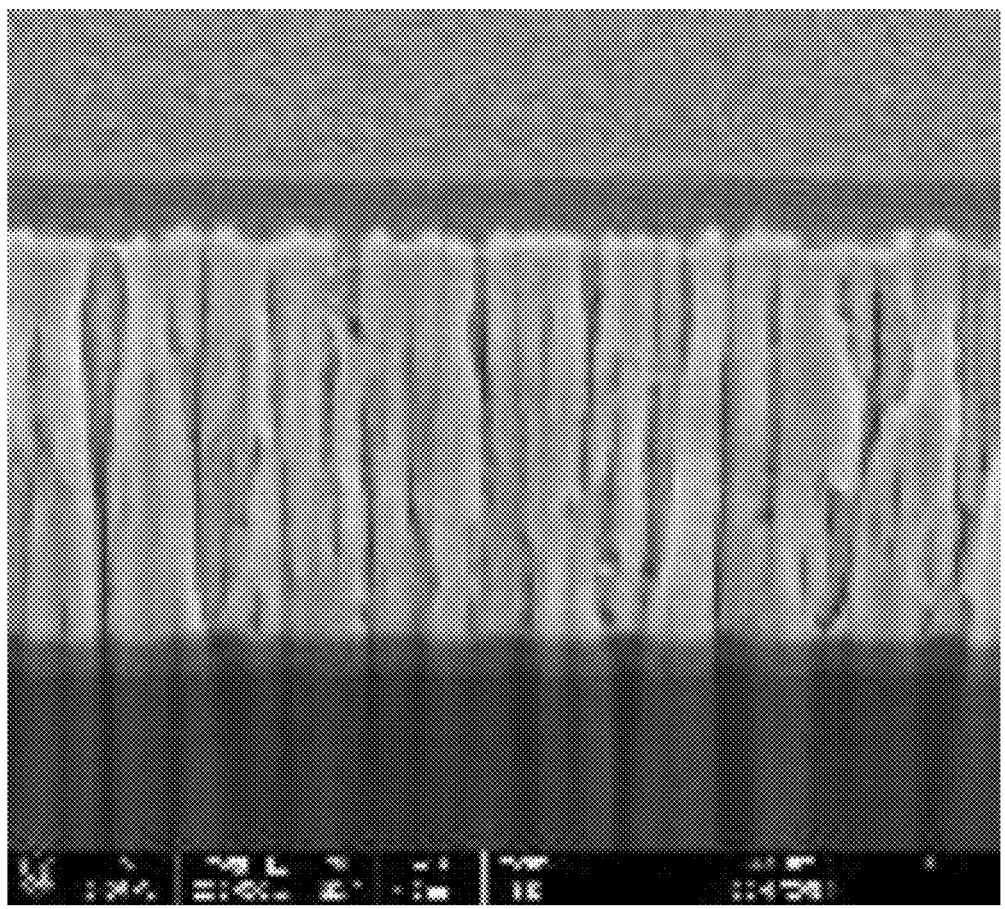
FIG. 1E provides a cross sectional scanning electron microscopy image of a ruthenium-containing film sputtered at 200 W.

In some embodiments, the power supplied during deposition ranges from between 50 watts to about 250 watts. In other embodiments, the power supplied during deposition ranges from between 50 watts to about 200 watts. In yet other embodiments, the power supplied during deposition ranges from between 100 watts to about 200 watts. In some embodiments, Applicants have discovered that the double layer capacitance of ruthenium-containing films, such as films of ruthenium nitride, increases linearly as sputter power is increased (see FIG. 1A). For example, the double layer capacitance increased from 4500 uF/cm2 at 50 watts of sputter power to 15000 uF/cm$^2$ at 200 watts of sputter power. In some embodiments, Applicants have discovered that the thickness of ruthenium-containing films, such as films of ruthenium nitride, increases linearly as sputter power is increased (see FIG. 1B). FIGS. 1C, 1D, and 1E further illustrate that as the sputter power is increased (for example, from 50 watts (FIG. 1C) to 100 watts (FIG. 1D) and then 200 watts (FIG. 1E)), the thickness of the ruthenium-containing film increased. It is believed that there is no degradation in double layer capacitance when thicker films (as compared to thinner films) are deposited.

Figure 1F:
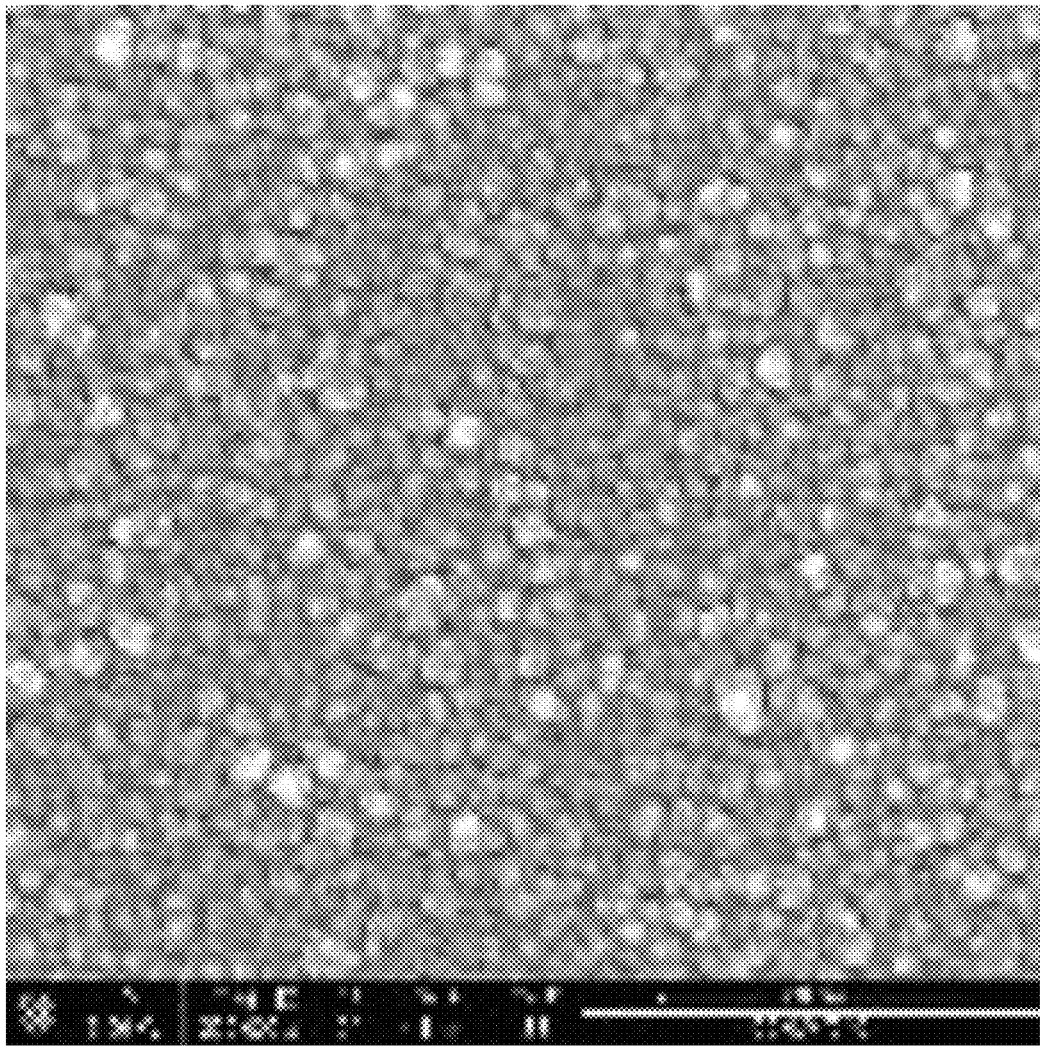
FIG. 1F provides a top down scanning electron microscopy image of a ruthenium-containing film sputtered at 50 W.
Figure 1G:
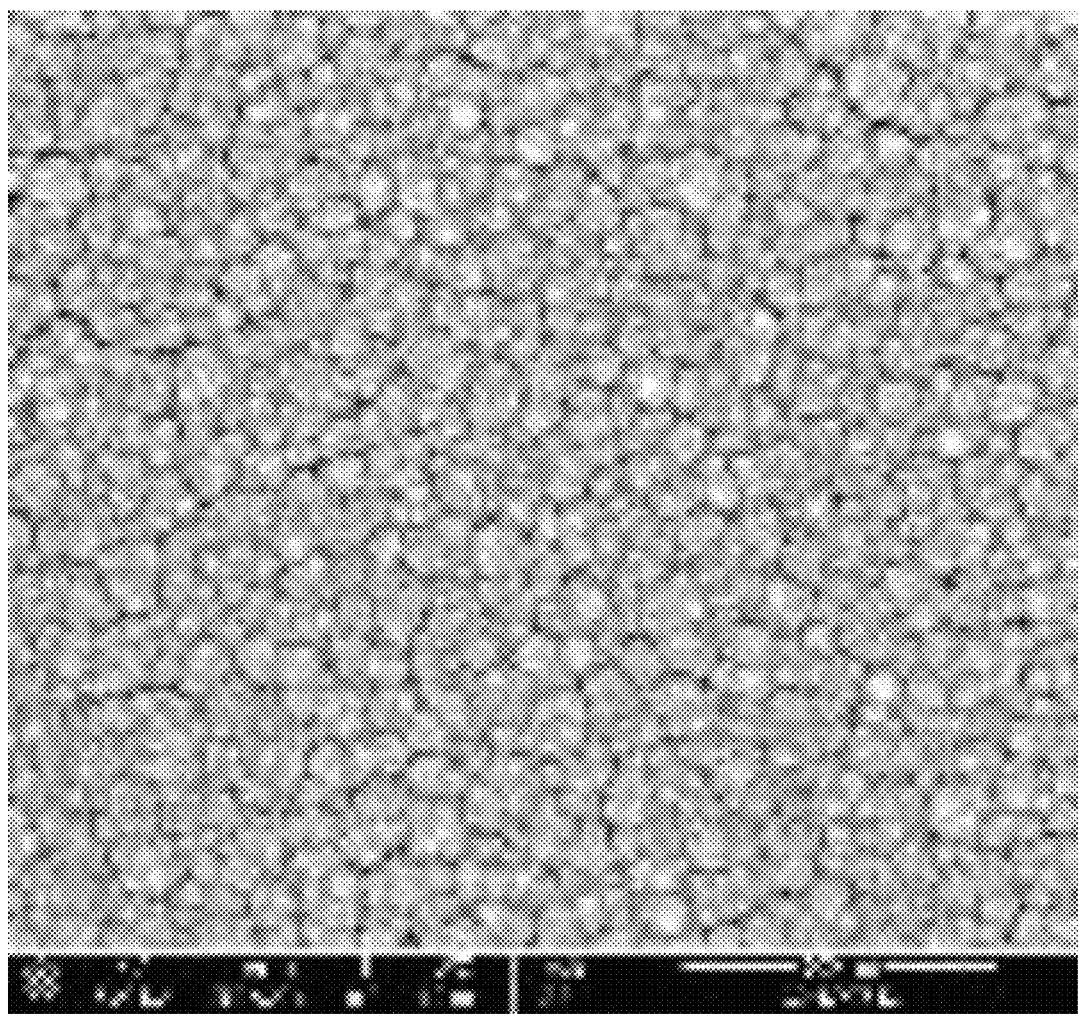
FIG. 1G provides a top down scanning electron microscopy image of a ruthenium-containing film sputtered at 100 W.
Figure 1H:
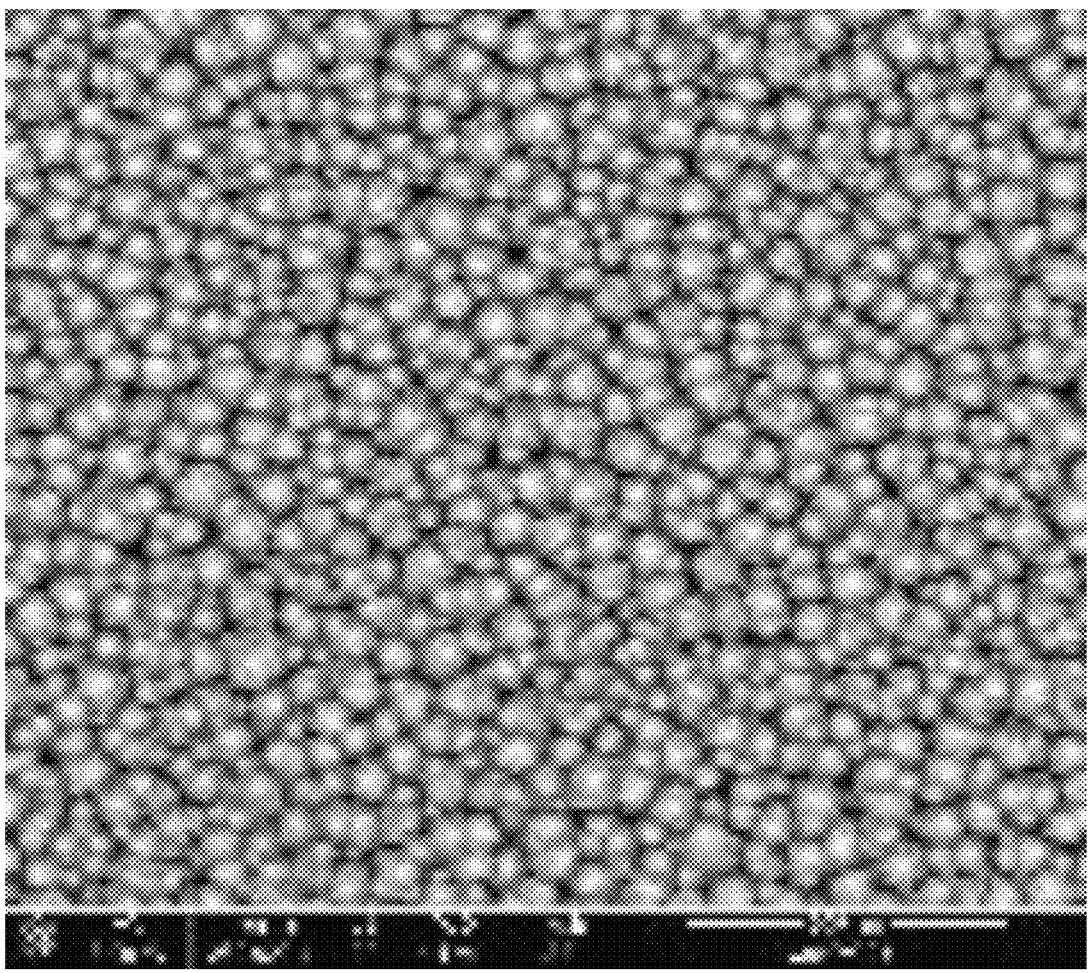
FIG. 1H provides a top down scanning electron microscopy image of a ruthenium-containing film sputtered at 200 W.

In addition, Applicants have discovered that as sputter power is increased (for example, from 50 watts (FIG. 1F) to 100 watts (FIG. 1G) and then to 200 watts (FIG. 1H)) that the structure of the film changes, e.g. the structure became more columnar in nature as sputter power was increased (holding constant the total pressure of the sputter chamber and the partial pressures of introduced reactive and inert gases). In some embodiments, it is believed that the dendritic structure is generally less compact and less oriented than a columnar structure.

In some embodiments, deposition is performed in the presence of nitrogen. In some embodiments, nitrogen is introduced at a rate of between about 5 sccm and about 150 sccm. In other embodiments, nitrogen is introduced at a rate of between about 5 sccm and about 120 sccm. In yet other embodiments, nitrogen is introduced at a rate of between about 5 sccm and about 100 sccm. In further embodiments, nitrogen is introduced at a rate of between about 5 sccm and about 90 sccm. In other embodiments, nitrogen is introduced at a rate of between about 5 sccm and about 80 sccm. In other embodiments, nitrogen is introduced at a rate of between about 10 sccm and about 50 sccm. In other embodiments, nitrogen is introduced at a rate of between about 10 sccm and about 20 sccm. In other embodiments, nitrogen is introduced at a rate of between about 50 sccm and about 100 sccm. In other embodiments, nitrogen is introduced at a rate of between about 80 sccm and about 100 sccm. In yet other embodiments, nitrogen is introduced at a rate of about 90 sccm.

In some embodiments, an inert gas (e.g. argon) is introduced into the sputtering chamber. In some embodiments, the inert gas is introduced through the same manifold as the nitrogen (i.e. using a mixed gas manifold). In other embodiments, the inert gas is introduced through a separate manifold, i.e. a manifold separate and apart from the manifold used to introduce the nitrogen. In some embodiments, the inert gas is introduced at a rate of between about 1 and about 15 sccm. In other embodiments, the inert gas is introduced at a rate of between about 5 and about 10 sccm. In yet other embodiments, the inert gas is introduced at a rate of about 5 sccm. In further embodiments, the inert gas is introduced at a rate of about 10 sccm.

In some embodiments, the pressure within the sputter chamber is maintained between 5 mTorr and about 30 mTorr. In other embodiments, the pressure within the sputter chamber is maintained between 5 mTorr and about 25 mTorr. In other embodiments, the pressure within the sputter chamber is maintained between 10 mTorr and about 20 mTorr. In yet other embodiments, the pressure within the sputter chamber is maintained at about 10 mTorr. In yet other embodiments, the pressure within the sputter chamber is maintained at about 15 mTorr. In yet other embodiments, the pressure within the sputter chamber is maintained at about 20 mTorr.

In some embodiments, the temperature during sputtering is maintained from about 25° C. to about 150° C. In some embodiments, the temperature during sputtering is maintained from about 25° ° C. to about 100° C. In some embodiments, the temperature during sputtering is maintained from about 25° ° C. to about 80° C. In some embodiments, the temperature during sputtering is maintained from about 25° ° C. to about 60° C. In some embodiments, the temperature during sputtering is maintained from about 25° C. to about 50° C. In some embodiments, the temperature during sputtering is maintained from about 25° C. to about 40° C.

In some embodiments, the deposition comprises utilizes the following processing parameters: a total pressure ranging from about 2 mTorr to about 30 mTorr, a nitrogen flow rate ranging from between about 0 sccm to about 200 sccm, an argon flow rate ranging from between about 0 sccm and about 200 sccm, and a sputtering power ranging from between about 50 watts to about 300 watts; and sputtering at a temperature ranging from about 25° C. to about 150° ° C. In some embodiments, the deposition comprises utilizes the following processing parameters: a total pressure of 10 mTorr, a nitrogen flow rate of 20 sccm, and a sputtering power of 100 watts. In other embodiments, the deposition comprises utilizes the following processing parameters: a total pressure of 20 mTorr, a nitrogen flow rate of 20 sccm, and a sputtering power of 100 watts. In other embodiments, the deposition comprises utilizes the following processing parameters: a total pressure of 10 mTorr, a nitrogen flow rate of 90 sccm, and a sputtering power of 100 watts. In other embodiments, the deposition comprises utilizes the following processing parameters: a total pressure of 20 mTorr, a nitrogen flow rate of 90 sccm, and a sputtering power of 100 watts. In some embodiments, the deposition comprises utilizes the following processing parameters: a total pressure of 10 mTorr, a nitrogen flow rate of 20 sccm, and a sputtering power of 200 watts. In other embodiments, the deposition comprises utilizes the following processing parameters: a total pressure of 20 mTorr, a nitrogen flow rate of 20 sccm, and a sputtering power of 200 watts. In other embodiments, the deposition comprises utilizes the following processing parameters: a total pressure of 10 mTorr, a nitrogen flow rate of 90 sccm, and a sputtering power of 200 watts. In other embodiments, the deposition comprises utilizes the following processing parameters: a total pressure of 20 mTorr, a nitrogen flow rate of 90 sccm, and a sputtering power of 200 watts.

Figure 2A:
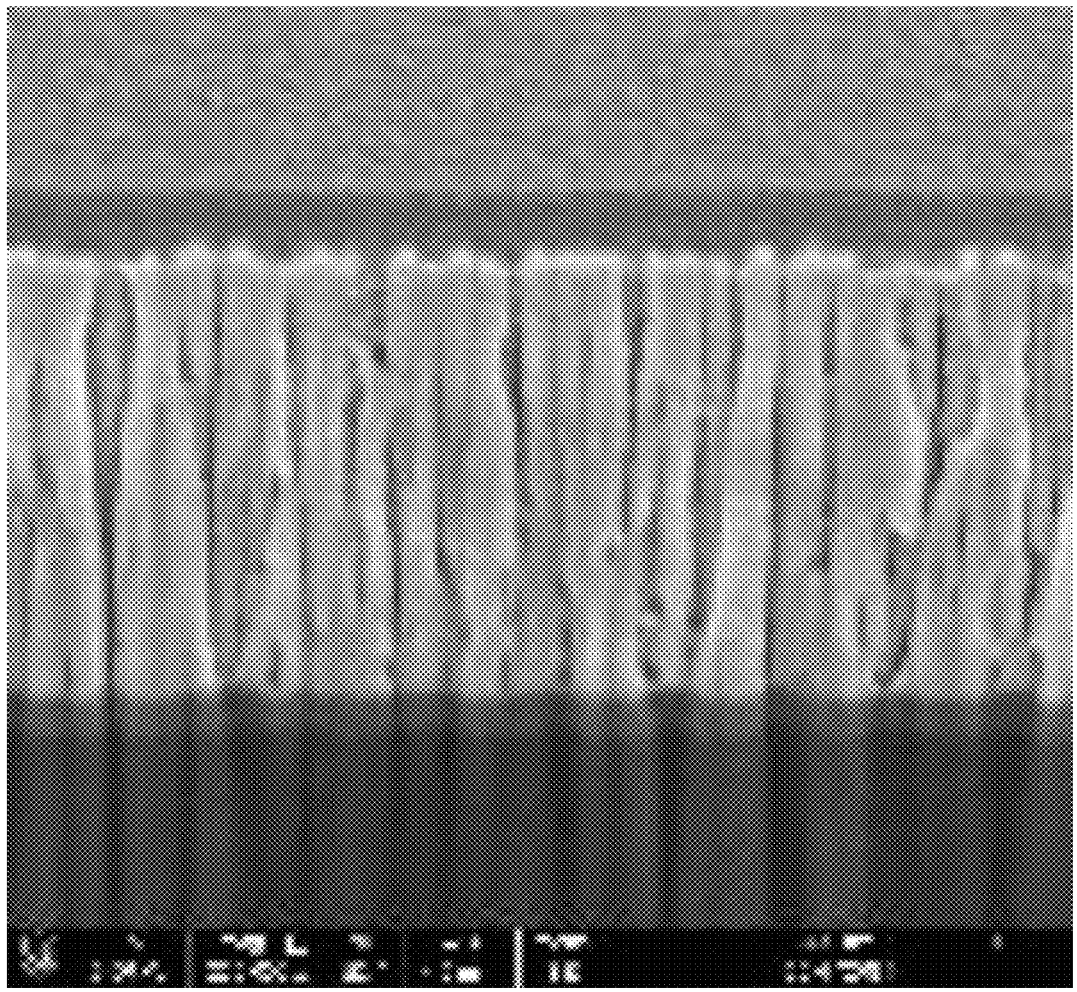
FIG. 2A provides a cross sectional scanning electron microscopy image of a ruthenium-containing film sputtered at 200 W, 10 mTorr, a flow rate of 10 sccm for argon, and a flow rate of 20 sccm for nitrogen.
Figure 2B:
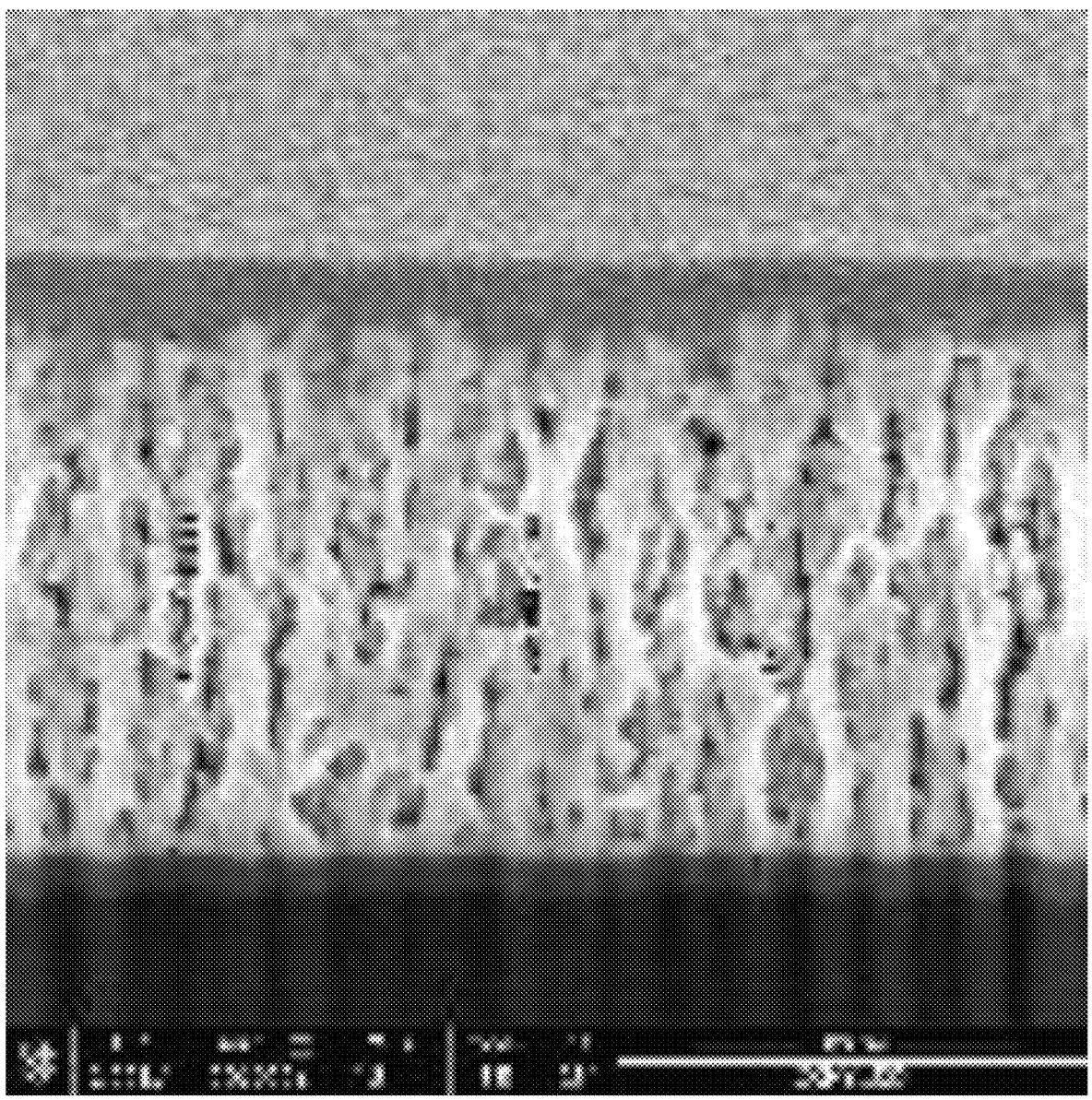
FIG. 2B provides a cross sectional scanning electron microscopy image of a ruthenium-containing film sputtered at 200 W, 10 mTorr, a flow rate of 10 sccm for argon, and a flow rate of 90 sccm for nitrogen.
Figure 2C:
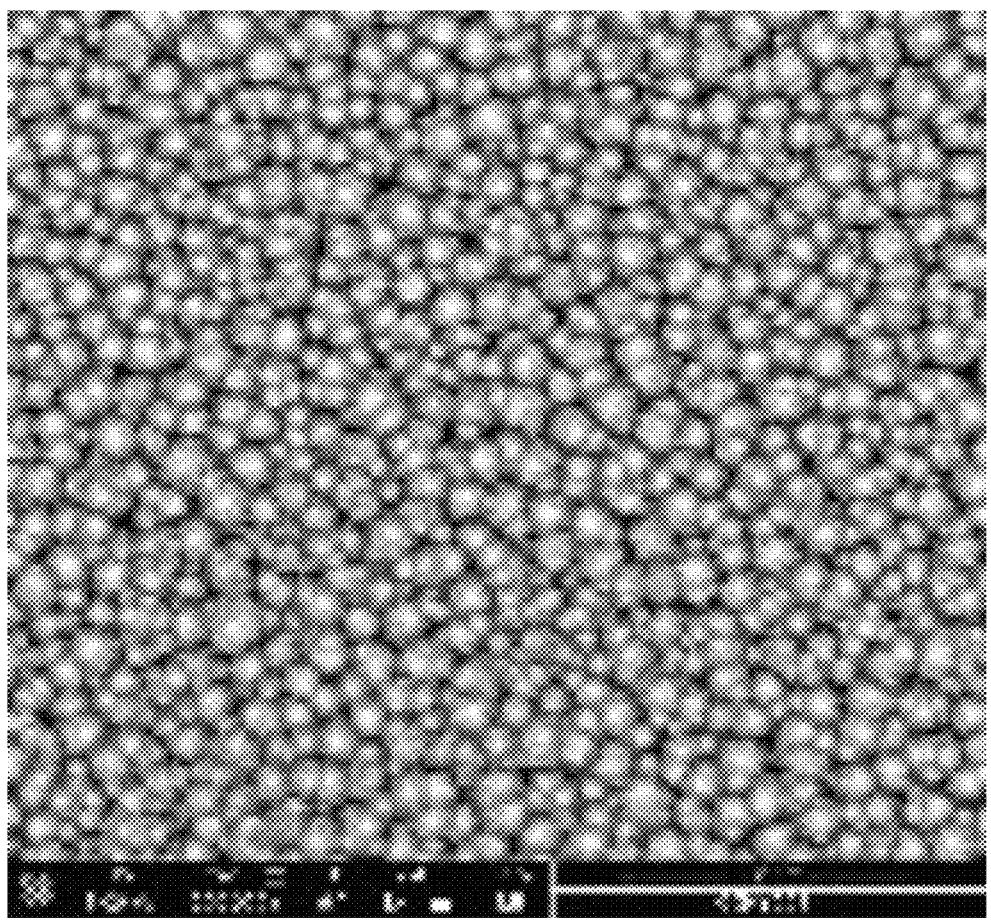
FIG. 2C provides a top down scanning electron microscopy image of a ruthenium-containing film sputtered at 200 W, 10 mTorr, a flow rate of 10 sccm for argon, and a flow rate of 20 sccm for nitrogen.
Figure 2D:
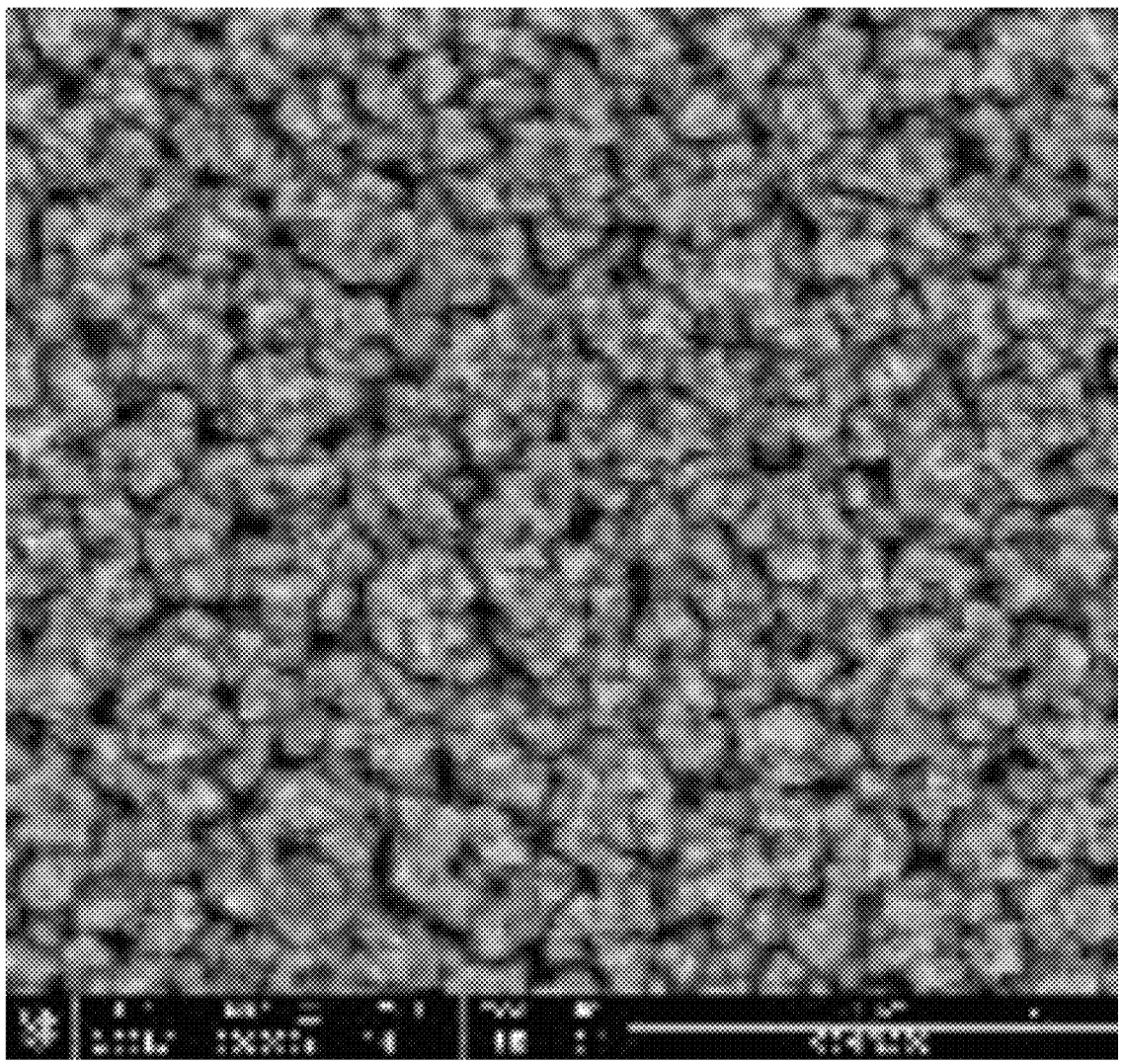
FIG. 2D provides a top down scanning electron microscopy image of a ruthenium-containing film sputtered at 200 W, 10 mTorr, a flow rate of 10 sccm for argon, and a flow rate of 90 sccm for nitrogen.

Applicants have unexpectedly discovered that as the partial pressure of introduced nitrogen increases relative to the partial pressure of introduced inert gas (e.g. argon), the structure of the formed film changes from a columnar structure to a dendritic structure. Applicants have also unexpectedly discovered that as the partial pressure of introduced nitrogen increases relative to the partial pressure of introduced inert gas, the porosity of the formed filmed increases. FIGS. 2A, 2B, 2C, and 2D illustrate the increase in porosity and the change from a columnar structure to a dendritic structure as the partial pressure of introduced nitrogen is increased relative to that of the inert gas (and where sputter power and the total pressure chamber within the sputter chamber are held constant). Specifically, FIGS. 2A and 2B comparatively illustrate the increase in porosity and the change from a columnar structure to a dendritic structure according to cross-sectional scanning electron microscopy. Likewise, FIGS. 2C and 2D comparatively illustrate the increase in porosity and again the change from a columnar structure to a dendritic structure according to top down scanning electron microscopy.

Figure 2E:
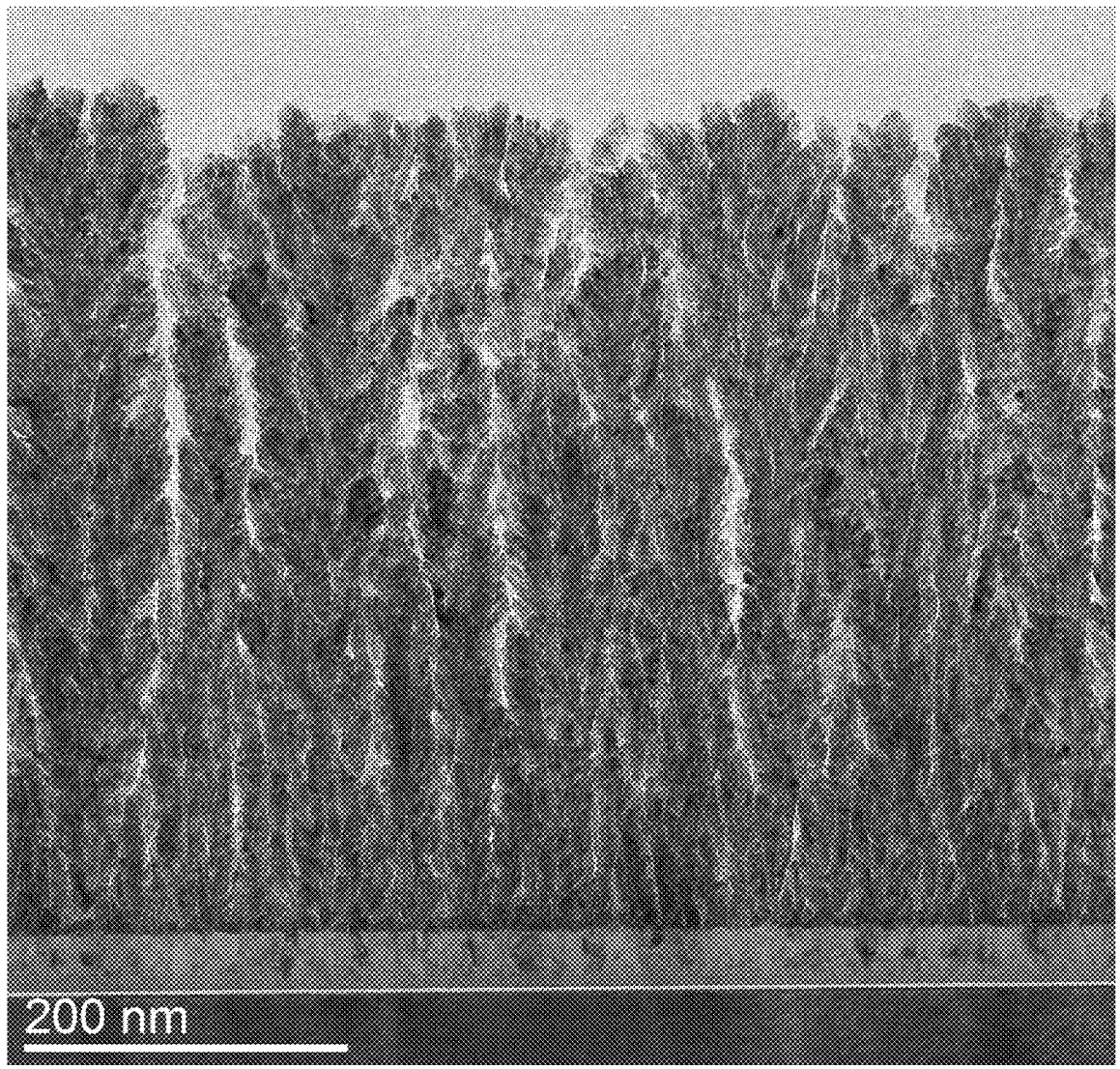
FIG. 2E provides a cross sectional scanning electron microscopy image of a ruthenium-containing film sputtered at 200 W, 10 mTorr, a flow rate of 10 sccm for argon, and a flow rate of 90 sccm for nitrogen.
Figure 2F:
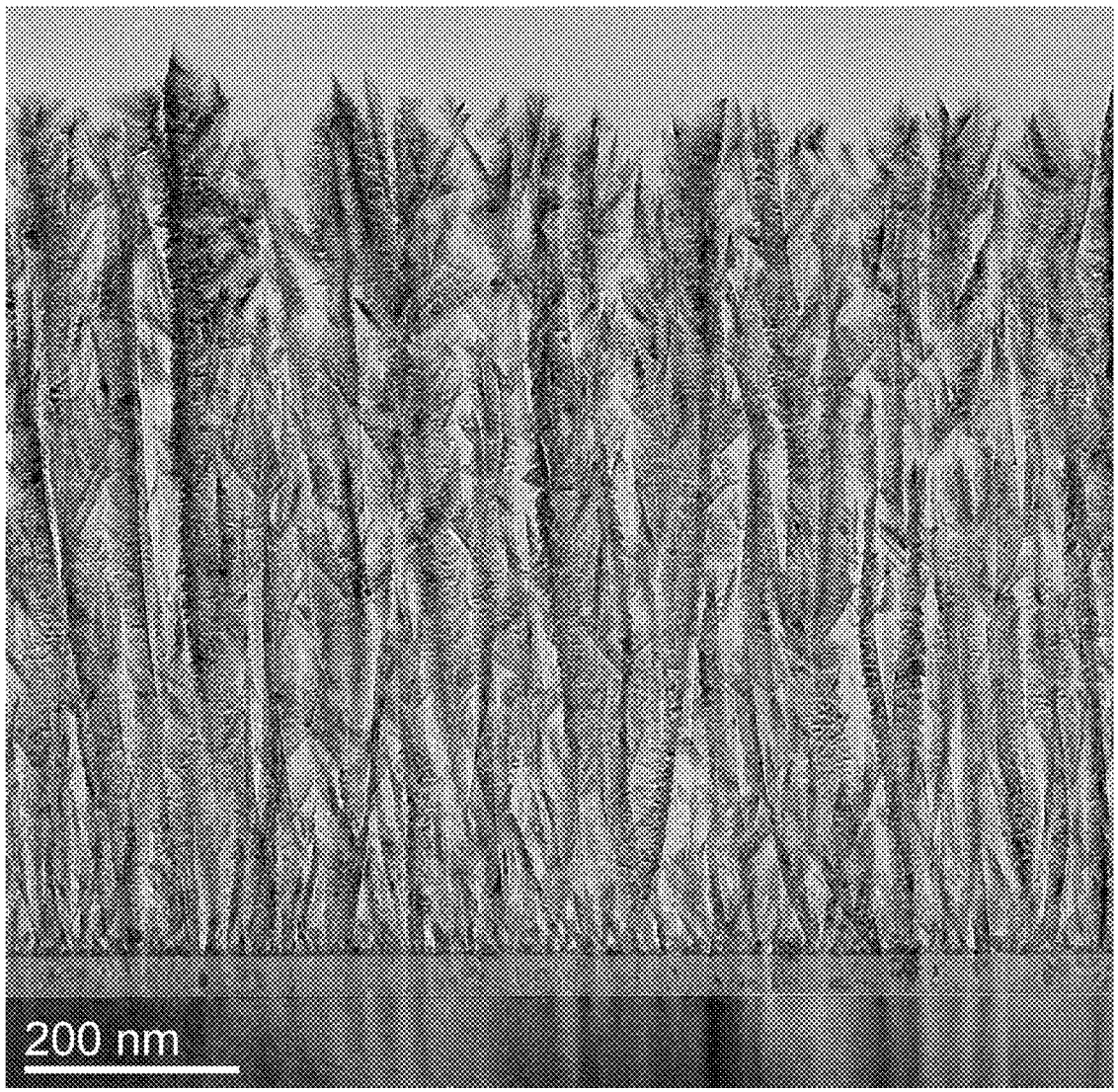
FIG. 2F provides a cross sectional scanning electron microscopy image of a ruthenium-containing film sputtered at 200 W, 10 mTorr, a flow rate of 10 sccm for argon, and a flow rate of 90 sccm for nitrogen.
Figure 2G:
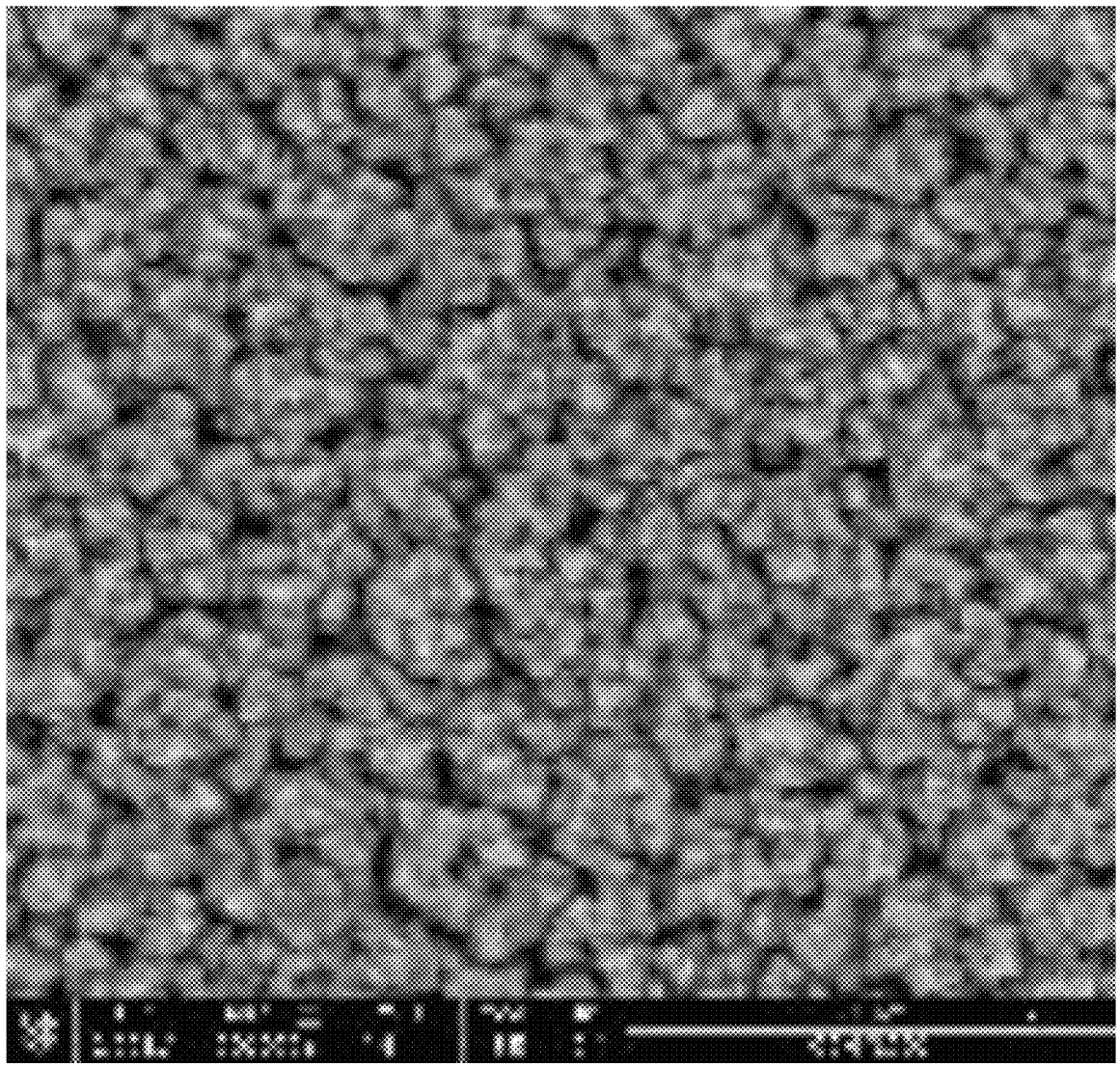
FIG. 2G provides a top down scanning electron microscopy image of a ruthenium-containing film sputtered at 200 W, 10 mTorr, a flow rate of 10 sccm for argon, and a flow rate of 20 sccm for nitrogen.
Figure 2H:
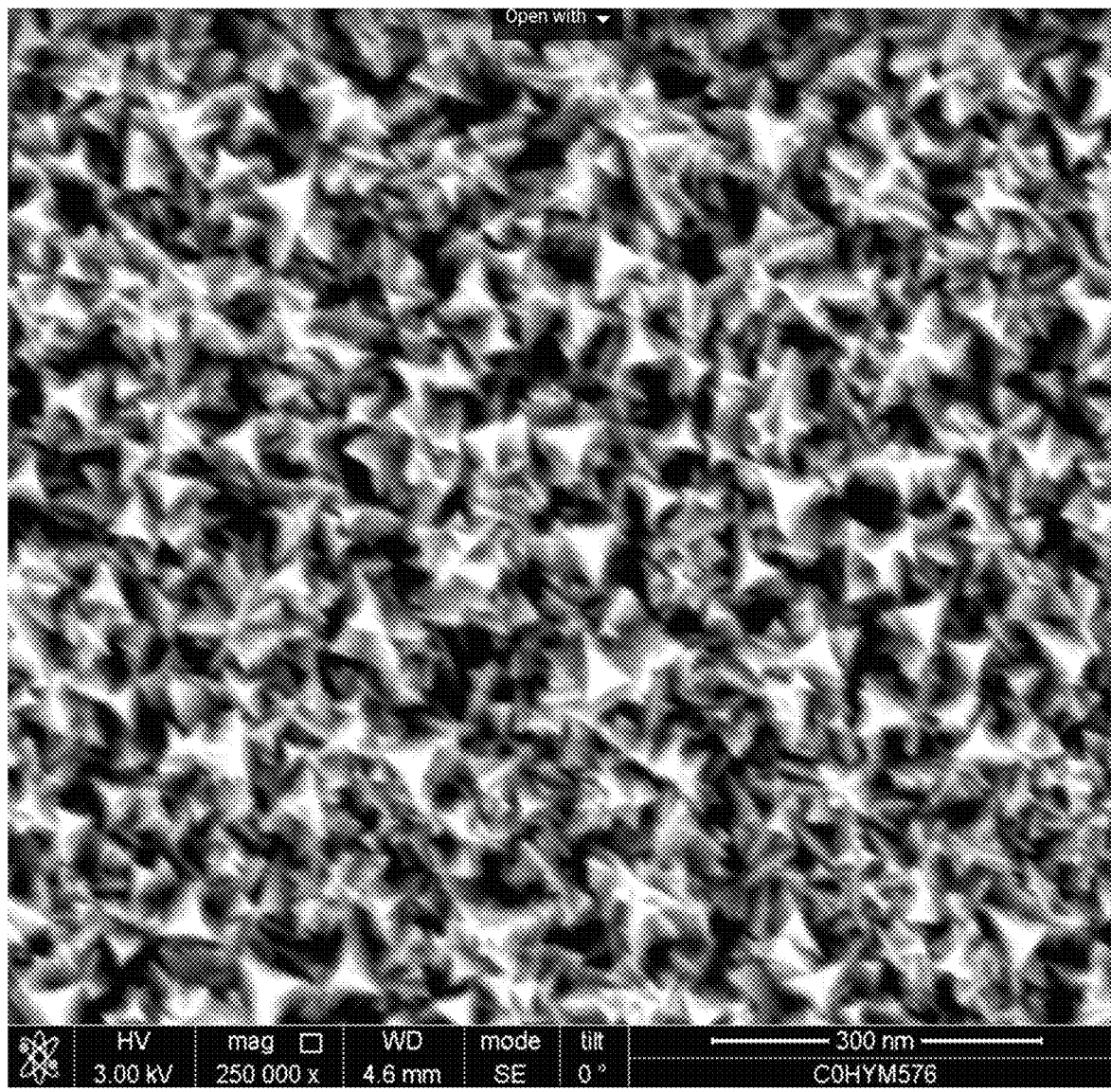
FIG. 2H provides a top down scanning electron microscopy image of a ruthenium-containing film sputtered at 200 W, 20 mTorr, a flow rate of 10 sccm for argon, and a flow rate of 90 sccm for nitrogen.

Additionally, Applicants have unexpectedly discovered that as total pressure of the sputter chamber was increased, e.g. from 10 mTorr to 20 mTorr, that the dendritic structure of the film further increases, with a concomitant increase in film porosity (see FIGS. 2E, 2F, 2G, and 2H). Without wishing to be bound by any particular theory, it is believed that the formation of ruthenium nitride from ruthenium and nitrogen is not an energetically favored process. In some embodiments, the higher partial pressure of nitrogen at 20 mTorr (versus at a lower total pressure, such as at 10 mTorr), favors the formation of ruthenium nitride. In some embodiments, it is believed that this allows for the formation of a more dendritic structure and/or one having higher porosity. For example, FIGS. 2E and 2F compare the cross sections of two films (based on scanning electron microscopy) where an increase in the dendritic nature of the structure is observed as the total pressure is increased from 10 mTorr to 20 mTorr. FIGS. 2G and 2H illustrate top down views of the same two films, again illustrating the increase in the dendritic nature of the structure of the film after the total pressure is increased.

Figure 3A:
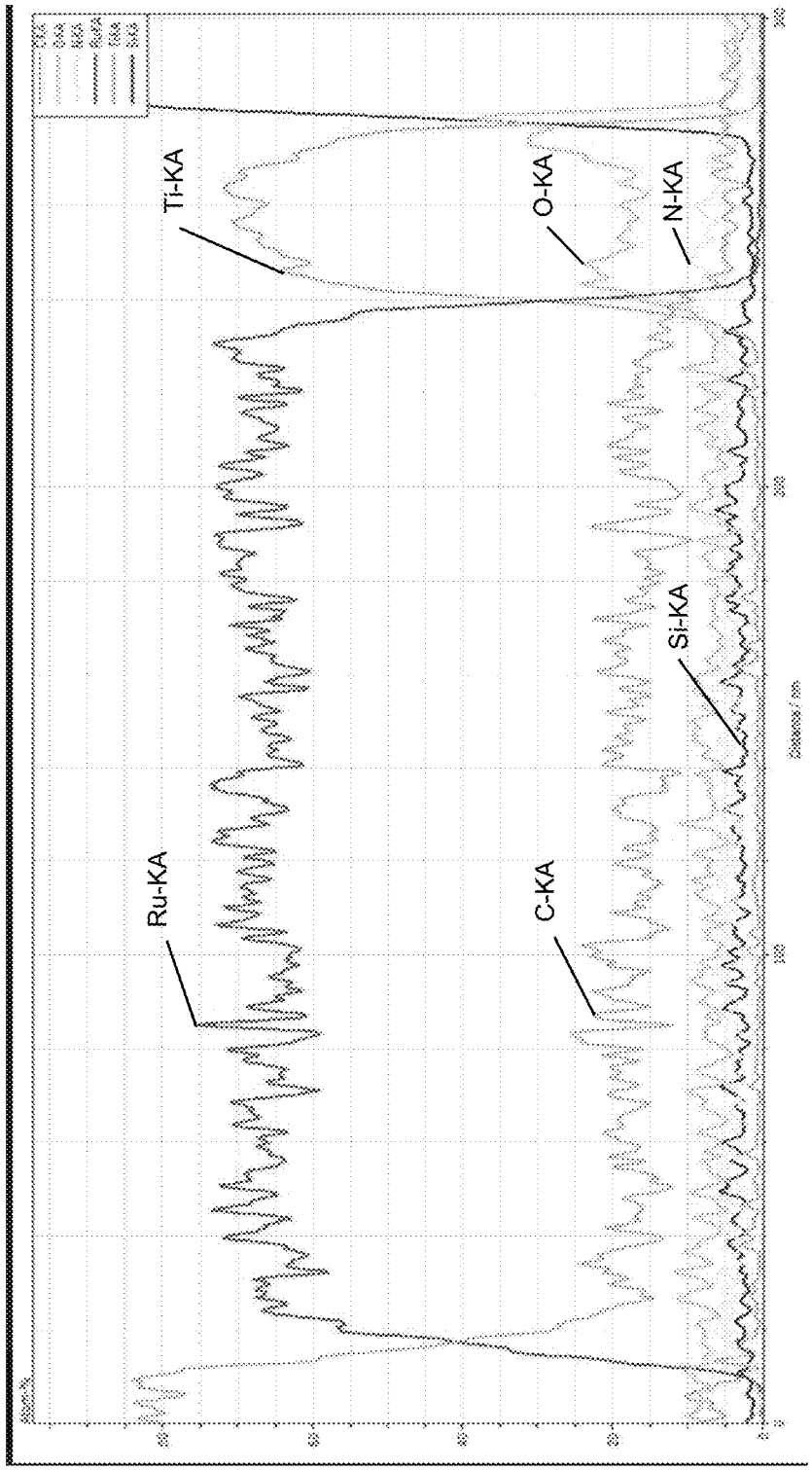
FIG. 3A sets forth energy dispersive x-ray spectroscopy results for a ruthenium-containing film sputtered at a flow rate of 10 sccm for argon and 20 sccm for argon. The data suggests that at 20 sccm (a low nitrogen flow rate), that the bulk of the generated film is predominantly ruthenium and the film comprises less than 5% nitrogen.
Figure 3B:
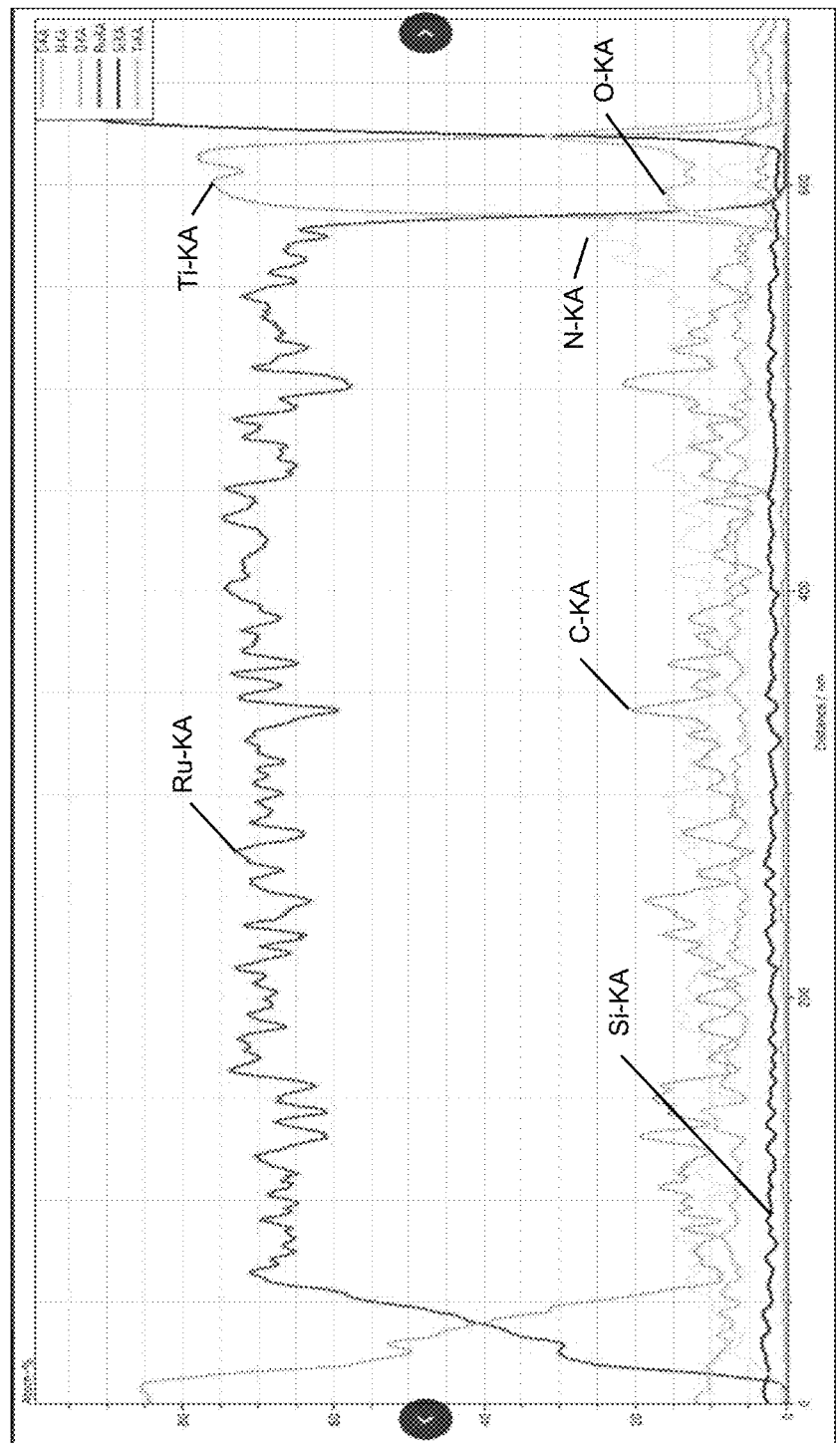
FIG. 3B sets forth energy dispersive x-ray spectroscopy results for a ruthenium-containing film sputtered at a flow rate of 10 sccm for argon and 90 sccm for argon. The data suggests that at 90 sccm (a high nitrogen flow rate), that the bulk of the generated film is predominantly ruthenium and the film comprises about 15% nitrogen.

In some embodiments, the deposited ruthenium-containing film comprises between about 1% to about 20% by weight of nitrogen. In other embodiments, the deposited ruthenium-containing film comprises between about 5% to about 15% by weight of nitrogen. In other embodiments, the deposited ruthenium-containing film comprises between about 10% to about 15% by weight of nitrogen. Applicants have discovered that at low nitrogen flow rates, e.g. a flow rate of 20 sccm, that the bulk of the deposited film comprises ruthenium, with less than 5% of the film constituting nitrogen (see FIG. 3A). However, as the flow rate of nitrogen increased, e.g. to a flow rate of 90 sccm, while the bulk of the deposited film still comprised ruthenium, it is believed that the amount of nitrogen increased to about 15% (see FIG. 3B).

In some embodiments, the double layer capacitance of the formed ruthenium-containing film ranges from between about 170 pF/um$^2$ to about 220 pF/um$^2$. In other embodiments, the double layer capacitance of the formed ruthenium-containing film ranges from between about 180 pF/um$^2$ to about 220 pF/um$^2$. In other embodiments, the double layer capacitance of the formed ruthenium-containing film ranges from between about 180 pF/um$^2$ to about 200 pF/um$^2$.

Figure 4A:
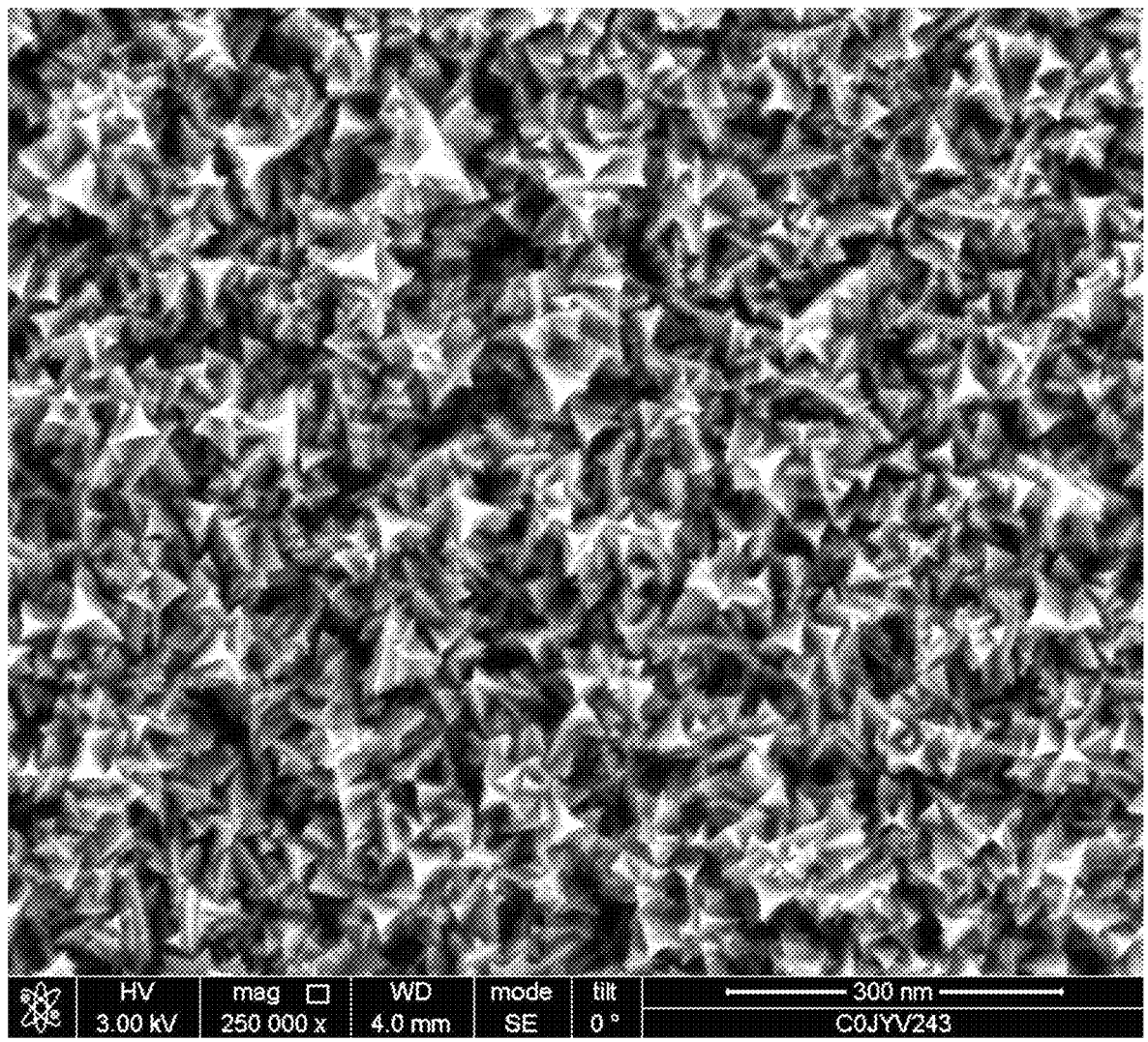
FIG. 4A provides a top down scanning electron microscopy image of a ruthenium-containing film sputter deposited at 200 W, room temperature, 20 mTorr, a flow rate of 10 sccm for argon, and a flow rate of 90 sccm for nitrogen, followed by a thermal treatment at 150° C.
Figure 4B:
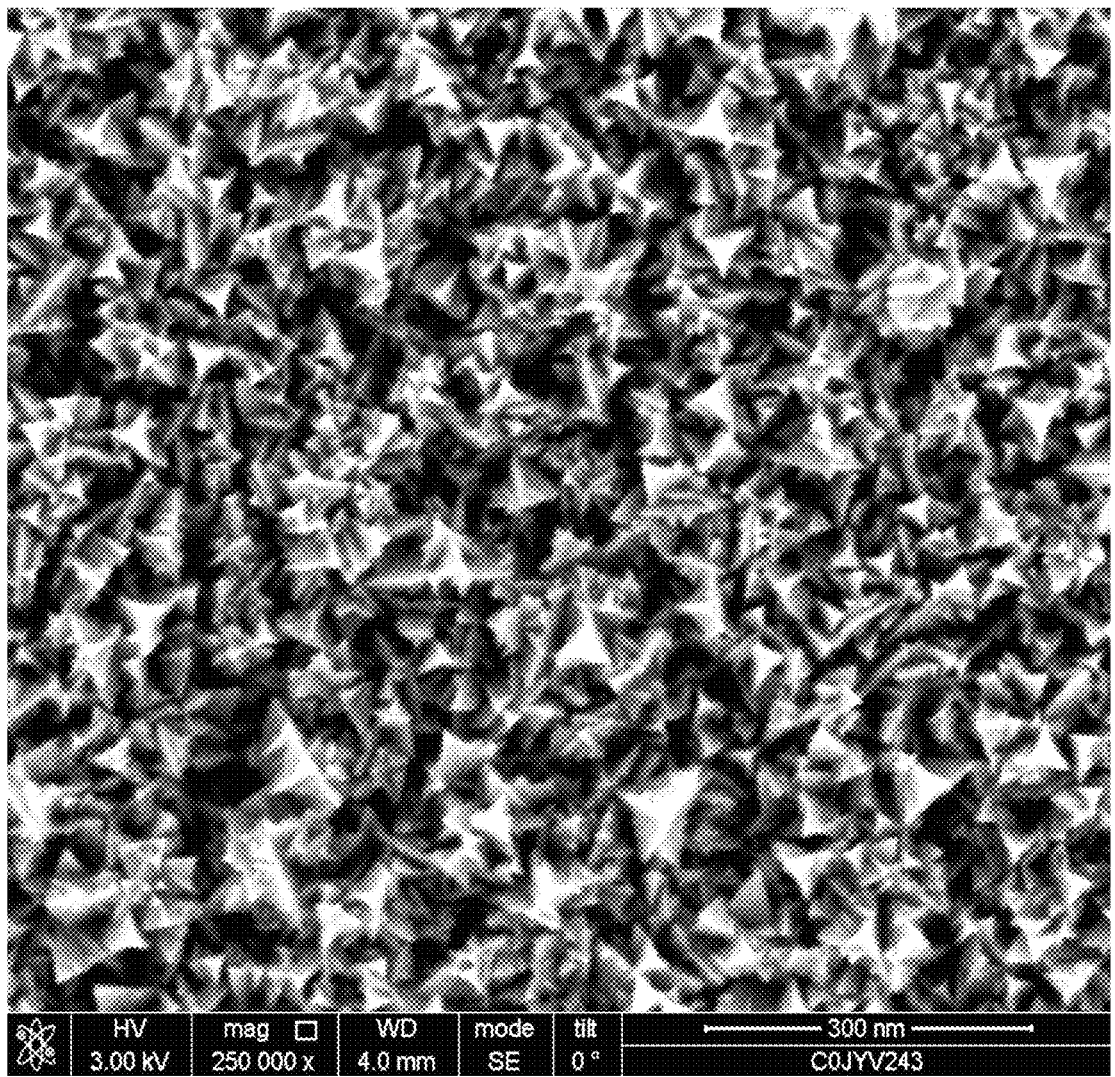
FIG. 4B provides a top down scanning electron microscopy image of a ruthenium-containing film sputter deposited at 200 W, room temperature, 20 mTorr, a flow rate of 10 sccm for argon, and a flow rate of 90 sccm for nitrogen, followed by a thermal treatment at 200° C.
Figure 4C:
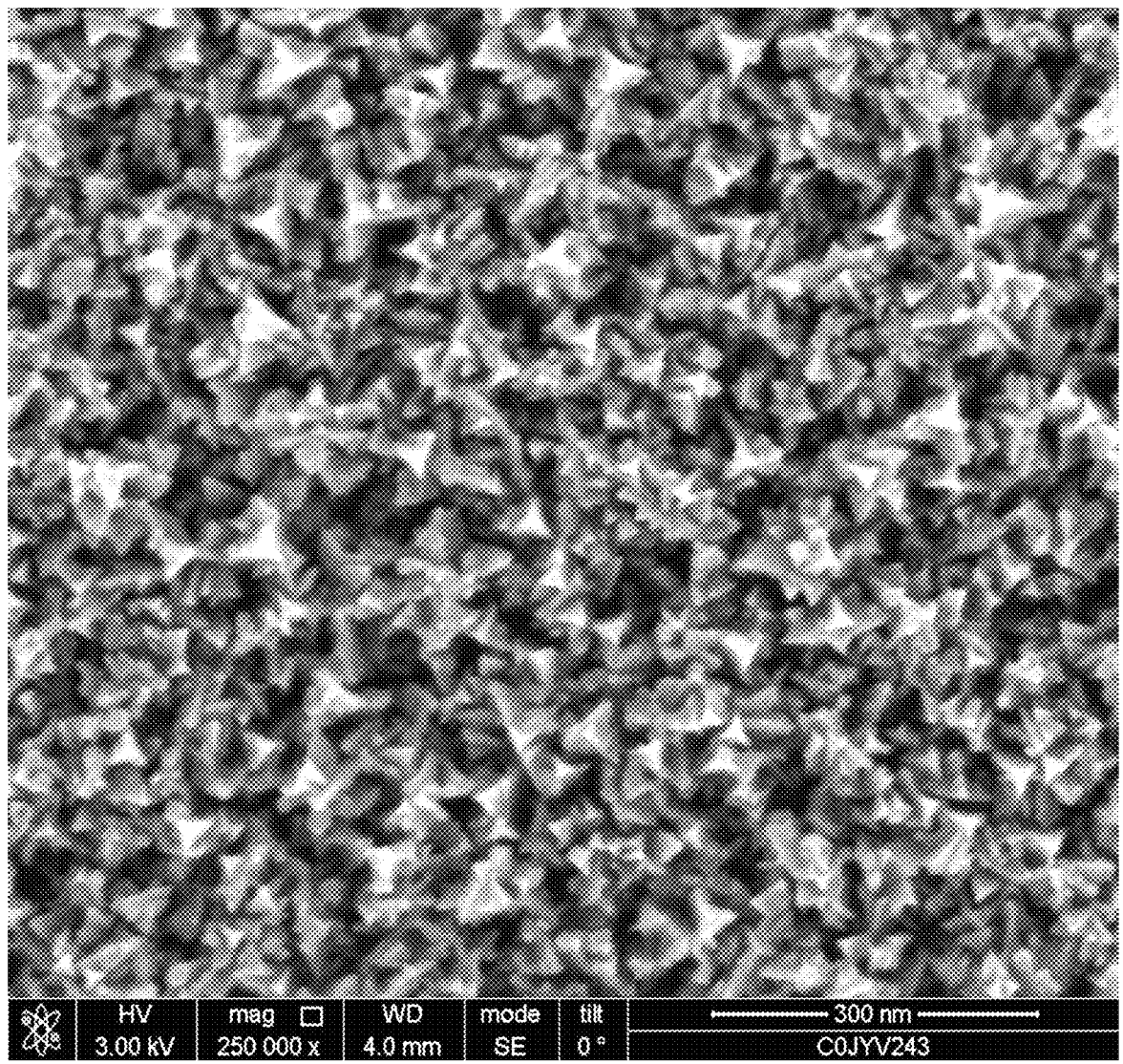
FIG. 4C provides a top down scanning electron microscopy image of a ruthenium-containing film sputter deposited at 200 W, room temperature, 20 mTorr, a flow rate of 10 sccm for argon, and a flow rate of 90 sccm for nitrogen, followed by a thermal treatment at 260° C.
Figure 4D:
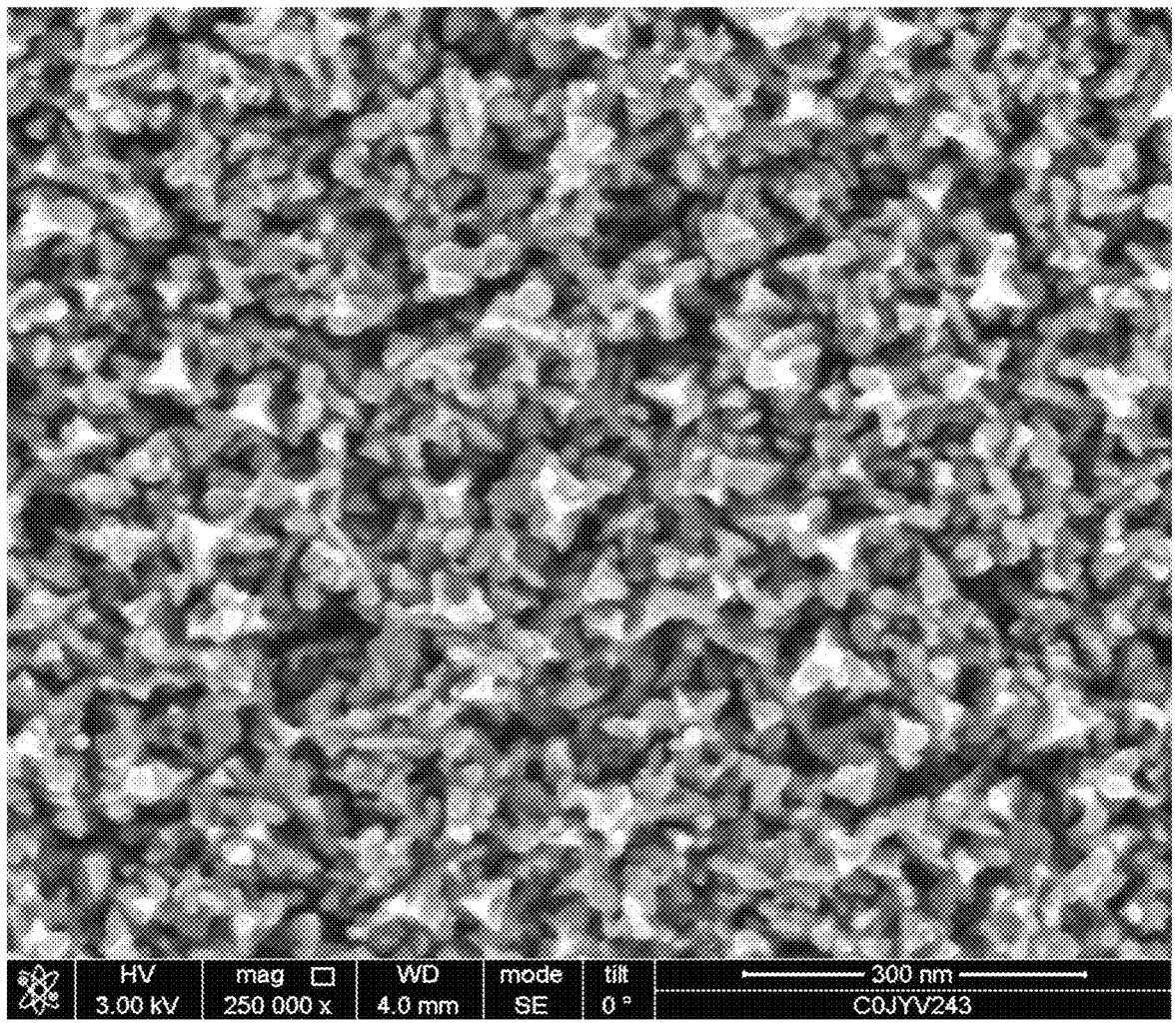
FIG. 4D provides a top down scanning electron microscopy image of a ruthenium-containing film sputter deposited at 200 W, room temperature, 20 mTorr, a flow rate of 10 sccm for argon, and a flow rate of 90 sccm for nitrogen, followed by a thermal treatment at 320° C.
Figure 5A:
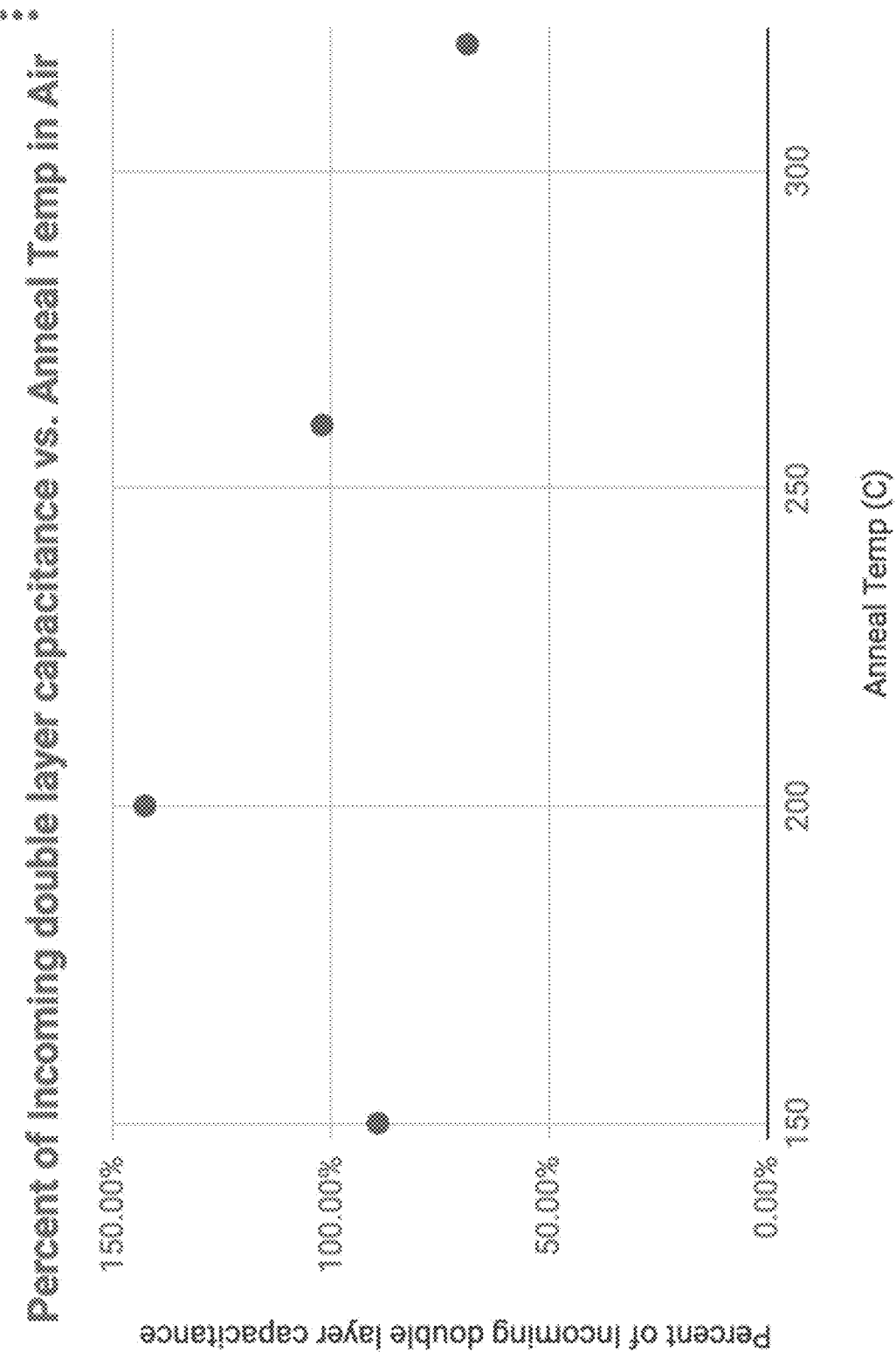
FIG. 5A provides a graph illustrating the effect of thermal processing on double layer capacitance at various temperatures on a ruthenium-containing film sputtered at 200 W, room temperature, 20 mTorr, a flow rate of 10 sccm for argon, and a flow rate of 90 sccm for nitrogen.

Following the deposition of the ruthenium-containing film onto the substrate, the ruthenium-containing film may be thermally treated. In some embodiments, the thermal treatment step comprises baking the ruthenium-containing film at a temperature ranging from between 120° C. to about 400° C. In other embodiments, the thermal treatment step comprises baking the ruthenium-containing film at a temperature ranging from between 150° C. to about 350° C. In other embodiments, the thermal treatment step comprises baking the ruthenium-containing film at a temperature ranging from between 150° ° C. to about 300° C. In other embodiments, the thermal treatment step comprises baking the ruthenium-containing film at a temperature ranging from between 150° C. to about 250° C. In other embodiments, the thermal treatment step comprises baking the ruthenium-containing film at a temperature ranging from between 180° C. to about 200° C. In yet other embodiments, thermal process is conducted at a temperature of about 200° C. The effect of temperature on the morphology of four ruthenium-containing films are shown in FIGS. 4A (150° C.), 4B)(200° C., 4C (260° C.), and 4D (320° C.). Notably, thermal processing at a temperature of about 150° C. provides a surface showing about 55% atomic oxygen and about 45% atomic nitrogen. In comparison, thermal processing at subsequently higher temperatures (e.g. 260° C. and 320° C.) showed an increase in oxygen atomic percent and decrease in nitrogen atomic percent. In some embodiments, thermal processing is conducted at a temperature and for a time period such that the double layer capacity of the thermally processed material is increased as compared to an unprocessed ruthenium-containing material. In some embodiments, a percentage increase in double layer capacitance ranges from between about 110% to about 160% (see, e.g., FIG. 5A). In some embodiments, the percentage increase ranges from between about 120% to about 150%. In some embodiments, thermal processing is conducted at a temperature above 140° C. for a sufficient time period (e.g. 15 min to 120 min) such that the double layer capacitance of the material ranges from between about 200 pF/um$^2$ to about 320 pF/um$^2$. In other embodiments, the double layer capacitance of the thermally treated ruthenium-containing film ranges from about 200 pF/um$^2$ to about 300 pF/um$^2$. In other embodiments, the double layer capacitance of the thermally treated ruthenium-containing film ranges from about 200 pF/um$^2$ to about 280 pF/um$^2$. In other embodiments, the double layer capacitance of the thermally treated ruthenium-containing film ranges from about 200 pF/um$^2$ to about 260 pF/um$^2$. In other embodiments, the double layer capacitance of the thermally treated ruthenium-containing film ranges from about 220 pF/um$^2$ to about 240 pF/um$^2$.

Figure 3C:
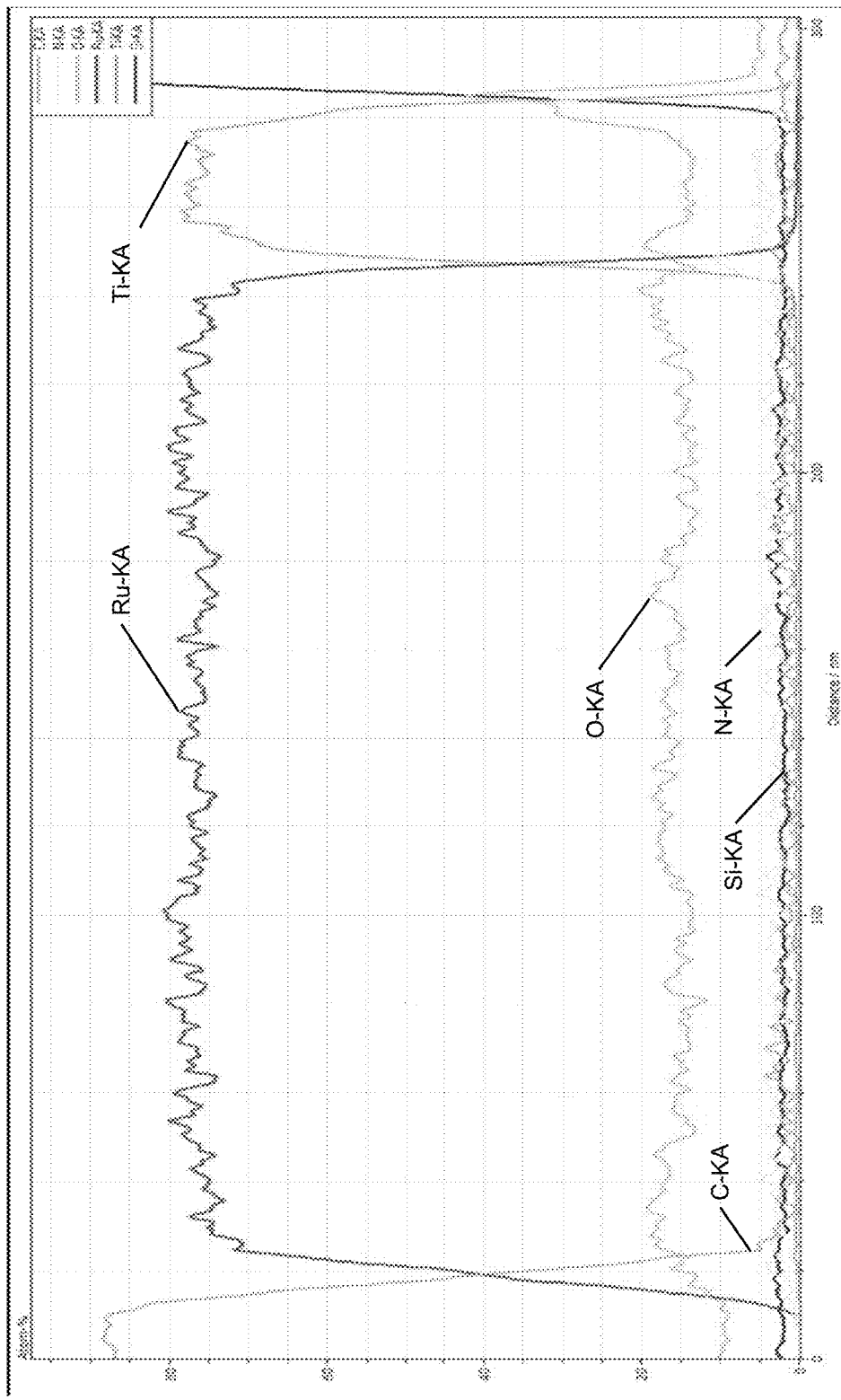
FIG. 3C sets forth energy dispersive x-ray spectroscopy results for a ruthenium-containing film sputtered at a flow rate of 10 sccm for argon and 20 sccm for argon, followed by thermal treatment. The data suggests that as compared with FIG. 3A, a significant increase in oxygen content is observed.
Figure 3D:
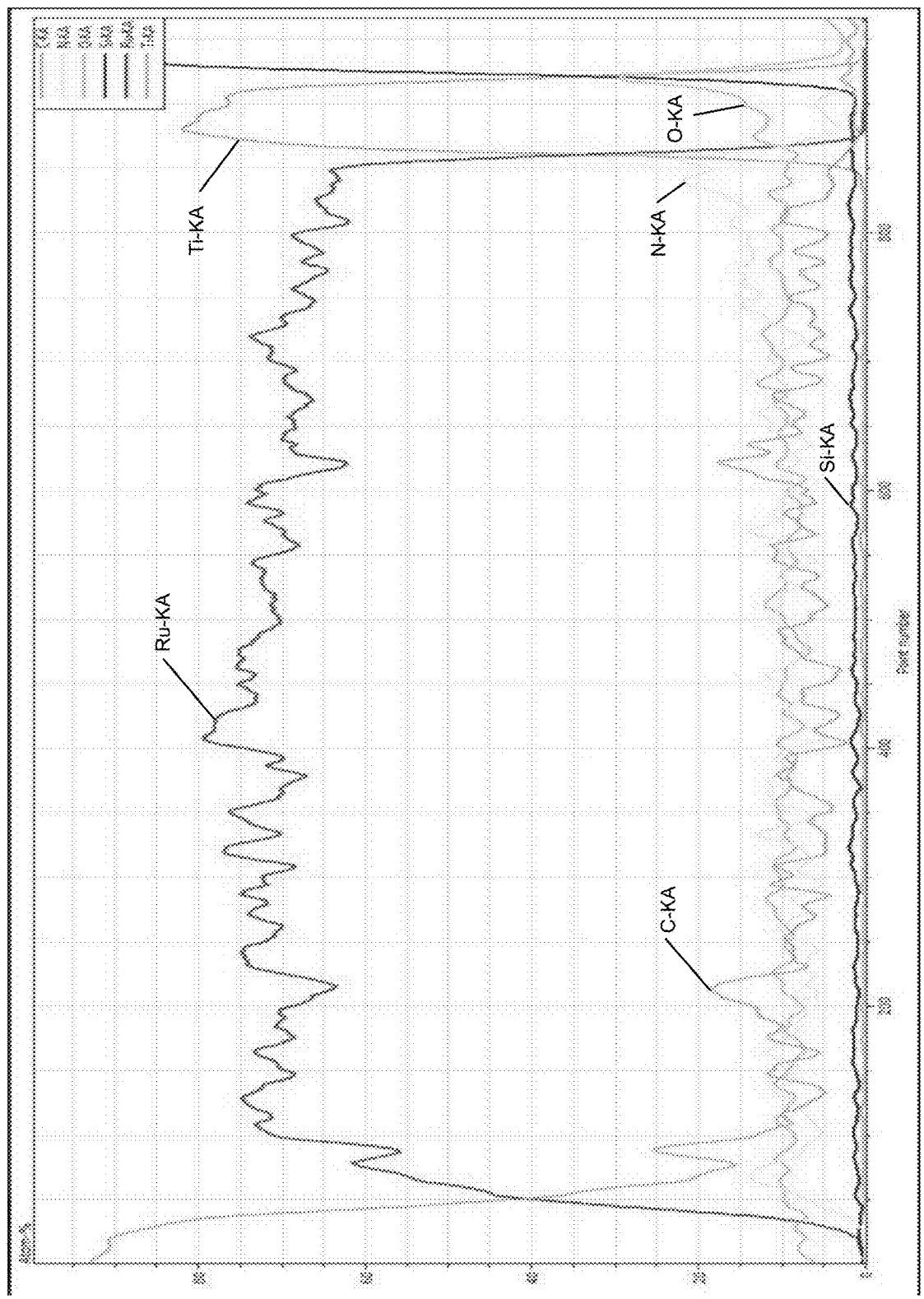
FIG. 3D sets forth energy dispersive x-ray spectroscopy results for a ruthenium-containing film sputtered at a flow rate of 10 sccm for argon and 90 sccm for argon, followed by thermal treatment. The data suggests that as compared with FIGS. 3B and 3C, only a small increase in oxygen content is observed.

In some embodiments, the ruthenium-containing material after thermal processing comprises ruthenium, oxygen, and nitrogen. In some embodiments, the amount of oxygen incorporated into the ruthenium-containing material post-processing depends on the amount of nitrogen introduced during film growth. For example, those films comprising a high amount of nitrogen (e.g. about 15%) incorporated less oxygen upon thermal treatment than those films having a low amount of nitrogen (e.g. about 5%). FIG. 3C compares energy dispersive x-ray spectroscopy (EDS) data both before and after thermal processing for a ruthenium-containing film having a low initial amount of nitrogen (compare FIG. 3C against FIG. 3A which illustrates the spectrum prior to thermal processing). On the other hand, FIG. 3D compares EDS data both before and after thermal processing for a ruthenium-containing film having a high initial amount of nitrogen (compare FIG. 3D against FIG. 3B which illustrates the spectrum prior to thermal processing).

In some embodiments, the thermally processed ruthenium-containing films have a surface composition ratio of (N+O)/Ru as measured by x-ray photoelectron spectroscopy (XPS) ranging between about 1.5 to about 3.5. In other embodiments, the surface composition ratio ranges from between about 1.8 to about 3.2. In yet other embodiments, the surface composition ratio ranges from between about 2 to about 3. In even further embodiments, the surface composition ration ranges from between about 2 to about 2.5. In yet further embodiments, the surface composition ration ranges from between about 2.1 to about 2.4.

Figure 5B:
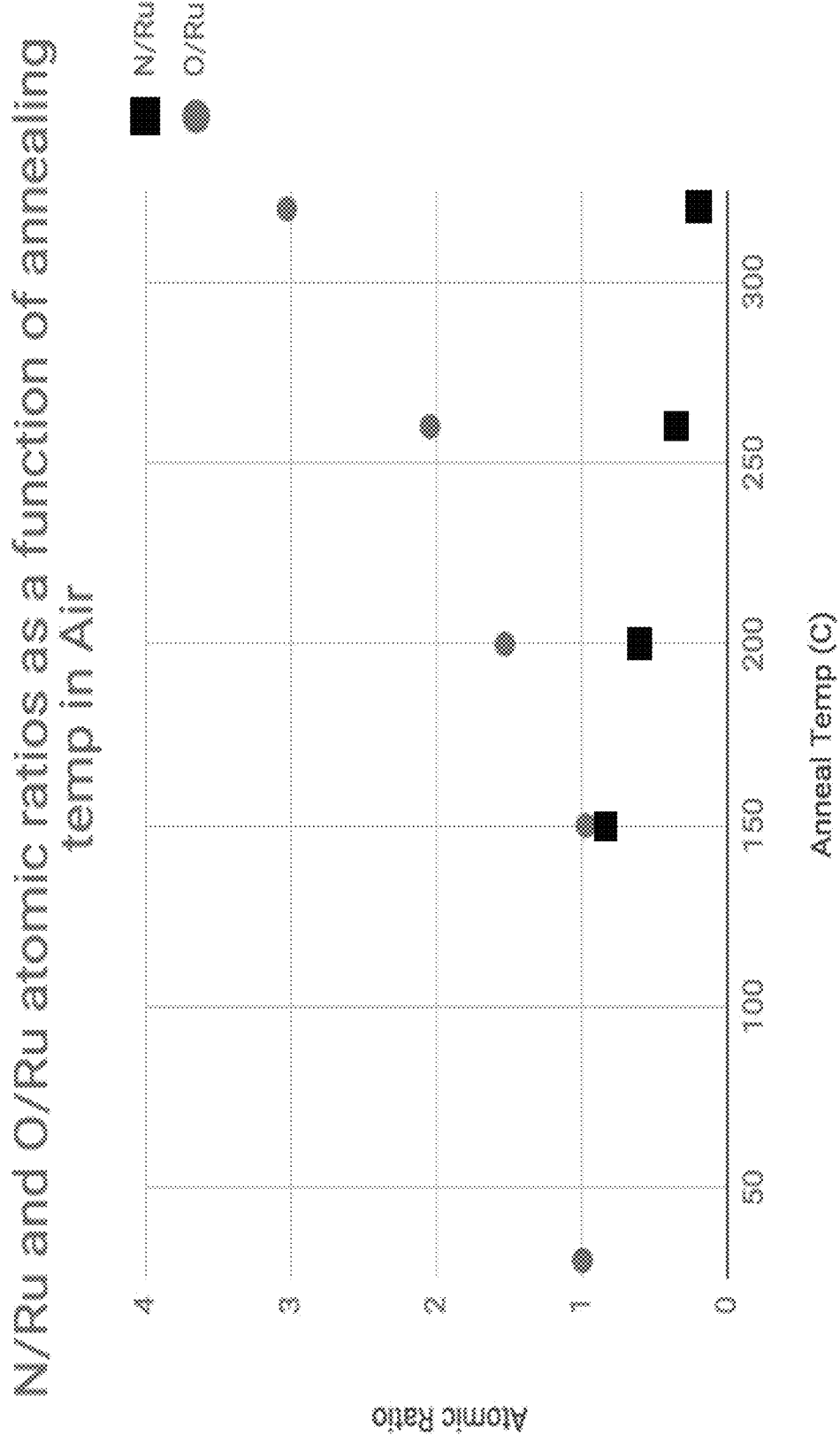
FIG. 5B provides a graph illustrating the effect of thermal processing on atomic ratios of ruthenium, nitrogen, and oxygen at various temperatures on a ruthenium-containing film sputtered at 200 W, room temperature, 20 mTorr, a flow rate of 10 sccm for argon, and a flow rate of 90 sccm for nitrogen.
Figure 5C:
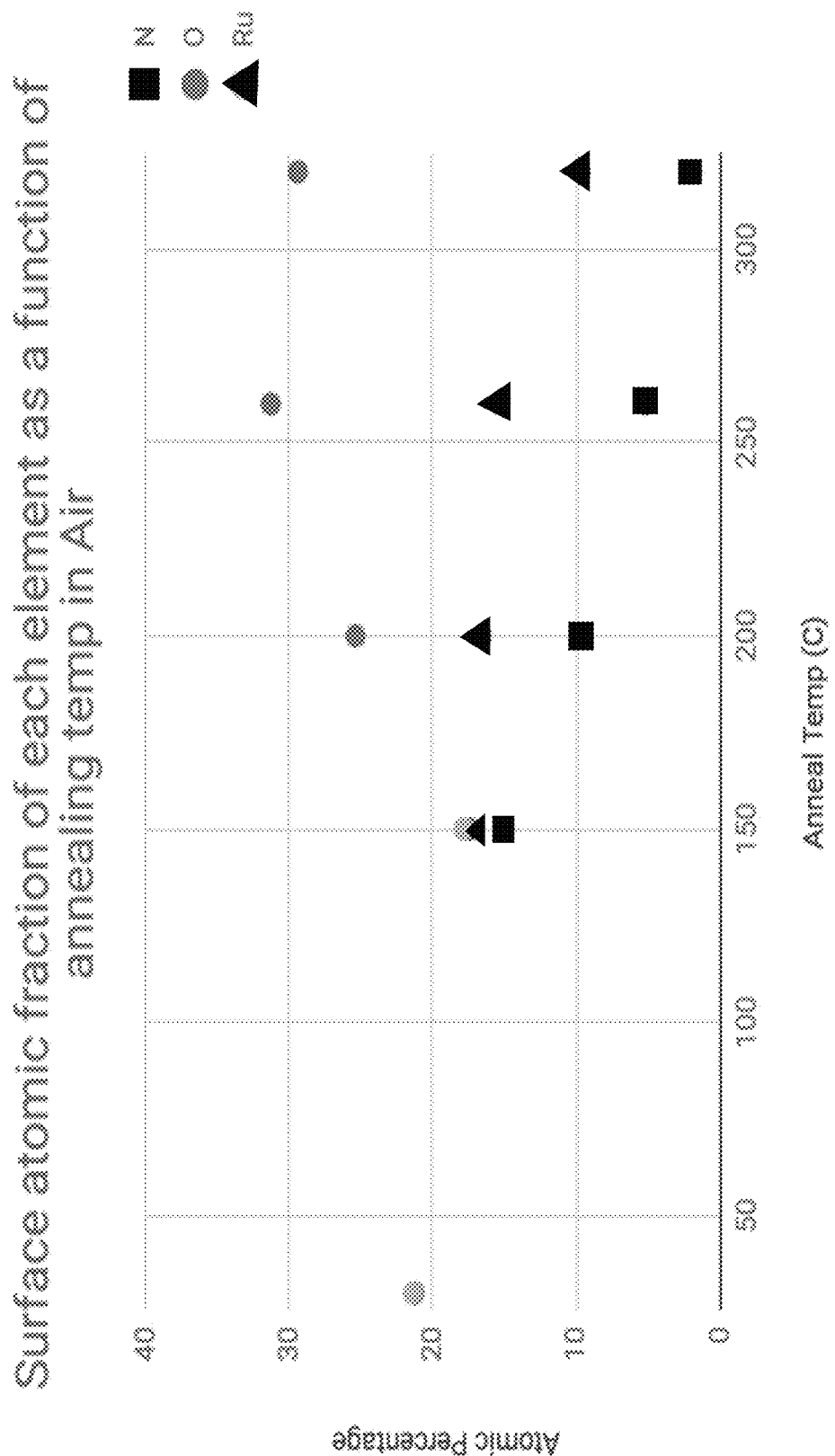
FIG. 5C provides a graph illustrating the effect of thermal processing on atomic percentages of ruthenium, nitrogen, and oxygen at various temperatures on a ruthenium-containing film sputtered at 200 W, room temperature, 20 mTorr, a flow rate of 10 sccm for argon, and a flow rate of 90 sccm for nitrogen.
Figure 6A:
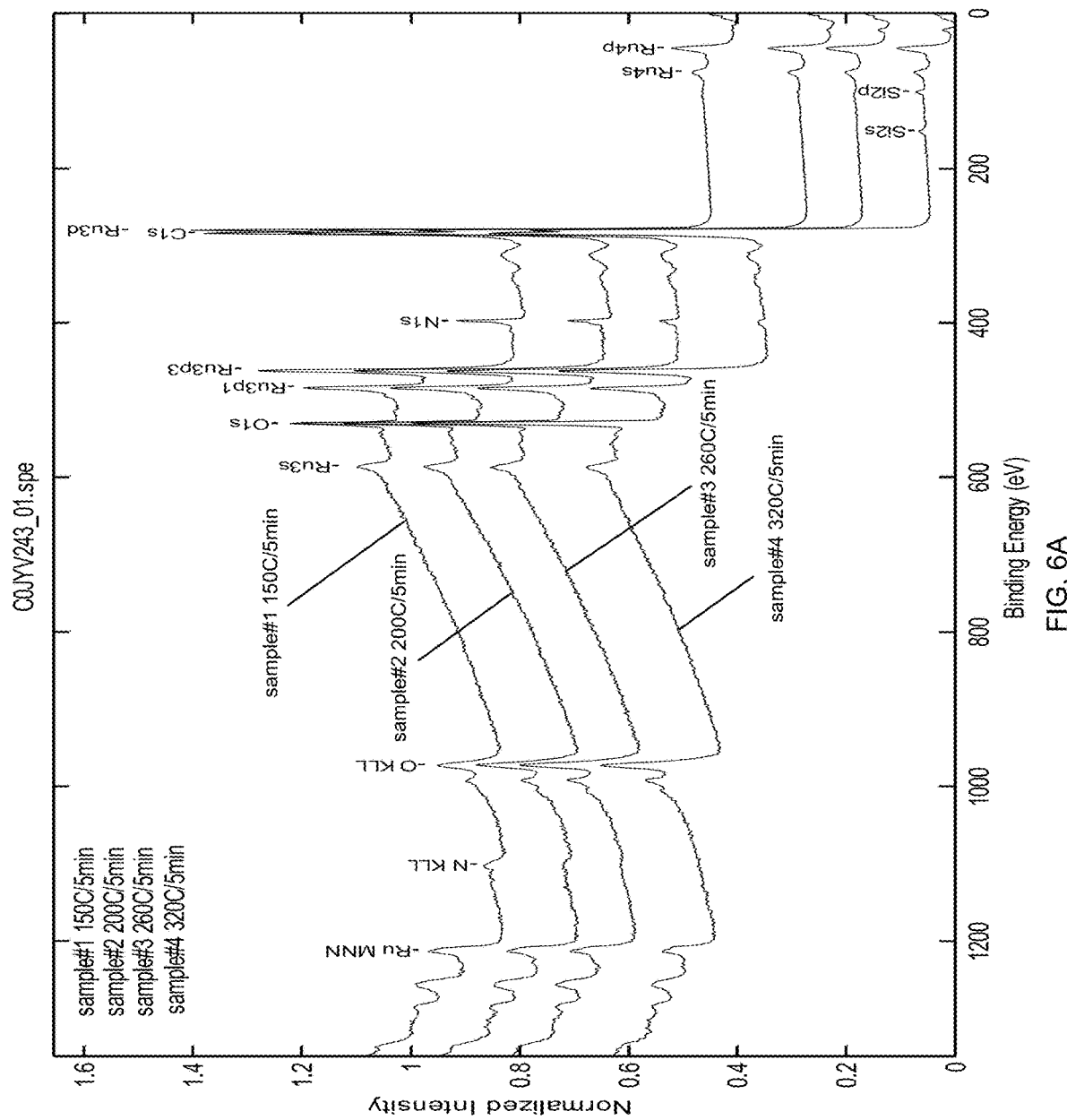
FIG. 6A illustrates x-ray photoelectron spectroscopy data for four ruthenium-containing samples (see also Table 1, herein).
Figure 6B:
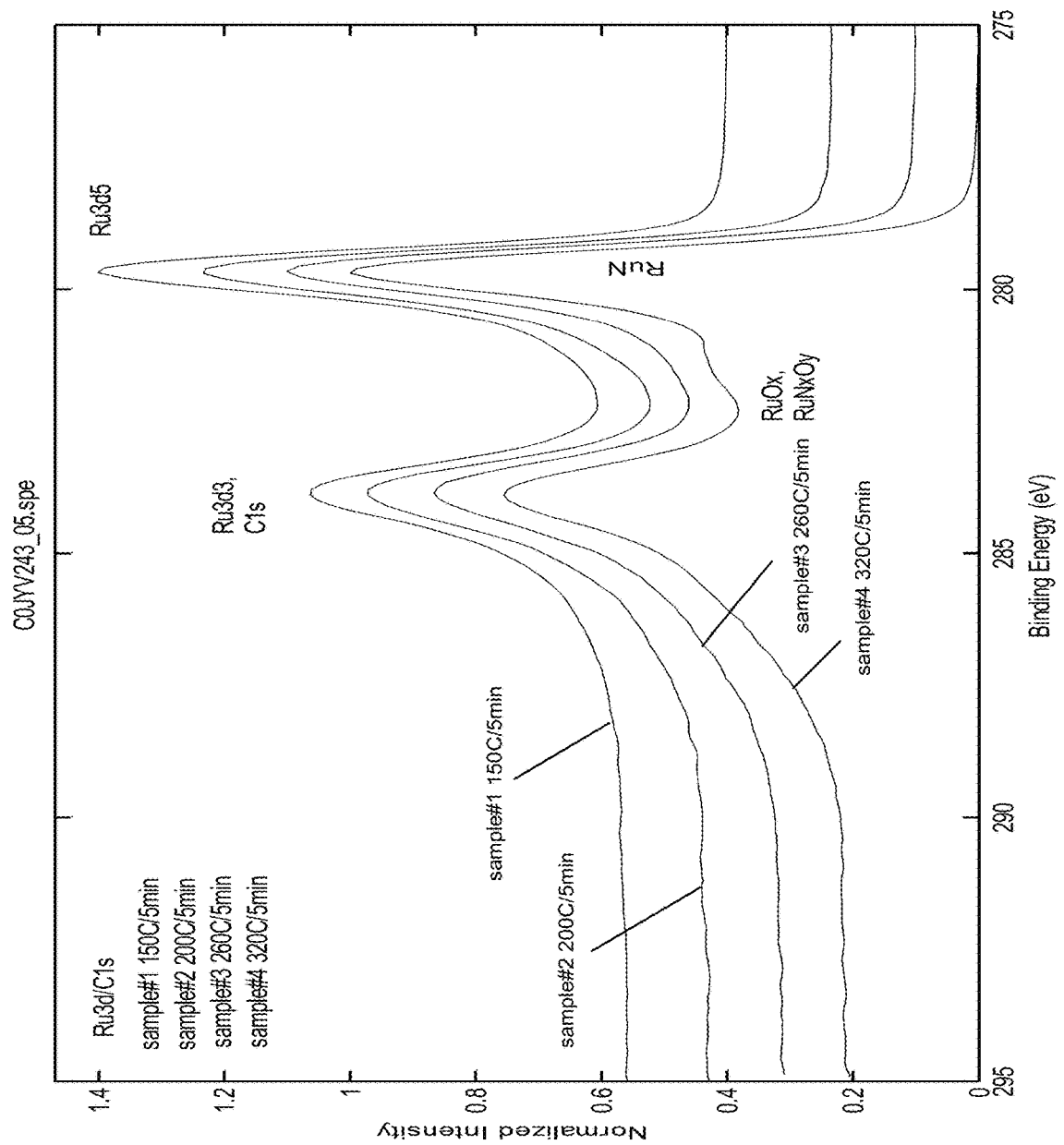
FIG. 6B illustrates x-ray photoelectron spectroscopy data (C1s) for four ruthenium-containing samples.
Figure 6C:
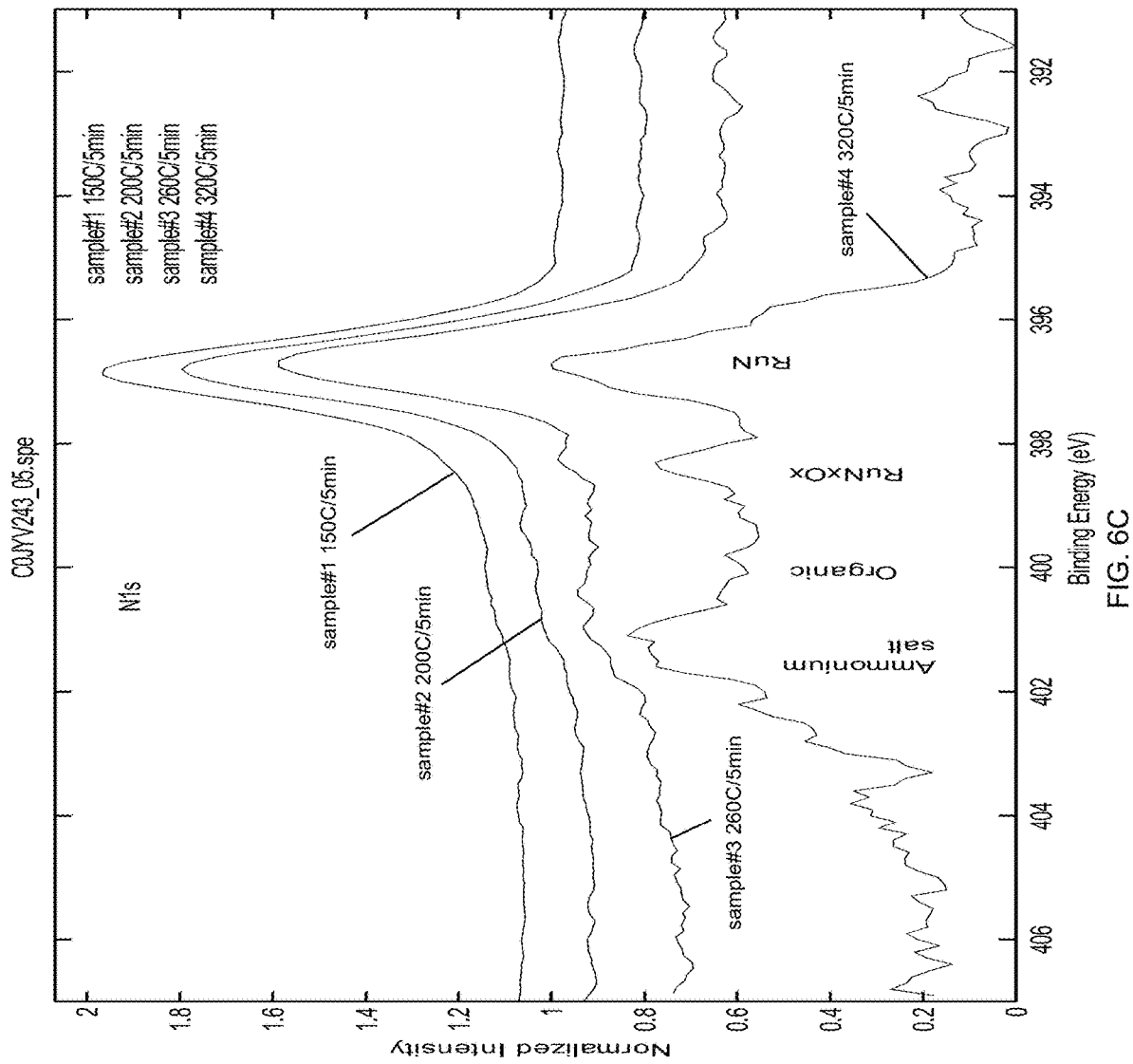
FIG. 6C illustrates x-ray photoelectron spectroscopy data (N1s) for four ruthenium-containing samples.
Figure 6D:
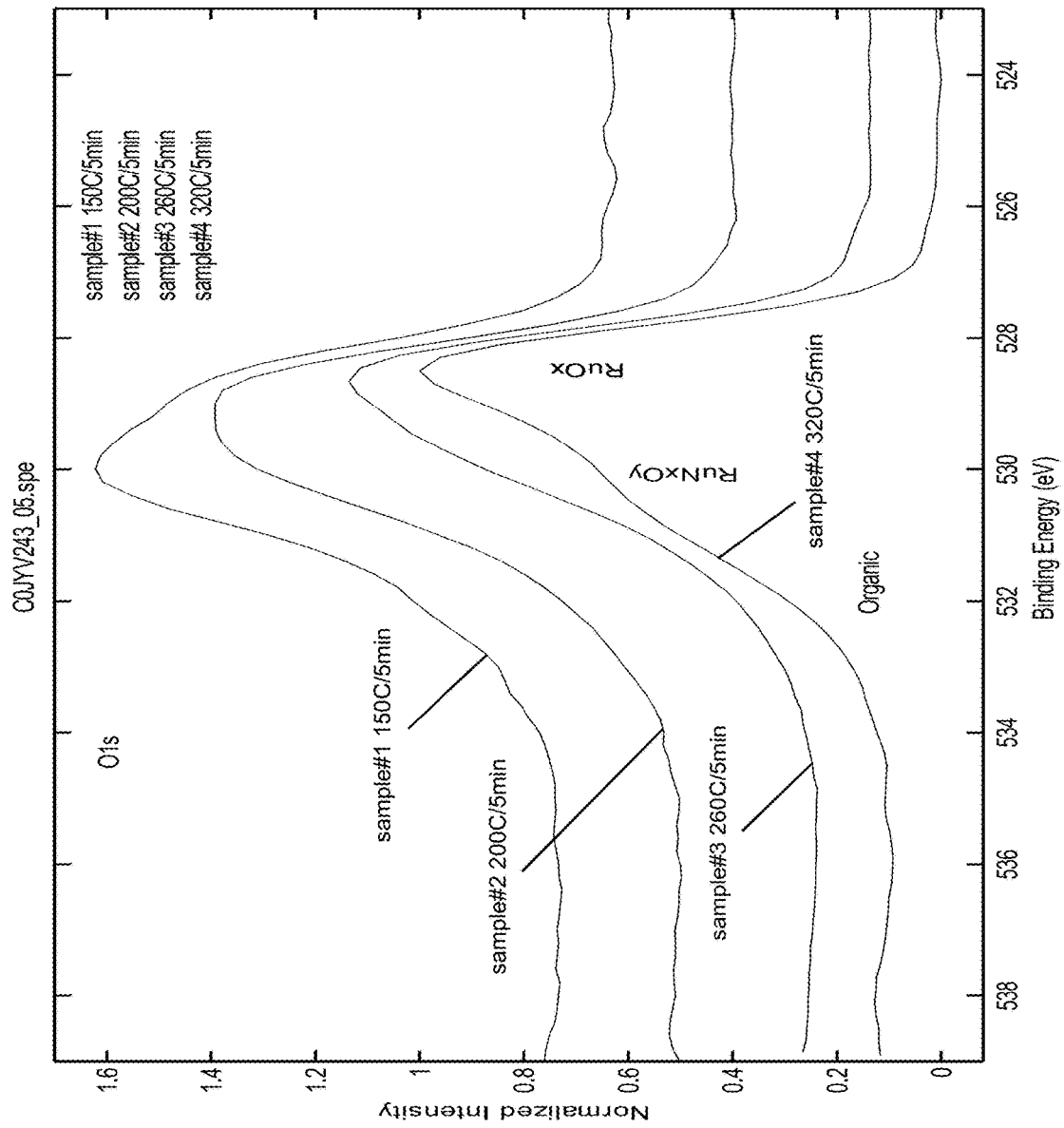
FIG. 6D illustrates x-ray photoelectron spectroscopy data (O1s) for four ruthenium-containing samples.

Table 1 below summarizes the (XPS) data (see FIGS. 6A through 6D) of four different thermally treated samples. In samples 1, 2, and 3 it is believed that nitrogen is primarily in the form of a nitride with smaller amounts of oxynitrides. Comparatively, the nitride component of the N1s spectrum of Sample 4 was weaker than that of the surfaces of Samples 1, 2, and 3. On the other hand, the XPS data shows that oxygen is present primarily as ruthenium oxides, hydroxides, and oxynitrides. It is believed that the relative contribution of the oxides was generally higher on the samples with higher annealing temperatures, whereas the samples with lower annealing temperatures had larger contributions of the oxynitrides and possibly hydroxides. FIGS. 5B and 5C further illustrate the relative amounts of ruthenium, nitrogen, and oxygen for one particular sample as a function of annealing temperature (using a sample deposited at 200 watts, 20 mTorr, 10 sccm Ar, and 90 sccm nitrogen).

TABLE 1

XPS surface component analysis of four different
ruthenium-containing samples post-thermal treatment.

| Sample | C | N | O | Si | Ru | (N + O)/Ru |
|---|---|---|---|---|---|---|
| sample#1 150 C./5 min | 49.7 | 15.0 | 17.4 | — | 17.9 | 1.81 |
| sample#2 200 C./5 min | 48.2 | 9.7 | 25.4 | — | 16.6 | 2.11 |
| sample#3 260 C./5 min | 48.2 | 5.2 | 31.3 | — | 15.3 | 2.39 |
| sample#4 320 C./5 min | 56.9 | 2.0 | 29.4 | 1.9 | 9.7 | 3.2 |

Nanopore Sequencing Overview

Nanopore sequencing of a polynucleotide, e.g. DNA or RNA, may be achieved by strand sequencing and/or exosequencing of the polynucleotide sequence. In some embodiments, strand sequencing comprises methods whereby nucleotide bases of a sample polynucleotide strand are determined directly as the nucleotides of the polynucleotide template are threaded through the nanopore. In some embodiments, a polynucleotide can be sequenced by threading it through a microscopic pore in a membrane. Bases can be identified by the way they affect ions flowing through the pore from one side of the membrane to the other. In some embodiments, one protein molecule can "unzip" a DNA helix into two strands. A second protein can create a pore in the membrane and hold an "adapter" molecule. A flow of ions through the pore can create a current, whereby each base can block the flow of ions to a different degree, altering the current. The adapter molecule can keep bases in place long enough for them to be identified electronically (see PCT Publication No. WO/2018/034745, and United States Patent Application Publication Nos. 2018/0044725 and 2018/0201992, the disclosures of which are hereby incorporated by reference herein in their entireties). In some embodiments, sequencing may be performed according to the helicase and exonuclease-based methods of Oxford Nanopore (Oxford, UK), Illumina (San Diego, Calif.), or the nanopore sequencing-by-expansion methods of Stratos Genomics (Seattle, Wash.).

In some embodiments, nanopores may be used to sequence nucleic acid molecules indirectly, i.e. indirect sequencing may include any method where a polymerized nucleic acid molecule does not pass through the nanopore during sequencing. In these embodiments, the nucleic acid molecule may be at least partially located in the vestibule of the nanopore, but not in the pore (i.e., narrowest portion) of the nanopore. The nucleic acid molecule may pass within any suitable distance from and/or proximity to the nanopore, and optionally within a distance such that byproducts released from nucleotide incorporation events (e.g. tags cleaved from tagged nucleotides as described below) are detected in the nanopore.

Figure 8:
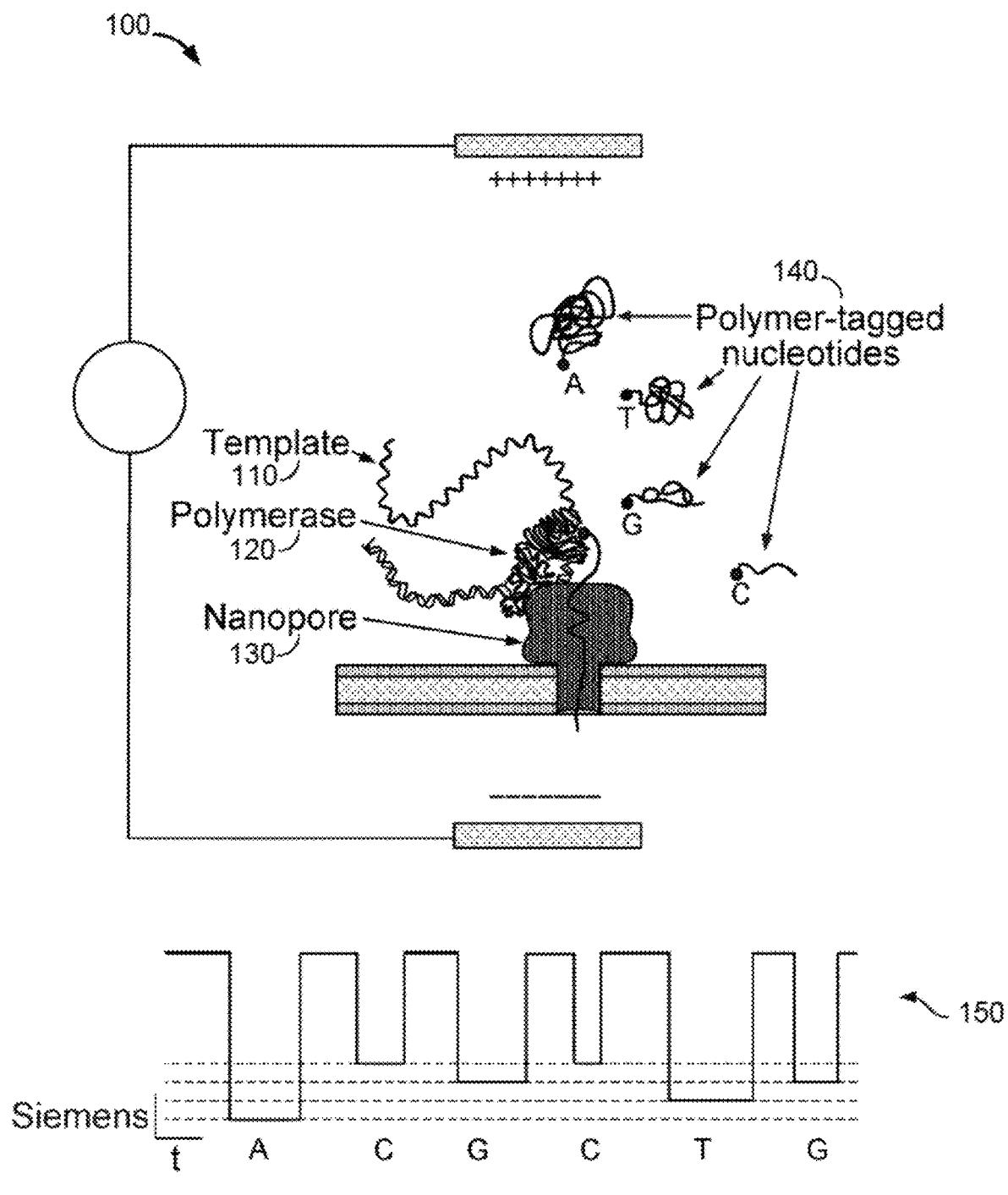
FIG. 8 illustrates single molecule DNA sequencing by a nanopore with polymer-tagged nucleotides (140). Each of the four nucleotides carry a different tag. During nanopore segueing, these tags, attached via the 5'-phosphate of the nucleotide, are released into the nanopore (130) one at a time where they produce unique current blockade signatures (150).

In some embodiments, nanopore-based sequencing utilizes an enzyme, such as one located in proximity to a nanopore, which incorporate nucleotides into a growing polynucleotide chain, wherein the growing polynucleotide chain is complimentary to a corresponding template nucleic acid strand. Nucleotide incorporation events are catalyzed by the enzyme, such as DNA polymerase or any mutant or variant thereof and use base pair interactions with a template molecule to choose amongst the available nucleotides for incorporation at each location. "Nucleotide incorporation events" are the incorporation of a nucleotide into a growing polynucleotide chain. Byproducts of nucleotide incorporation events may be detected by the nanopore. In some embodiments, a byproduct may be correlated with the incorporation of a given type of nucleotide. In some embodiments, the byproduct passes through the nanopore and/or generates a signal detectable in the nanopore. Released tag molecules (described below) are examples of byproducts of nucleotide incorporation events. By way of example, FIG. 8 depicts a DNA polymerase (120) bound in close proximity to a nanopore (130). A polynucleotide template (170) to be sequenced is added along with a primer (the template is associated with the enzyme). To this nanopore sequencing complex (including the primer), four differently tagged nucleotides (140) are added to the bulk aqueous phase. After polymerase catalyzed incorporation of the correct nucleotide, the tag will be released and pass through the nanopore (130) to generate a unique ionic current blockade signal (150), thereby identifying the added base electronically because each of the tags have distinct chemical structures. Additional details pertaining to such nanopore-based sequencing systems and methods are described in U.S. Pat. Nos. 9,605,309 and 9,557,294, the disclosures of which are hereby incorporated by reference herein in their entireties.

In some embodiments, a method for sequencing a nucleic acid molecule comprises (a) polymerizing tagged nucleotides (e.g. using an enzyme which incorporates one tagged nucleotide at a time using a first nucleic acid molecule as a template) wherein a tag associated with an individual nucleotide is released upon polymerization, and (b) detecting the released tag with the aid of a nanopore. In some embodiments, the enzyme draws from a pool of tagged nucleotides. As noted herein, each type of nucleotide is coupled to a different tag molecule so that when the tags are released and pass near or through the nanopore, they may be differentiated from each other based on a signal that is generated (see, e.g., FIG. 8). In some embodiments, each tag may have a different detectable signal, e.g. different signal intensities, different signal amplitudes, etc. which may be interpreted such as by base calling algorithms.

In some embodiments, the incorporated nucleotides are tagged nucleotides. Examples of tagged nucleotides are described in United States Patent Application Publication Nos. 2015/0368710 and 2018/0073071, the disclosures of which are hereby incorporated by reference herein in their entireties (see also Kumar et. al., PEG-Labeled Nucleotides and Nanopore Detection for Single Molecule DNA Sequencing by Synthesis, Sci Rep. 2012; 2:684). In some embodiments, nucleotide incorporation events release the tags from the tagged nucleotides, wherein the released tags are detected (see FIG. 8). In this way, the incorporated base may be identified (i.e., A, C, G, T or U) since a unique tag is released from each type of nucleotide (i.e., A, C, G, T or U).

In some embodiments, a released tag flows through the nanopore or in close proximity to the nanopore such that a sensing circuit detects an electrical signal associated with the tag as it passes through or near the nanopore (see FIG. 8). A detected signal (i.e. sequencing data) may be collected and stored in a memory location, and later used to construct a sequence of the nucleic acid. The collected signal may be processed to account for any abnormalities in the detected signal, such as errors. Suitable nanopore detectors are described in United States Patent Application Publication Nos. 2011/0193570 and 2018/0073071, the disclosures of which are hereby incorporated by reference herein in their entireties. Likewise, U.S. Pat. Nos. 9,377,437 and 8,324,914 describe the collection and analysis of electrical signals from nanopore-based sequencing systems, the disclosures of which are hereby also incorporated by reference herein in their entireties.

In some embodiments, the enzymes coupled or otherwise conjugated to nanopores include polynucleotide processing enzymes, e.g. DNA and RNA polymerases, reverse transcriptases, exonucleases, and unfoldases. In some embodiments, the enzyme is a helicase. In some embodiments, the enzyme can be a wild-type enzyme, or it can be a variant form of the wild-type enzyme. In some embodiments, the enzyme is a polymerase variant. For example, polymerase variants may include at least one alteration at a position corresponding to of H223. N224, Y225, H227, I295, Y342, T343, I357, S360, L361, I363, S365Q, S366, Y367, P368, D417, E475, Y476, F478, K518, H527, T529, M531, N535, G539, P542, N545, Q546, A547, L549, I550, N552, G553, F558, A596, G603, A610, V615, Y622, C623, D624, I628, Y629, R632, N635, M641, A643, I644, T647, I648, T651, I652, K655, W656, D657, V658, H660, F662, and L690 of SEQ ID NO:2 (Pol6 (with His tag)). Other suitable polymerase variants are disclosed in United States Patent Application Publication No. 2016/0222363, the disclosure of which is hereby incorporated by reference herein in its entirety. Yet other suitable enzymes are disclosed in U.S. Pat. No. 9,797,009, the disclosure of which is hereby incorporated by reference herein in its entirety. Even further suitable enzymes are disclosed in United States Patent Application Publication No. 2016/0257942.

In some embodiments, the nanopores of the nanopore sequencing complex include, without limitation, biological nanopores, solid state nanopores, and hybrid biological-solid state nanopores. Biological nanopores of the nanopore sequencing complexes include OmpG from *E. coli*, sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores. See, for example, United States Patent Application Publication No. 2017/0088588, the disclosure of which is hereby incorporated by reference herein in its entirety. In some embodiments, the variant nanopore of the nanopore sequencing complex is engineered to reduce the ionic current noise of the parental nanopore from which it is derived. Yet other nanopores are described in United States Patent Application Publication Nos. 2017/0268052, 2017/0356037 and 2018/0201993, the disclosures of which are hereby incorporated by reference herein in their entireties. Any nanopore variant now known or later discovered may be screened according to the methods described herein, such as contemporaneously with the screening of one or more enzyme variants (e.g. to identify a nanopore variant and enzyme variant pair that provides desirable properties).

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide). Methods for assembling nanopore sequencing complexes are described in U.S. Patent Application Publication No. 2017/0268052, the disclosure of which is hereby incorporated by reference herein in its entirety. Other suitable methods for complexing each of the different templates to nanopore-enzyme conjugates include those described in PCT Publication Nos. WO2014/074727, WO2006/028508, and WO2012/083249, the disclosures of each are hereby incorporated by reference herein in their entireties.

A chip for sequencing a nucleic acid sample can comprise a plurality of individually addressable nanopores. An individually addressable nanopore of the plurality can contain at least one nanopore formed in a membrane disposed adjacent to an integrated circuit. In some embodiments, each individually addressable nanopore can be capable of detecting a tag associated with an individual nucleotide.

Multiple nanopore sensors may be provided as arrays, such as arrays present on a chip or biochip. The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. Biochips and methods for making biochips are described in PCT Publication No. WO2015/061511, the disclosure of which is hereby incorporated by reference herein in its entirety. Further suitable biochips comprising a plurality of nanopores are described in United States Patent Application Publication No. 2017/0268052, the disclosure of which is hereby incorporated by reference herein in its entirety. Yet further suitable nanopore arrays are described in U.S. Pat. No. 8,986,928, the disclosure of which is hereby incorporated by reference herein in its entirety.

Nanopore Sequencing Cells and Circuitry

Figure 7A:
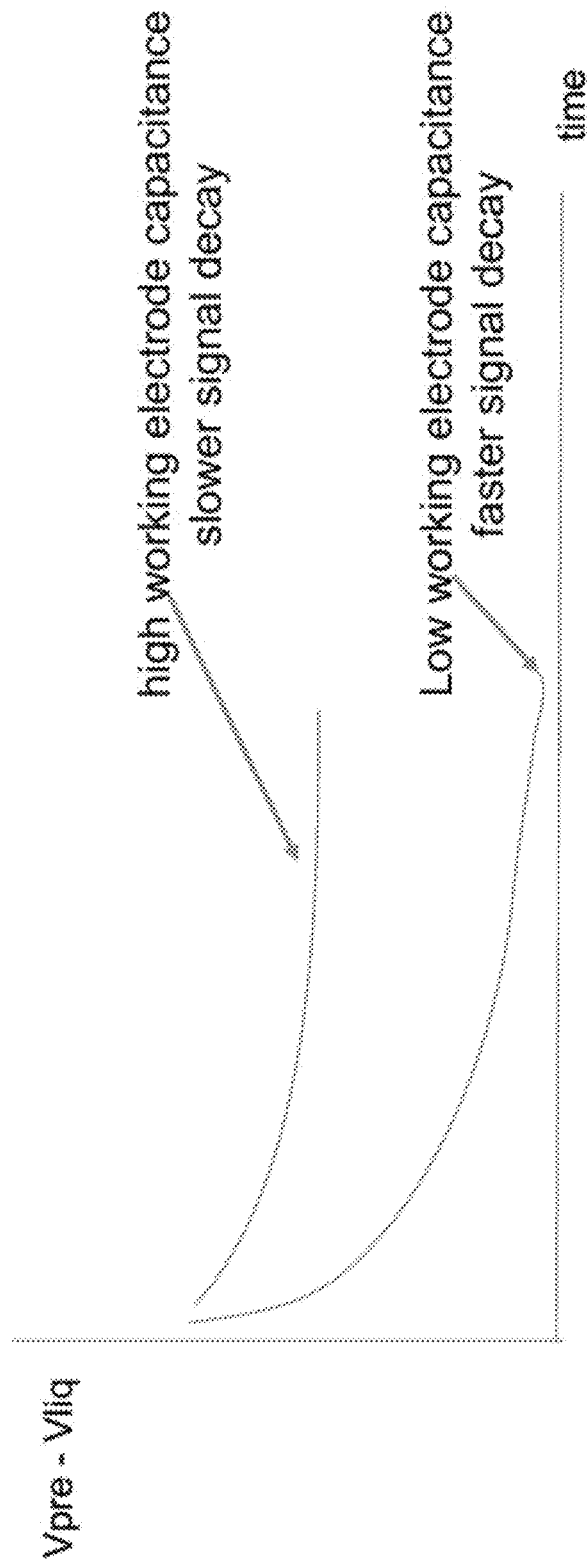
FIG. 7A sets forth a diagram demonstrating the difference in signal decay rate between a cell including an electrode comprised of a ruthenium-containing material (and having a high working electrode capacitance) and an electrode comprised of titanium nitride (and having a comparatively lower working electrode capacitance). The signal decay rate was measured by plotting the signal change on the ADC (analog to digital convertor) (see FIGS. 10A-10D) as a function of time when the switch to ADC is turned on. During that time, the Ncap discharges through the circuit that contains $C_{double\ layer}$ and $C_{bilayer}$ as illustrated in FIG. 10A. The measurement happened at the ASIC circuit on the chip
Figure 7B:
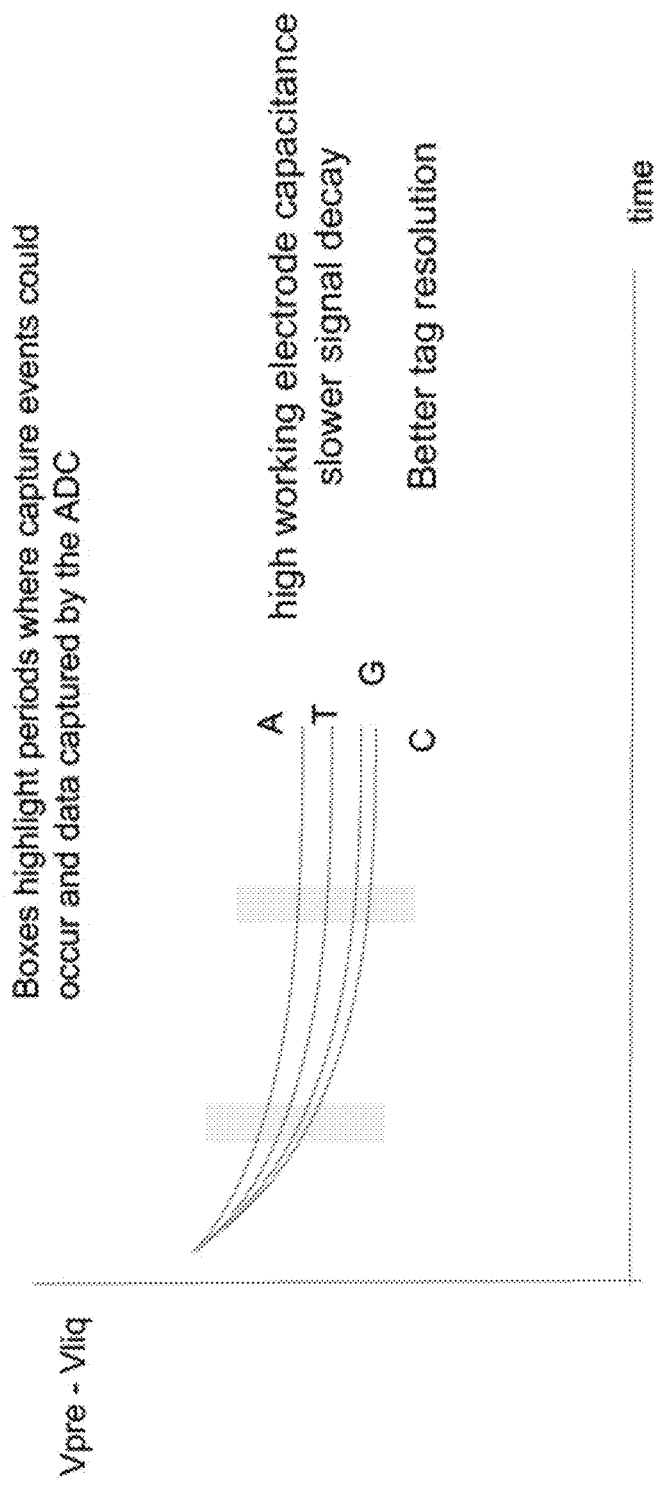
FIG. 7B illustrates a decay that occurs slowly (compare the slope of the curves of FIGS. 7B and 7C), and further shows the decay for each of four different tags associated with the four different nucleotides. Good separation is shown between the different signal decay curves, which provides for better signal separation and increased signal resolution as compared with decay curves shown in FIG. 7C.
Figure 7C:
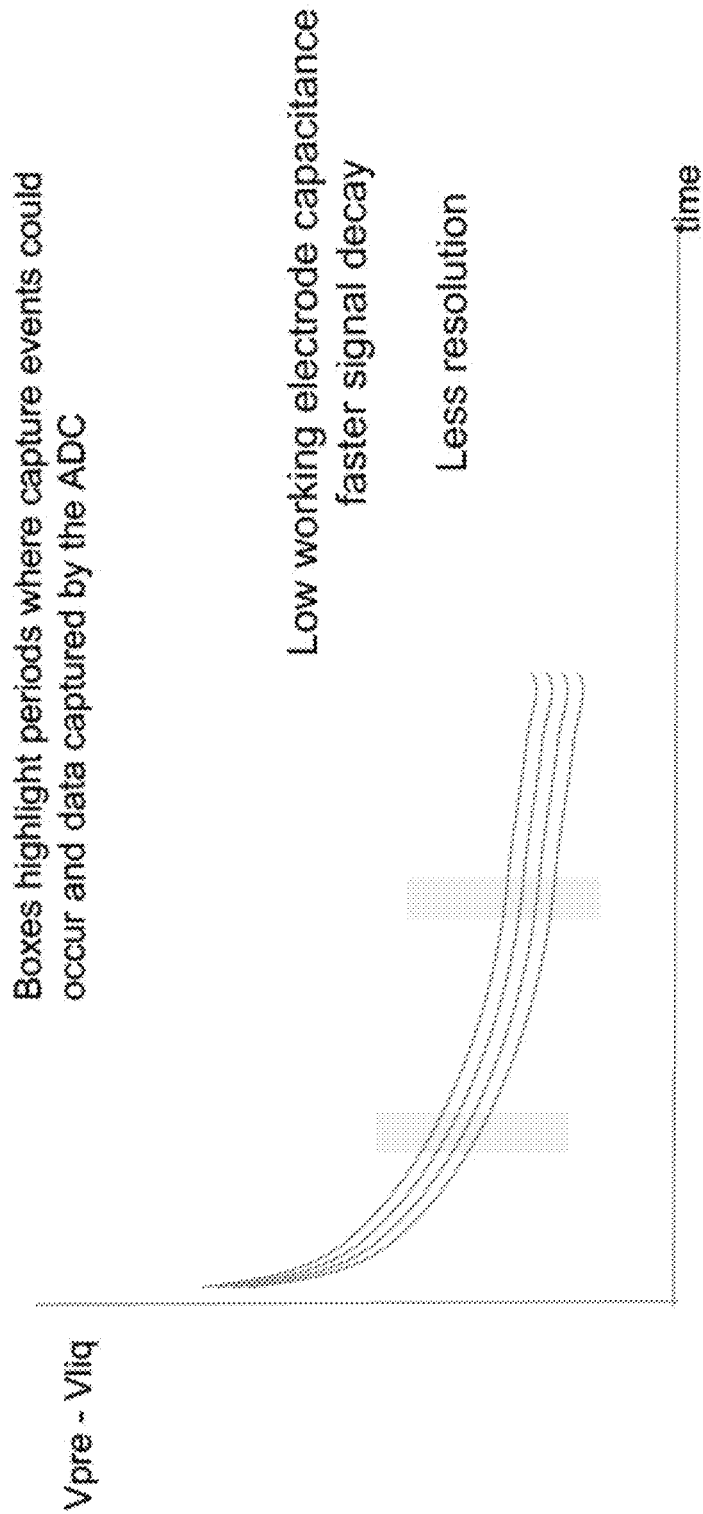
FIG. 7C illustrates a decay that occurs fast (as compared with FIG. 7B). Lower signal resolution is observed as compared with FIG. 7B.

The present disclosure is also directed to nanopore sequencing cells, chips, and/or nanopore sequencing devices including an electrode or working electrode comprising a material having a double layer capacitance of at least 300 pF/um$^2$. Applicants have unexpectedly discovered that the use of such a material facilitates improved signal decay rates as compared with prior art materials having lower double layer capacitances, e.g. titanium nitride materials. Indeed, it is believed that materials possessing high double layer capacitance (e.g. ruthenium-containing materials) have faster signal decays as compared with those materials having comparatively lower double layer capacitance (e.g. titanium nitride) (see FIGS. 7A-7C). The improved signal decay rates allow for better resolution of signals when different types of tag s when held inside the barrel of the nanopore. It is believed that the circuitry included within a sequencing device works in the sense that during data collection, there will be a voltage drop across the nanopore in the bilayer and a voltage drop across the electrical double layer capacitance at the electrode/electrolyte interface. It is believed that a higher electrical double layer capacitance allows for a faster decay of the signal (shorter half-time) (see FIGS. 7A-7C). Since nucleotides (A, T, C, G) having different tags can be threaded into the nanopore based on an applied waveform V, it is believed that a fast decay of signal allows better resolution of the different signal levels that corresponds to the tag (A, T, C, G). In some embodiments, the tags are designed so that they block the pore differently allowing for different signals to be acquired.

Figure 9:
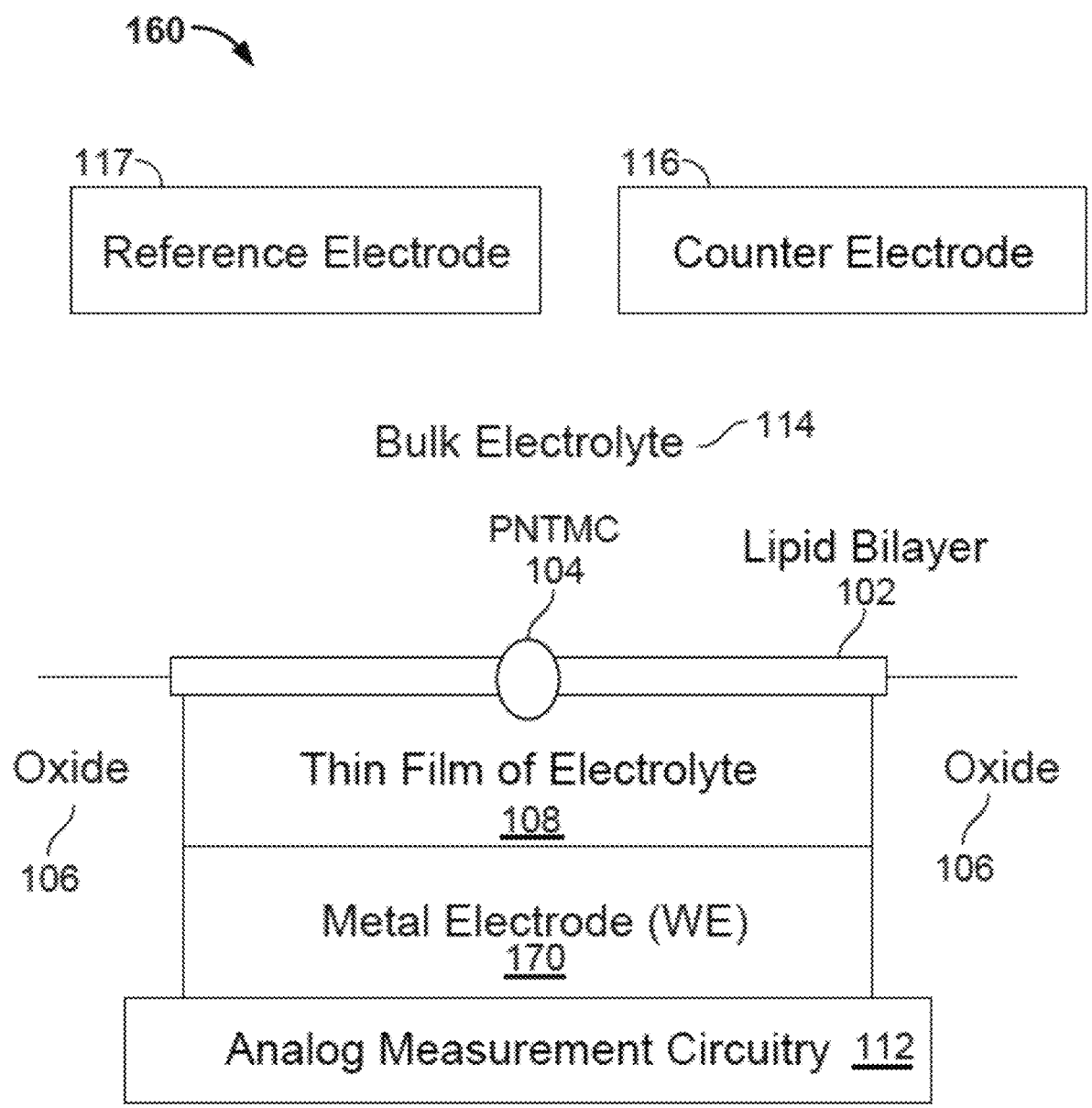
FIG. 9 illustrates an embodiment of a cell 100 in a nanopore based sequencing chip.

FIG. 9 illustrates an embodiment of a cell 160 in a nanopore based sequencing chip. In some embodiments, a membrane 102 is formed over the surface of the cell. In some embodiments, membrane 102 is a lipid bilayer. The bulk electrolyte 114 containing protein nanopore transmembrane molecular complexes (PNTMC) and the analyte of interest is placed directly onto the surface of the cell. In some embodiments, a single PNTMC 104 is inserted into membrane 102 by electroporation. In some embodiments, the individual membranes in the array are neither chemically nor electrically connected to each other. Thus, each cell in the array is an independent sequencing machine, producing data unique to the single polymer molecule associated with the PNTMC. In some embodiments, PNTMC 104 operates on the analytes and modulates the ionic current through the otherwise impermeable bilayer.

With continued reference to FIG. 9, analog measurement circuitry 112 is connected to a metal electrode 170 (e.g. an electrode comprised of ruthenium, oxygen, and nitrogen) covered by a thin film of electrolyte 108. In some embodiments, the thin film of electrolyte 108 is isolated from the bulk electrolyte 114 by the ion-impermeable membrane 102. PNTMC 104 crosses membrane 102 and provides the only path for ionic current to flow from the bulk liquid to working electrode 170. In some embodiments, the cell also includes a counter electrode (CE) 116, which is an electrochemical potential sensor. In some embodiments, the cell also includes a reference electrode 117.

Figure 10A:
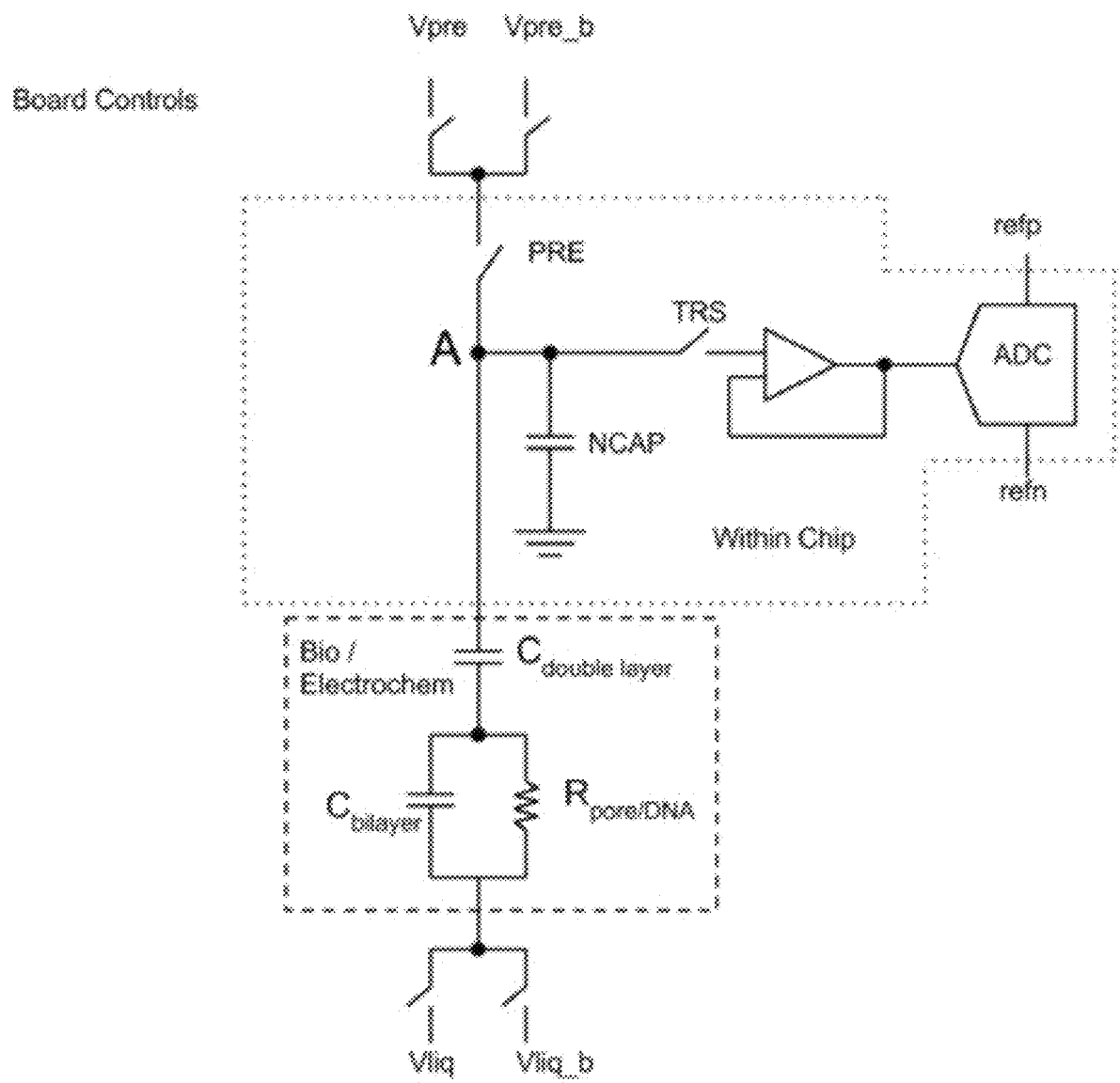
FIG. 10A illustrates an embodiment of a circuitry in a cell of a nanopore based sequencing chip, wherein the voltage applied across the nanopore can be configured to vary over a time period during which the nanopore is in a particular detectable state.
Figure 10B:
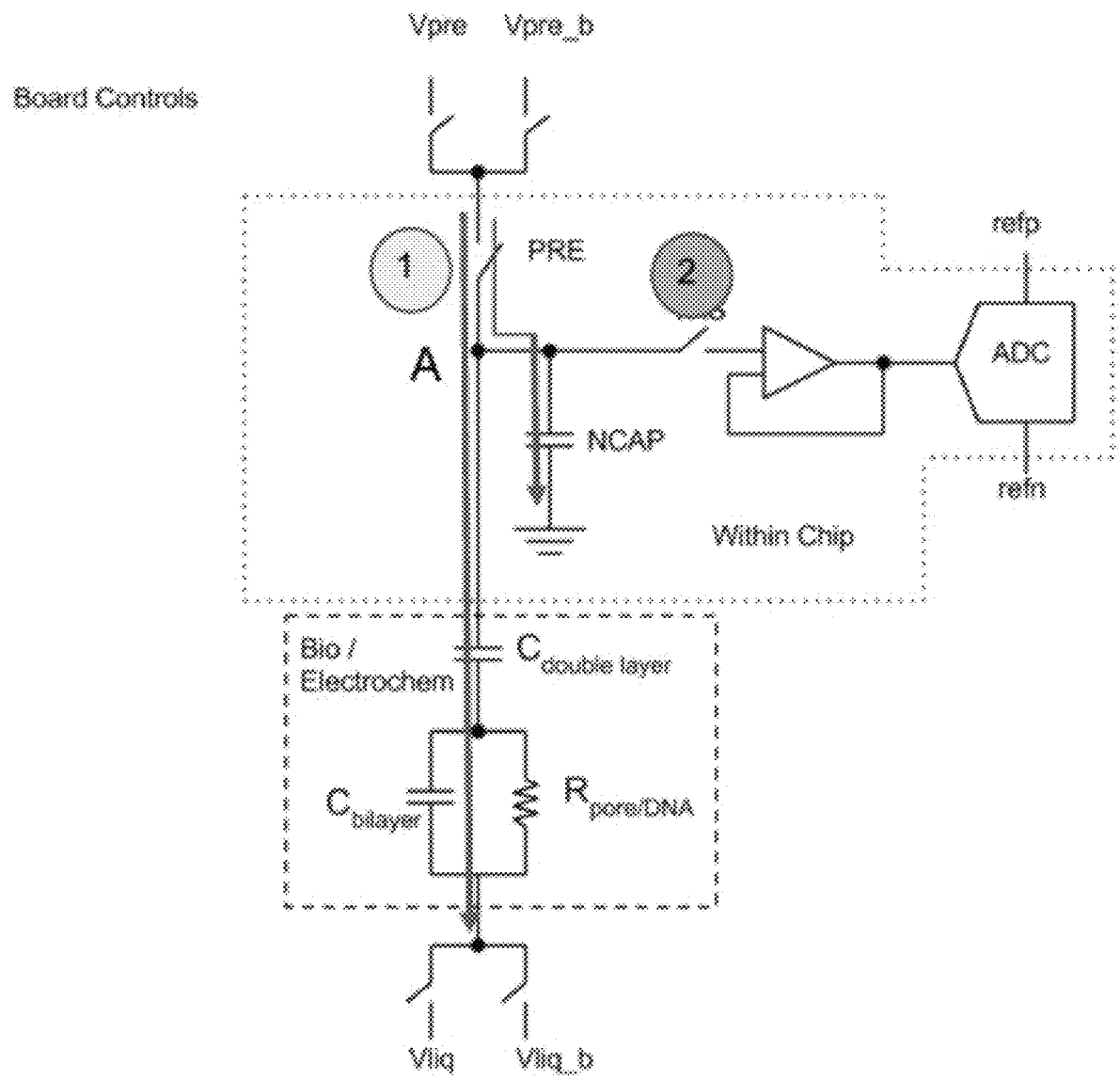
FIG. 10B illustrates a circuit where switch "1" (PRE) is closed and the switch "2" (TRS) is opened. When a voltage is applied in this configuration, the NCAP (a capacitor for charge storage and discharge) is charged to the working electrode (Vpre).
Figure 10C:
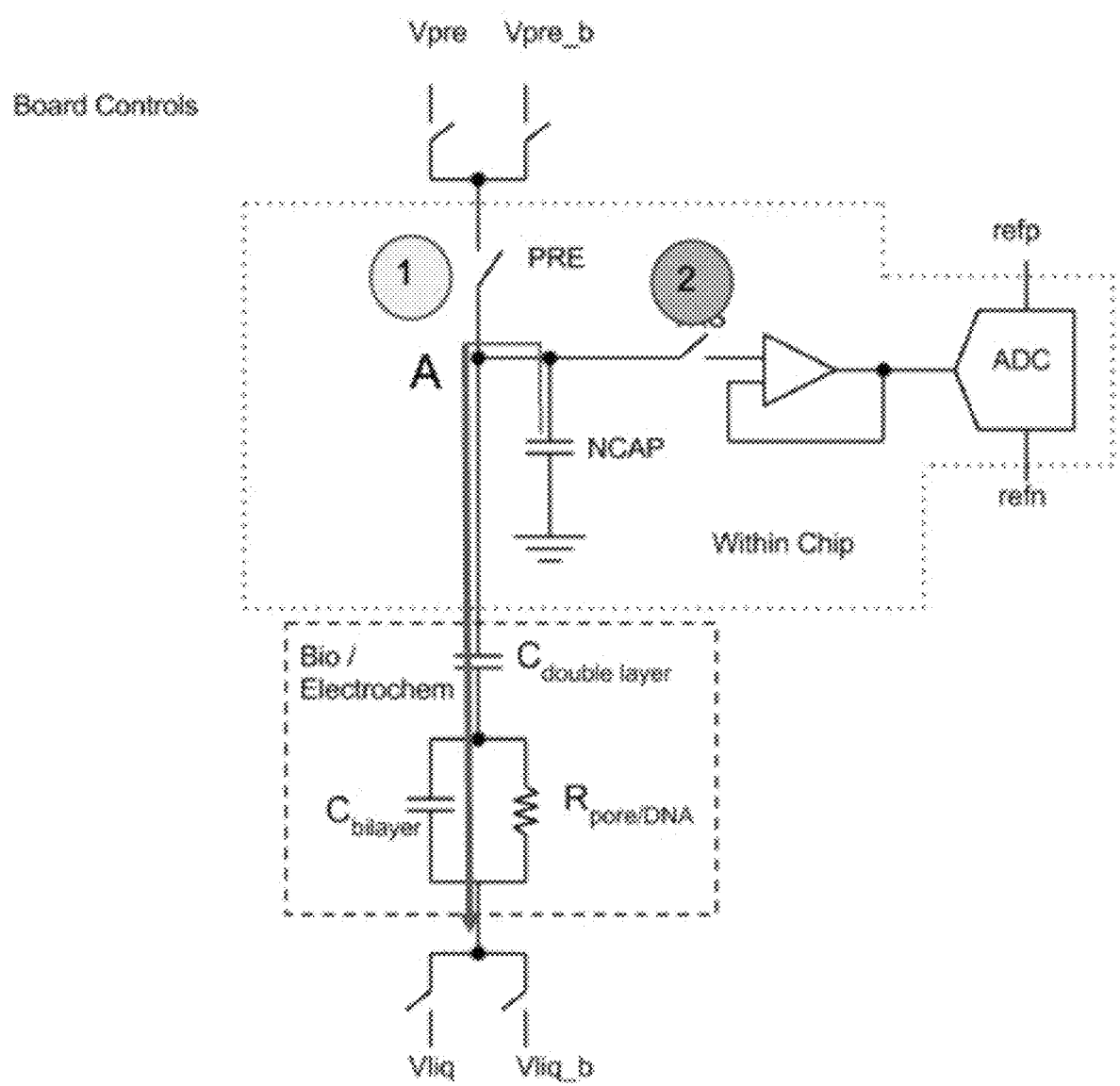
FIG. 10C illustrates a circuit where switch "1" (PRE) is open and the switch "2" (TRS) is closed. In this configuration, NCAP discharges and the discharge occurs from the NCAP through to the counter electrode (Vliq) (see arrow). The rate of discharge depends on the electrode double capacitance relative to the bilayer capacitance. The higher the value for the electrode double capacitance, the slower the decay (which, in the end, improves signals, such as during sequencing). A high working electrode capacitance ($C_{double\ layer}$) implies a slower decay in Vpre-Vliq. This is believed to improve signal resolution as a nanopore with a different tag has a different resistance (Rpore), causing a difference in the decay rate (see FIGS. 7B and 7C).
Figure 10D:
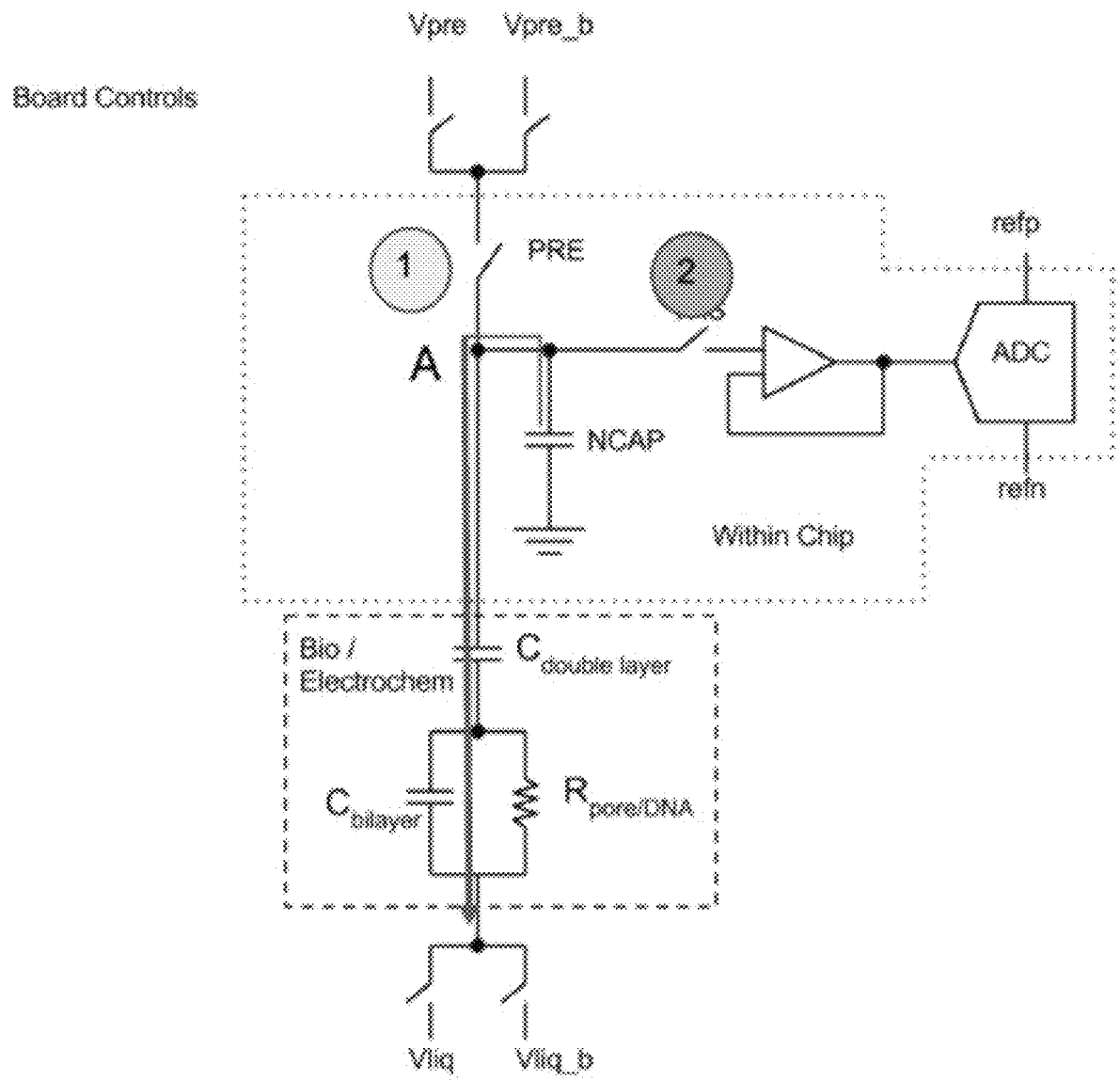
FIG. 10D illustrates a circuit where switch "1" (PRE) is open and the switch "2" (TRS) is opened. In this configuration, the ADC (analog to digital converter) can read the voltage at node A, allowing for the collection of a data point.

FIGS. 10A-10D illustrate an embodiment of circuitry in a cell of a nanopore based sequencing chip, wherein the voltage applied across the nanopore can be configured to vary over a time period during which the nanopore is in a particular detectable state. One of the possible states of the nanopore is an open-channel state when a tag-attached polyphosphate is absent from a barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. FIGS. 10B-10C illustrate additional embodiments of a circuitry in a cell of a nanopore based sequencing chip, wherein the voltage applied across the nanopore can be configured to vary over a time period during which the nanopore is in a particular detectable state.

FIGS. 10A-10D further illustrate a nanopore that is inserted into a membrane, where the nanopore and membrane are situated between a working electrode (Vpre) and a counter electrode (Vliq), such that a voltage may be applied across the nanopore. In some embodiments, the nanopore is also in contact with a bulk liquid/electrolyte. As used therein, the term "cell" is meant to include at least a membrane, a nanopore, a working cell electrode, and the associated circuitry. In some embodiments, the counter electrode (Vliq) is shared between a plurality of cells and is therefore also referred to as a common electrode. In some embodiments, the common electrode may be configured to apply a common potential to the bulk liquid in contact with the nanopores in the measurement cells. In some embodiments, the common potential and the common electrode are common to all of the measurement cells. In some embodiments, there exists a working electrode within each measurement cell; in contrast to the common electrode, the working cell electrode is configurable to apply a distinct potential that is independent from the working cell electrodes in other measurement cells.

As further illustrated in FIGS. 10A-10D, the circuit includes a capacitor (NCAP) that models a capacitance associated with the membrane ($C_{bilayer}$) and a resistor that models a resistance associated with the nanopore in different states (e.g., the open-channel state or the states corresponding to having different types of tags or molecules inside the nanopore). The circuit includes a capacitor that models a capacitance associated with the working electrode. The capacitance associated with the working electrode is also referred to as an electrochemical capacitance ($C_{double\ layer}$).

The electrochemical capacitance $C_{double\ layer}$ associated with the working electrode includes a double-layer capacitance and may further include a pseudocapacitance.

Figure 11A:
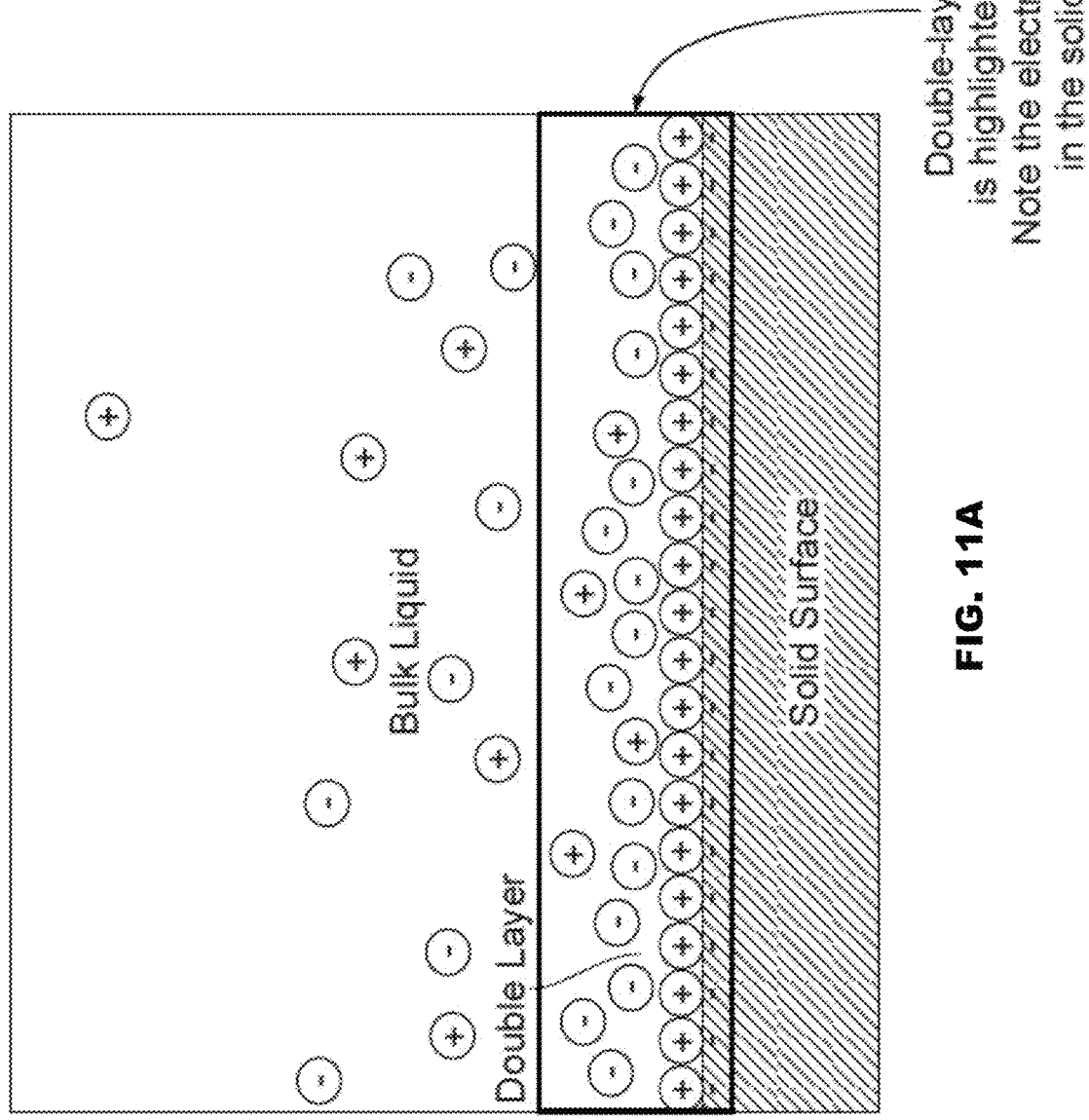
FIG. 11A illustrates a double layer that is formed at any interface between a conductive electrode and an adjacent liquid electrolyte. In the example shown, the electrode surface is negatively charged, resulting in the accumulation of positively charged species in the electrolyte. In another example, the polarity of all charges shown may be opposite to the example shown.

FIG. 11A illustrates a double layer that is formed at any interface between a conductive electrode and an adjacent liquid electrolyte. If a voltage is applied, electronic charges (positive or negative) accumulate in the electrode at the interface between the conductive electrode and adjacent liquid electrolyte. The charge in the electrode is balanced by reorientation of dipoles and accumulation of ions of opposite charge in the electrolyte near the interface. The accumulation of charges on either side of the interface between electrode and electrolyte, separated by a small distance due to the finite size of charged species and solvent molecules in the electrolyte, acts like a dielectric in a conventional capacitor. The term "double layer" refers to the ensemble of electronic and ionic charge distribution in the vicinity of the interface between the electrode and electrolyte.

Figure 11B:
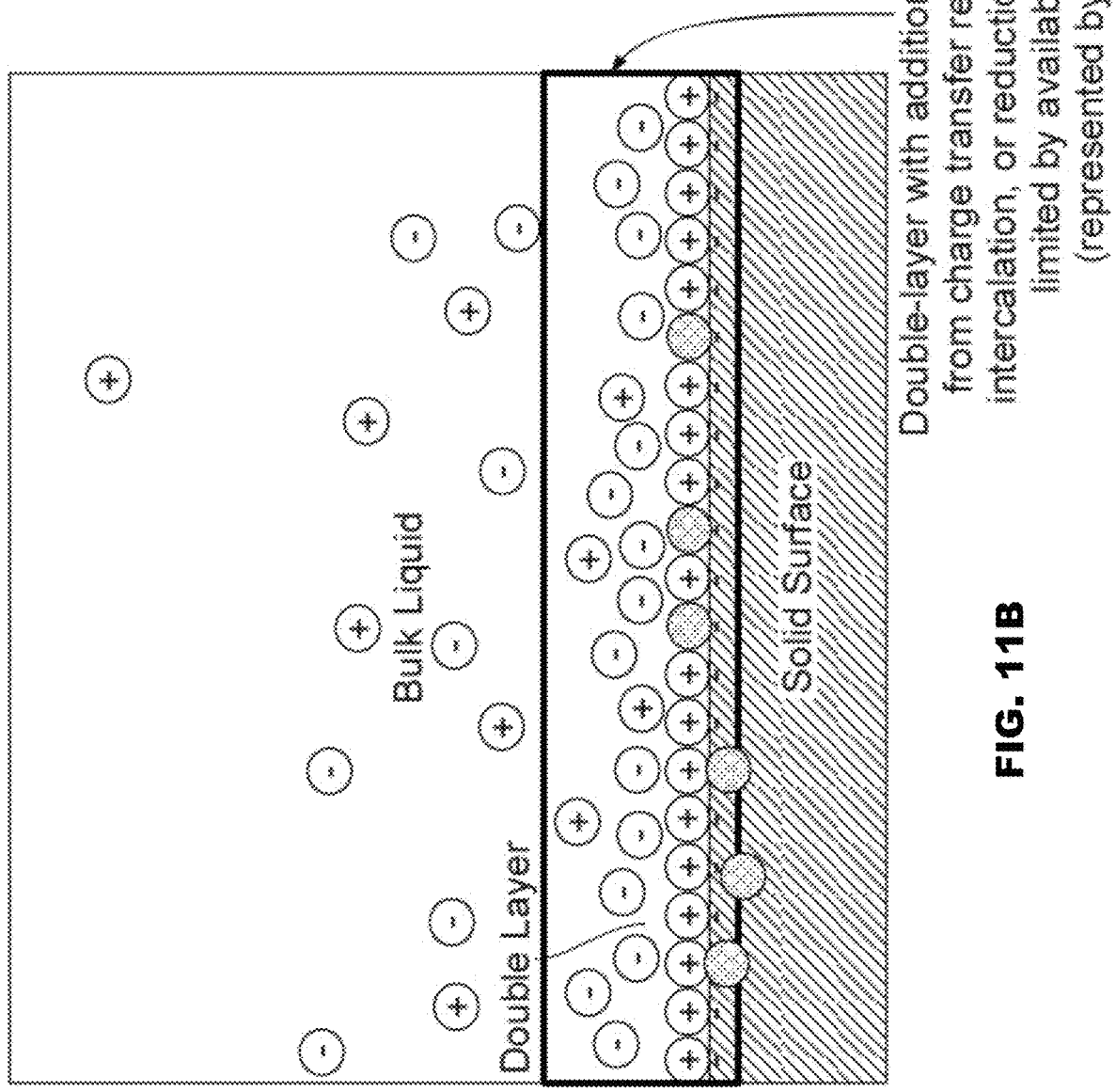
FIG. 11B illustrates a pseudocapacitance effect that can be formed, simultaneously with the formation of a double-layer as in FIG. 11A, at an interface between a conductive electrode and an adjacent liquid electrolyte.

FIG. 11B illustrates a pseudocapacitance effect that can be formed, simultaneously with the formation of a double-layer as in FIGS. 10A-10D at an interface between a conductive electrode and an adjacent liquid electrolyte. A pseudocapacitor stores electrical energy faradaically by electron charge transfer between the electrode and the electrolyte. This is accomplished through electrosorption, reduction-oxidation reactions, or intercalation processes.

Figure 12:
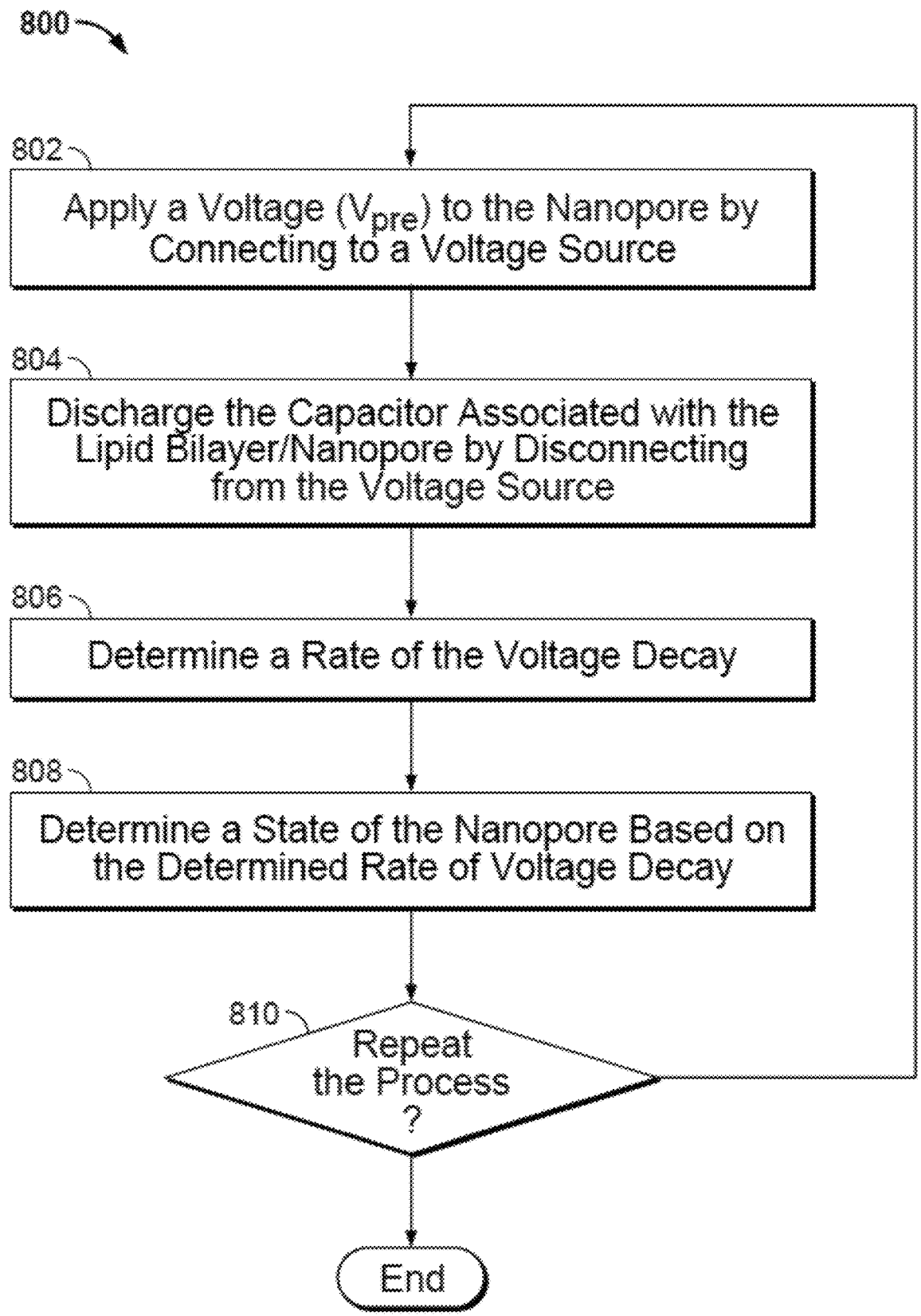
FIG. 12 illustrates an embodiment of a process 800 for analyzing a molecule inside a nanopore, wherein the nanopore is inserted in a membrane.
Figure 13:
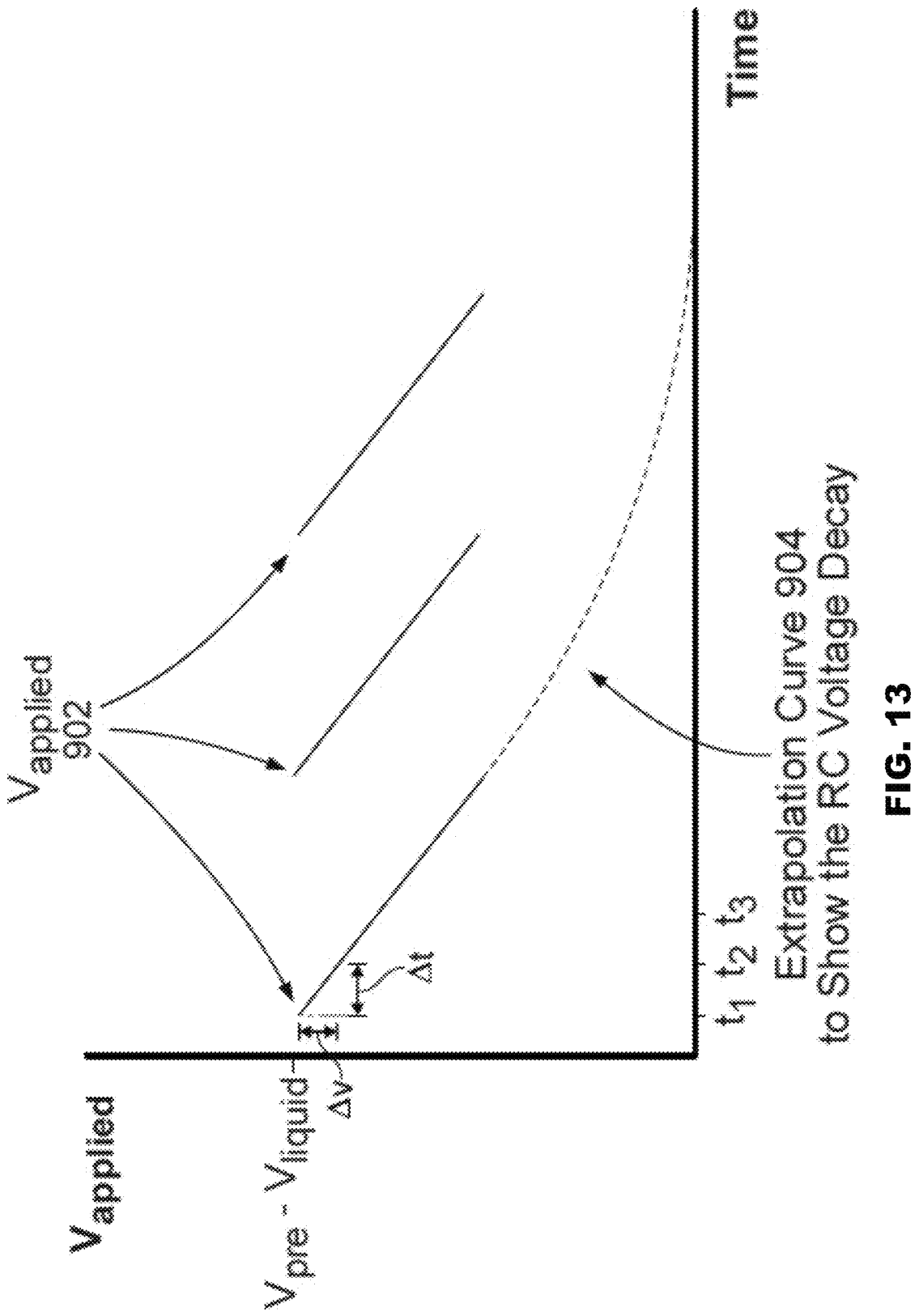
FIG. 13 illustrates an embodiment of a plot of the voltage applied across the nanopore versus time when process 800 is performed and repeated three times.

FIG. 12 illustrates an embodiment of a process 800 for analyzing a molecule inside a nanopore, wherein the nanopore is inserted in a membrane. Process 800 may be performed using the circuitries shown in FIGS. 10A-10D. FIG. 13 illustrates an embodiment of a plot of the voltage applied across the nanopore versus time when process 800 is performed and repeated three times. In some embodiments, the voltage across the nanopore changes over time. The rate of the voltage decay (i.e., the steepness of the slope of the voltage across the nanopore versus time plot) depends on the cell resistance. More particularly, as the resistances associated with the nanopore in different states (e.g., the states corresponding to having different types of molecules inside the nanopore) are different due to the molecules' distinct chemical structure, different corresponding rates of voltage decay may be observed and thus may be used to identify the molecule in the nanopore.

Figure 14:
FIG. 14 illustrates an embodiment of the plots of the voltage applied across the nanopore versus time when the nanopore is in different states.

FIG. 14 illustrates the plots of the voltage applied across the nanopore versus time when the nanopore is in different states. Curve 1002 shows the rate of voltage decay during an open-channel state. In some embodiments, the resistance associated with the nanopore in an open-channel state is in the range of 100 Mohm to 20 Gohm. Curves 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. In some embodiments, the slope of each of the plots is distinguishable from each other.

Increased cell performance of the nanopore based sequencing chip may be achieved by maximizing the electrochemical capacitance (see $C_{double\ layer}$ of FIGS. 10A-10D) associated with the working electrode. In some embodiments, by maximizing $C_{double\ layer}$, the information signal measured by the circuitries shown in FIGS. 10A-10D more stable and the spurious signal convoluted on top of the information signal is minimized. In some embodiments, $C_{double\ layer}$ is maximized such that the impedance associated with $C_{double\ layer}$ is close to an AC (alternating current) short circuit compared with the impedance associated with $C_{bilayer}$ (see $C_{bilayer}$ FIGS. 10A-10D).

Figure 15:
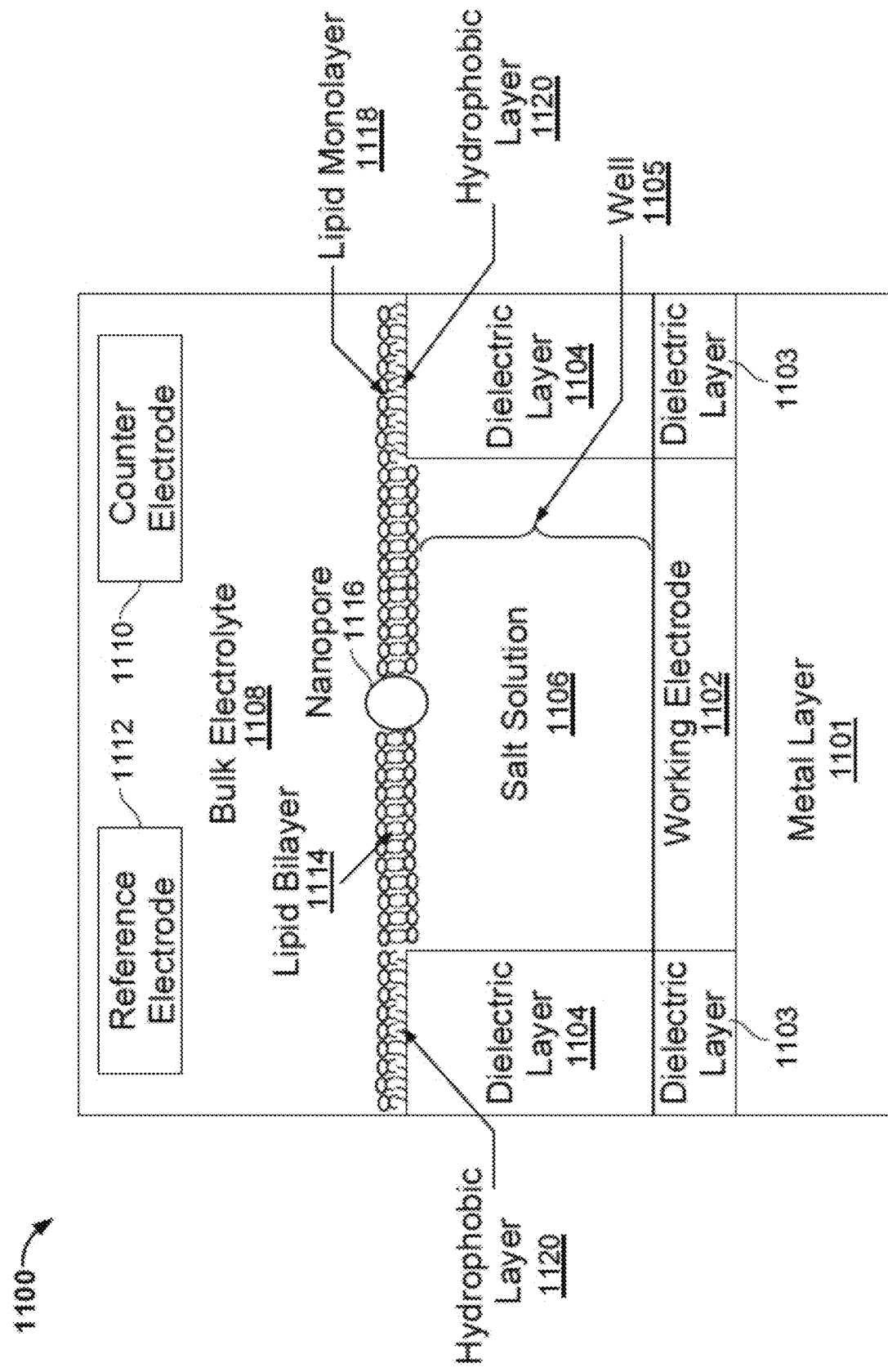
FIG. 15 illustrates an embodiment of a non-faradaic electrochemical cell 1100 of a nanopore based sequencing chip that includes a TiN working electrode with increased electrochemical capacitance.

FIG. 15 illustrates an embodiment of an electrochemical cell 1100 of a nanopore based sequencing chip that includes a working electrode with increased electrochemical capacitance as compared with TiN. In some embodiments, the working electrode with increased electrochemical capacitance as compared with TiN is a material including at least two of ruthenium, oxygen, and nitrogen. In some embodiments, the material comprises ruthenium nitride, ruthenium oxynitride, ruthenium oxide or any composite or mixture thereof. In comparison to TiN which has a double layer capacitance of 77 pF/um2, the ruthenium-containing materials of the present disclosure have a double layer capacitance ranging from between about 180 pF/um$^2$ to about 320 pF/um$^2$. This represents at least a 4× increase in double layer capacitance for the ruthenium-containing materials as compared with a TiN material. As noted in further detail herein, the ruthenium-containing working electrode may be formed in such a manner to have desirable properties, including high double layer capacitance, high porosity, a face centered cubic structure, and/or a dendritic structure. In fact, these properties may be tuned by varying the deposition parameters of the ruthenium-containing material. In some embodiments, the porous structure of the ruthenium-containing material creates a large effective surface area in contact with the electrolyte as described below (see also FIGS. 2F and 2H).

In some embodiments, cell 1100 includes a conductive or metal layer 1101. Metal layer 1101 connects cell 1100 to the remaining portions of the nanopore based sequencing chip. In some embodiments, metal layer 1101 is aluminum or an alloy of aluminum. Cell 1100 further includes a working electrode comprised of a ruthenium-containing material 1102 and a dielectric layer 1103 above metal layer 1101. In some embodiments, working electrode 1102 is circular or octagonal in shape and dielectric layer 1103 forms the walls surrounding working electrode 1102. Cell 1100 further includes a dielectric layer 1104 above working electrode 1102 and dielectric layer 1103. In some embodiments, dielectric layer 1104 forms the insulating walls surrounding a well 1105. In some embodiments, dielectric layer 1103 and dielectric layer 1104 together form a single piece of dielectric. In some embodiments, dielectric layer 1103 is the portion that is disposed horizontally adjacent to working electrode 1102, and dielectric layer 1104 is the portion that is disposed above and covering a portion of the working electrode. In some embodiments, dielectric layer 1103 and dielectric layer 1104 are separate pieces of dielectric and they may be grown separately. Well 1105 has an opening above an uncovered portion of the working electrode.

Inside well 1105, a film of salt solution/electrolyte 1106 is deposited above working electrode 1102. Salt solution 1106 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$)), strontium chloride ($SrCl_2$), Manganese chloride ($MnCl_2$), and magnesium chloride ($MgCl_2$). In some embodiments, the film of salt solution 1106 has a thickness of about three microns (μm). The thickness of the film of salt solution 1106 may range from 0-5 microns.

Dielectric material used to form dielectric layers 1103 and 1104 includes glass, oxide, silicon mononitride (SiN), and the like. The top surface of dielectric layer 1104 may be silanized. Silanization forms a hydrophobic layer 1120 above the top surface of dielectric layer 1104. In some embodiments, hydrophobic layer 1120 has a thickness of about 1.5 nanometer (nm). Alternatively, dielectric material that is hydrophobic such as hafnium oxide may be used to form dielectric layer 1104.

As shown in FIG. 15, a membrane is formed on top of dielectric layer 1104 and spans across well 1105. For example, the membrane includes a lipid monolayer 1118 formed on top of hydrophobic layer 1120 and as the membrane reaches the opening of well 1105, the lipid monolayer transitions to a lipid bilayer 1114 that spans across the opening of the well. Hydrophobic layer 1120 facilitates the formation of lipid monolayer 1118 above dielectric layer 1104 and the transition from a lipid monolayer to a lipid bilayer. A bulk electrolyte 1108 containing protein nanopore transmembrane molecular complexes (PNTMC) and the analyte of interest is placed directly above the well. A single PNTMC/nanopore 1116 is inserted into lipid bilayer 1114 by electroporation. Nanopore 1116 crosses lipid bilayer 1114 and provides the only path for ionic flow from bulk electrolyte 1108 to working electrode 1102. Bulk electrolyte 1108 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$)), strontium chloride ($SrCl_2$), Manganese chloride ($MnCl_2$), and magnesium chloride ($MgCl_2$).

Cell 1100 includes a counter electrode (CE) 1110. Cell 1100 also includes a reference electrode 1112, which acts as an electrochemical potential sensor. In some embodiments, counter electrode 1110 is shared between a plurality of cells and is therefore also referred to as a common electrode. The common electrode can be configured to apply a common potential to the bulk liquid in contact with the nanopores in the measurement cells. The common potential and the common electrode are common to all of the measurement cells.

Figure 16A:
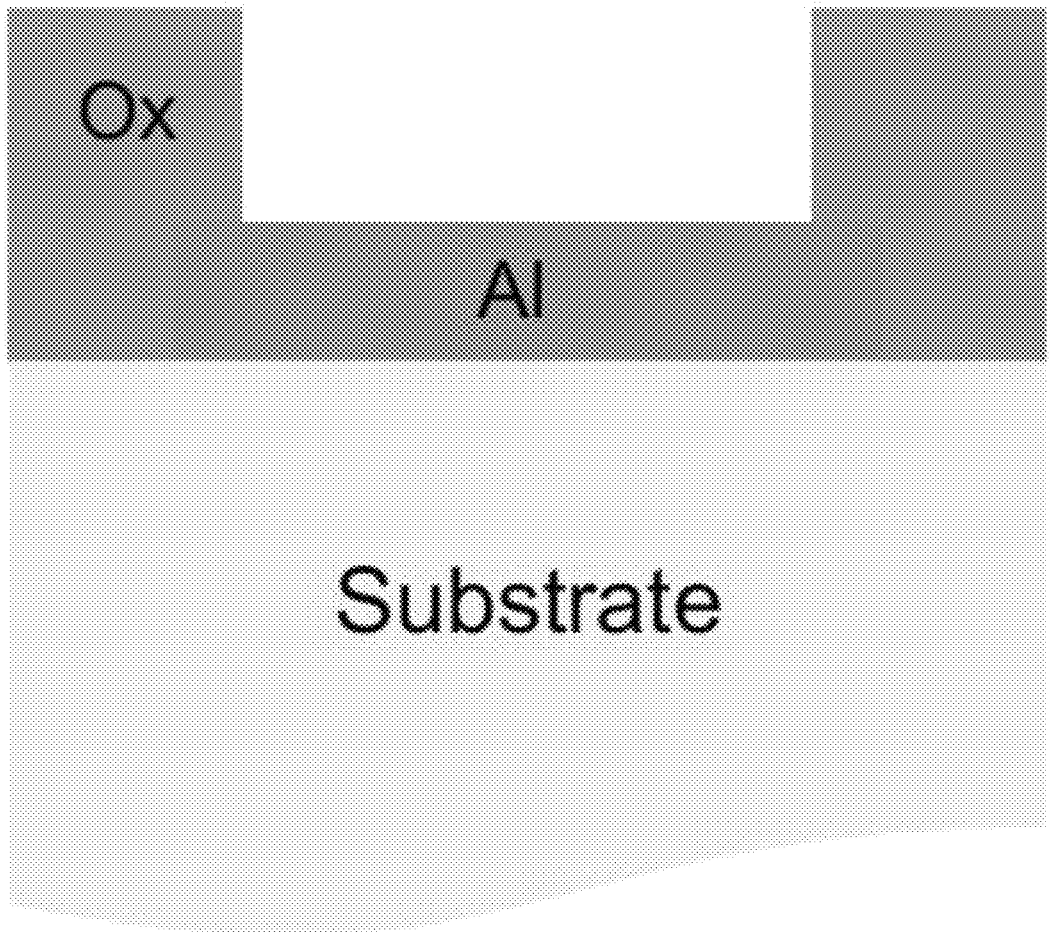
FIGS. 16A-16 D illustrate an embodiment of a process of fabricating an electrode of a nanopore-based sequencing chip that includes a ruthenium-containing material.

FIGS. 16A-16E illustrate a method of forming a working electrode according to some embodiments of the present disclosure. In a first step, a dielectric layer (e.g. $SiO_2$) is deposited on the surface of a conductive layer (e.g. a metal layer comprising metal 6 aluminum). The conductive layer itself may include circuitries that deliver the signals from the cell to the remainder of the chip. In some embodiments, the thickness of the dielectric layer may range from between about 400 nm to about 800 nm. In some embodiments, the dielectric layer is etched to create a hole, thereby exposing a surface of the metal layer. The hole provides a space for depositing or otherwise growing a ruthenium-containing film. In some embodiments, the ruthenium-containing film may be deposited into the hole, i.e. on the surface of the exposed metal layer, using a sputtering process or a physical vapor deposition process as described herein. FIG. 16A illustrates the etched dielectric layer in communication with the metal layer.

Figure 16B:
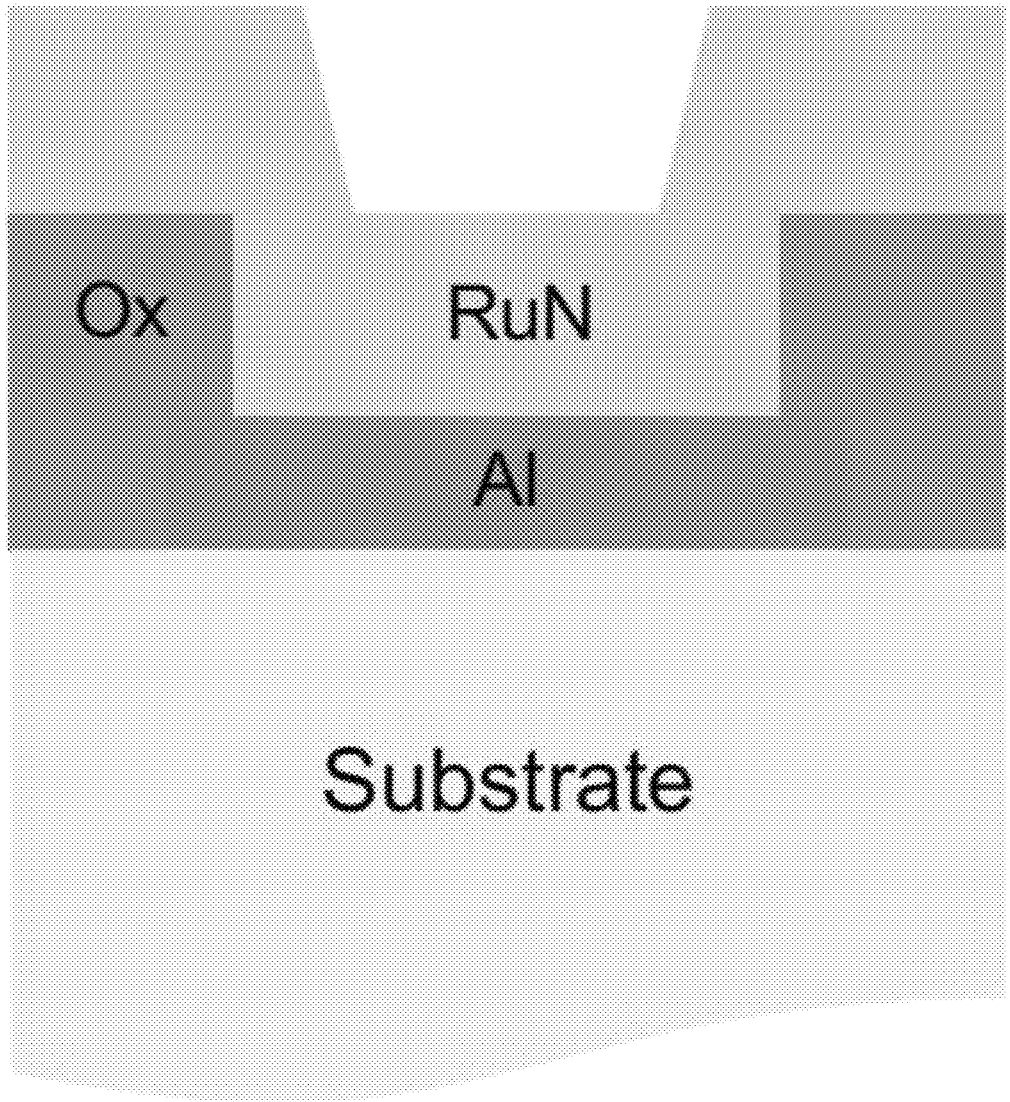

Next, a ruthenium-containing thin film is deposited into the hole onto the surface of the exposed metal layer. In some embodiments, a ruthenium-containing film is provided that has a double layer capacitance ranging from between about 180 pF/um$^2$ to about 320 pF/um$^2$. The deposition of the ruthenium-thin film may be performed according to any of the processes described herein. For example, the ruthenium-containing thin film may be deposited by performing one of a sputter deposition or a plasma vapor deposition using a ruthenium target, wherein the sputter deposition or the plasma vapor deposition process comprises (i) introducing nitrogen into the deposition chamber at a flow rate of between about 10 sccm and 100 sccm, and (ii) introducing argon into the deposition chamber at a flow rate of about 10 sccm, and wherein a deposition pressure within the deposition chamber is maintained at between about 5 mTorr to about 25 mTorr during the deposition, and wherein the deposition is performed using a power ranging from about 50 watts to about 200 watts. In some embodiments, the ruthenium-thin film is grown for a period ranging from between about 1 hour to about 2 hours. In some embodiments, the thickness of the ruthenium-containing thin film ranges from between about 500 nm to about 1000 nm. In some embodiments, the ruthenium-thin film fills the hole and also at least partially covers the oxide layer, as illustrated in FIG. 16B.

In some embodiments, a seed layer is first introduced onto the exposed surface of the metal layer prior to the deposition of the ruthenium-containing thin film. In some embodiments, the seed layer comprises a metal, such as titanium. In some embodiments, the thickness of any seed layer ranges from between about 15 nm to about 30 nm. In some embodiments, the seed layer is sputter deposited.

Figure 16C:
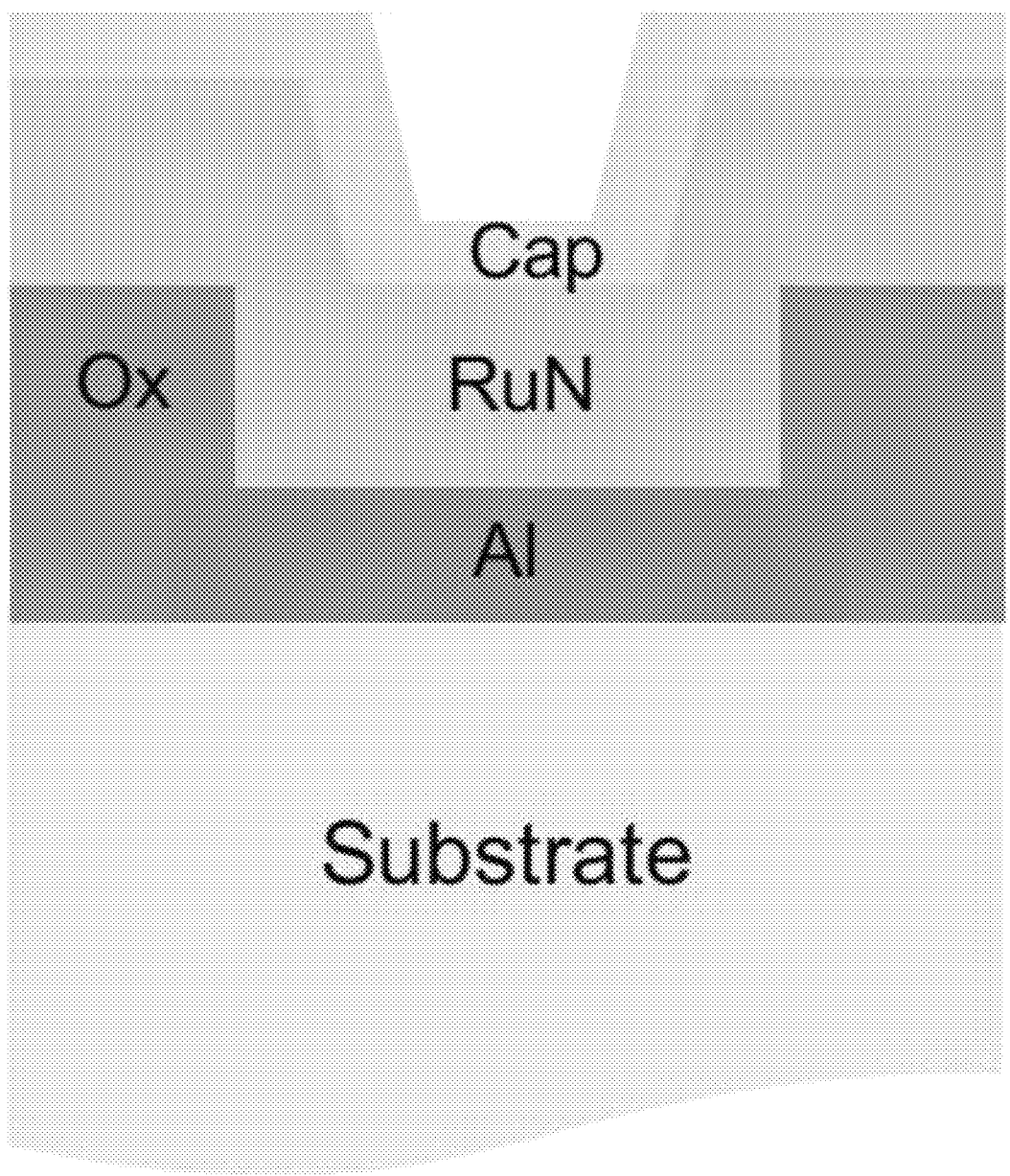

Following the deposition of the ruthenium-containing thin film a cap layer is deposited, such as a dielectric cap comprised of $SiO_2$ or a metal cap comprised of titanium. In some embodiments, the cap is intended to protect the ruthenium-containing thin film during further processing steps. In some embodiments, the cap layer may be deposited by chemical vapor deposition, sputter deposition, or physical vapor deposition. FIG. 16C illustrates an intermediate electrode following the deposition of the cap layer.

Figure 16D:
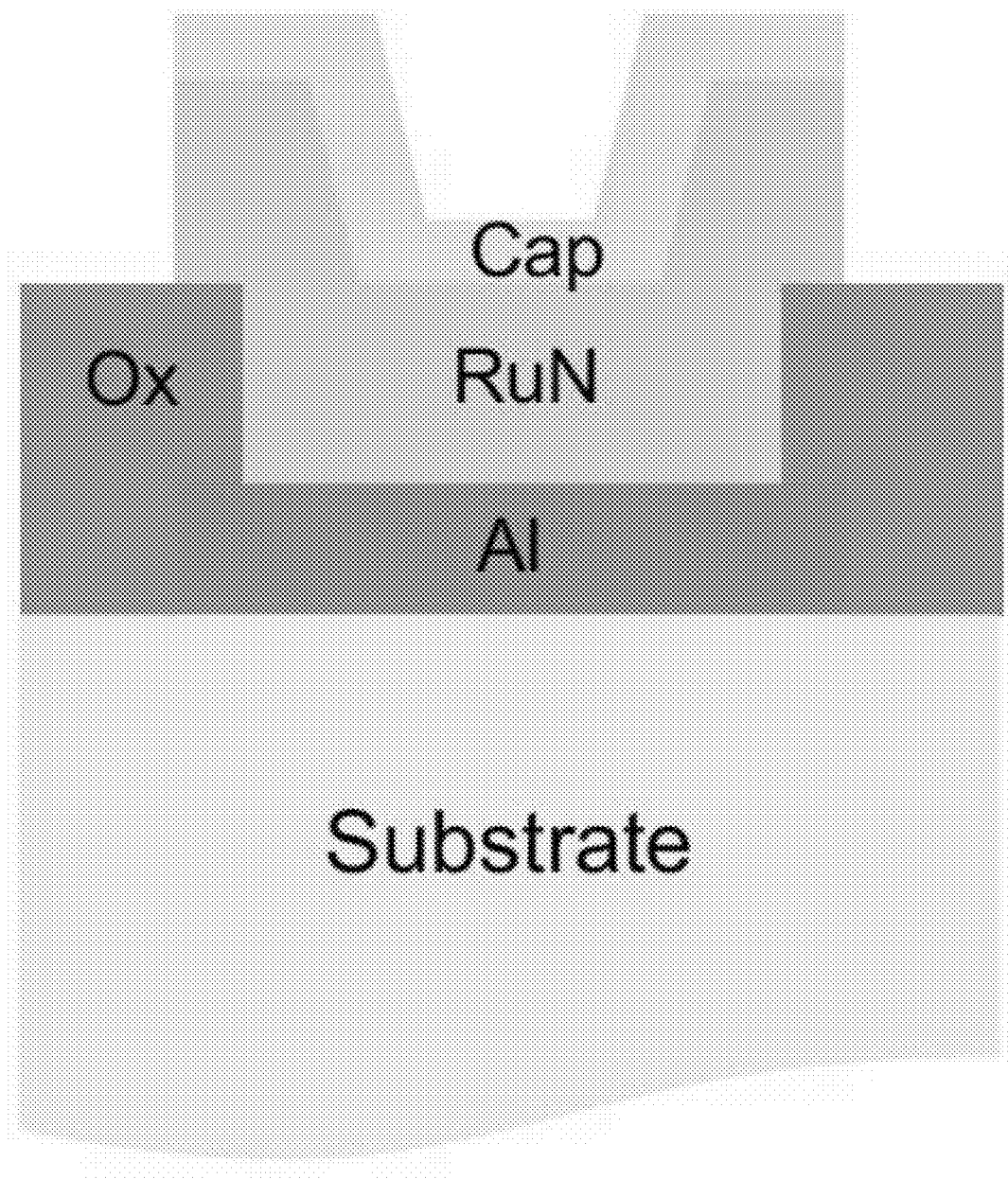

Finally, to isolate one electrode from another in a biochip, photolithographic techniques are employed. For example, a resist may be deposited onto cap layer, whereby a portion of the cap is exposed, and then the resist is developed. Resist patterns without exposure are developed away with developer. The cell is then etched with a plasma etch process or using etch chemistry using $Cl_2$, $BCl_3$ or other chlorine-based reagents. Ruthenium is reactive with chlorine and oxygen to form volatile RuCl and/or RuO products, which may be pumped away inside a sputtering chamber. An example of a final patterned electrode including a cap layer is illustrated in FIG. 16D.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately." even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A nanopore sequencing device comprising: (i) an electrode comprised of a ruthenium-containing material; and (ii) at least one of a reference electrode or counter electrode, wherein the ruthenium-containing material is characterized as having a double-layer capacitance ranging from between 180 pF/um2 to 320 pF/um2.

2. A chip comprising a plurality of individually addressable nanopores, wherein each individually addressable nanopore is in fluidic communication with a working electrode comprised of a ruthenium-containing material, wherein the ruthenium-containing material is characterized as having a double-layer capacitance ranging from between 180 pF/um2 to 320 pF/um2.

3. The chip of claim 2, wherein the working electrode comprises a dendritic structure as determined by cross-sectional scanning electron microscopy.

4. A nanopore sequencing device comprising: a working electrode comprised of a ruthenium-containing material; and a dielectric layer, wherein a first portion of the dielectric layer is disposed horizontally adjacent to the working electrode and a second portion of the dielectric layer is disposed above the working electrode, and wherein the dielectric layer forms a well having an opening above the working electrode, wherein the ruthenium-containing material is characterized as having a double-layer capacitance ranging from between 180 pF/um2 to 320 pF/um2.

5. A nanopore sequencing device comprising: (i) an electrode comprised of a ruthenium-containing material; and (ii) at least one of a reference electrode or counter electrode, wherein the ruthenium-containing material is characterized as having a surface composition ratio of (N+O)/Ru as measured by X-ray photoelectron spectroscopy ranging from between 1.5 and 3.5.

6. The nanopore sequencing device of claim 5, wherein the surface composition ratio ranges from 1.8 to 3.0.

7. The nanopore sequencing device of claim 5, wherein the surface composition ratio ranges from 2 to 2.5.

8. A chip comprising a plurality of individually addressable nanopores, wherein each individually addressable nanopore is in fluidic communication with a working electrode comprised of a ruthenium-containing material, wherein the ruthenium-containing material is characterized as having a surface composition ratio of (N+O)/Ru as measured by X-ray photoelectron spectroscopy ranging from between 1.5 and 3.5.

9. The chip of claim 8, wherein the surface composition ratio ranges from 1.8 to 3.0.

10. The chip of claim 8, wherein the surface composition ratio ranges from 2 to 2.5.

11. A nanopore sequencing device comprising: a working electrode comprised of a ruthenium-containing material; and a dielectric layer, wherein a first portion of the dielectric layer is disposed horizontally adjacent to the working electrode and a second portion of the dielectric layer is disposed above the working electrode, and wherein the dielectric layer forms a well having an opening above the working electrode, wherein the ruthenium-containing material is characterized as having a surface composition ratio of (N+O)/Ru as measured by X-ray photoelectron spectroscopy ranging from between 1.5 and 3.5.

12. The nanopore sequencing device of claim 11, wherein the surface composition ratio ranges from 1.8 to 3.0.

13. The nanopore sequencing device of claim 11, wherein the surface composition ratio ranges from 2 to 2.5.

14. A nanopore sequencing device comprising: (i) an electrode comprised of a ruthenium-containing material; and (ii) at least one of a reference electrode or counter electrode, wherein the ruthenium-containing material is characterized as having a nitrogen content of at least 5% nitrogen but not more than 15%.

15. The nanopore sequencing device of claim 14, wherein the electrode comprises a dendritic structure as determined by cross-sectional scanning electron microscopy.

16. A chip comprising a plurality of individually addressable nanopores, wherein each individually addressable nanopore is in fluidic communication with a working electrode comprised of a ruthenium-containing material, wherein the ruthenium-containing material is characterized as having a nitrogen content of at least 5% nitrogen but not more than 15%.

17. A nanopore sequencing device comprising: a working electrode comprised of a ruthenium-containing material; and a dielectric layer, wherein a first portion of the dielectric layer is disposed horizontally adjacent to the working electrode and a second portion of the dielectric layer is disposed above the working electrode, and wherein the dielectric layer forms a well having an opening above the working electrode, wherein the ruthenium-containing material is characterized as having a nitrogen content of at least 5% nitrogen but not more than 15%.

18. The nanopore sequencing device of claim 17, wherein the electrode comprises a dendritic structure as determined by cross-sectional scanning electron microscopy.

* * * * *